(12) United States Patent
Snell et al.

(10) Patent No.: US 8,216,593 B2
(45) Date of Patent: Jul. 10, 2012

(54) PARASITE VACCINE

(75) Inventors: William J. Snell, Richardson, TX (US);
Yanjie Liu, Dallas, TX (US); Robert E. Sinden, Wokingham (GB); Oliver Billker, Oxford (GB); Rita Tewari, Nottingham (EP)

(73) Assignees: Board of Regents, The University of Texas System, Austin, TX (US);
Imperial College of London, London (GB)

( * ) Notice: Subject to any disclaimer, the term of this patent is extended or adjusted under 35 U.S.C. 154(b) by 0 days.

(21) Appl. No.: 11/856,036

(22) Filed: Sep. 15, 2007

(65) Prior Publication Data

US 2008/0241075 A1    Oct. 2, 2008

Related U.S. Application Data

(60) Provisional application No. 60/845,122, filed on Sep. 16, 2006.

(51) Int. Cl.
| | | |
|---|---|---|
| *A61K 39/00* | (2006.01) | |
| *A61K 39/38* | (2006.01) | |
| *A61K 39/018* | (2006.01) | |
| *A61K 39/015* | (2006.01) | |
| *A61K 38/00* | (2006.01) | |
| *A61K 38/16* | (2006.01) | |
| *C07K 14/00* | (2006.01) | |

(52) U.S. Cl. ............... 424/269.1; 424/184.1; 424/270.1; 424/272.1; 424/273.1; 424/265.1; 530/300; 530/350

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,877,612 A | 10/1989 | Berger et al. | |
| 4,965,188 A | 10/1990 | Mullis et al. | |
| 6,248,329 B1 * | 6/2001 | Chandrashekar et al. . | 424/191.1 |
| 6,617,156 B1 * | 9/2003 | Doucette-Stamm et al. ........................... | 435/320.1 |
| 6,660,498 B1 | 12/2003 | Hui et al. | |
| 2003/0211089 A1 * | 11/2003 | Sayre et al. ................. | 424/93.21 |
| 2005/0220822 A1 * | 10/2005 | Hoffman et al. ........... | 424/272.1 |

OTHER PUBLICATIONS

Definition of Vaccine: The Dictionary of Immunology, Herbert et al eds, Academic Press, 1995.*
Harlow et al, Antibodies A Laboratory Manual, Cold Spring Harbor Laboratory Press Inc., 1988 pp. 23-25, 27-33 and 72-74.*
Greenspan et al, Nature Biotechnology 17:936-937, 1999.*
Chapter 2, section 2.1, p. 4 , Tarin and Cano (Eds). Fertilization in Protozoan and Metazoan animals. Cellular and Molecular Aspects. Springer, 2000.*
Billker, O., et al., "Calcium and a calcium-dependent protein kinase regulate gamete formation and mosquito transmission in a malaria parasite." Cell (2004), 117:503-514.
Breman, J. G., et al., "Conquering the intolerable burden of malaria: what's new, what's needed: a summary." Am J Trop Med Hyg (2004), 71:1-15.
Dessens, J. T., et al., "SOAP, a novel malaria ookinete protein involved in mosquito midgut invasion and oocyst development." Mol Microbiol (2003), 49:319-329.
Inoue, N., et al., "The immunoglobulin superfamily protein Izumo is required for sperm to fuse with eggs." Nature (2005), 434:234-238.
Johnson, M. A., et al., "Arabidopsis hapless mutations define essential gametophytic functions." Genetics (2004), 168:971-982.
Li, S., et al., Viral vectors for malaria vaccine development, Vaccine (2007), 25:2567-2574.
Misamore, M. J., et al., "The Chlamydomonas Fus1 protein is present on the mating type plus fusion organelle and required for a critical membrane adhesion event during fusion with minus gametes." Mol Biol Cell (2003), 6:2530-2542.
Mori, T., et al., "Generative Cell Specific 1 is essential for angiosperm fertilization." Nat Cell Biol (2006), 8:64-71.
Pan, J., et al., "Signal transduction during fertilization in the unicellular green alga, Chlamydomonas." Curr Opin Microbiol (2000), 3:596-602.
Pollock, S. V., et al., "Rubisco activase is required for optimal photosynthesis in the green alga Chlamydomonas reinhardtii in a low-CO(2) atmosphere." Plant Physiol (2003), 133:1854-1861.
Reininger, L., et al., "A nima-related protein kinase is essential for completion of the sexual cycle of malaria parasites." J Biol Chem (2005), 280:31957-31964.
International Search Report and Written Opinion for PCT/US2007/078595 dated Apr. 16, 2008.
Abba, A.K., et al., "Cellular and Molecular Immunology," Philadelphia: W.B. Saunders Company (2000), Chapter 15, pp. 360-362.
Oplinger, A., "NIAID Tackles Malaria in Vaccine Lab," NIH Record, (May 2005), vol. LVII, No. 9.
Struik, S. S., "Does Malaria Suffer from Lack of Memory?" Immunological Reviews (2004), 201:268-290.
Tongren, J. E., Malaria Vaccines: If at First You Don't Succeed, Trends in Parasitology (2004), 20:604-610.

* cited by examiner

*Primary Examiner* — Robert Mondesi
*Assistant Examiner* — Oluwatosin Ogunbiyi
(74) *Attorney, Agent, or Firm* — Edwin S. Flores; Chalker Flores, LLP

(57) ABSTRACT

The present invention includes compositions and methods for the development and use of a vaccine that includes one or more FusM antigens in a carrier adapted to trigger a FusM-specific immune response in the human blood stream.

9 Claims, 12 Drawing Sheets

FIG. 1F

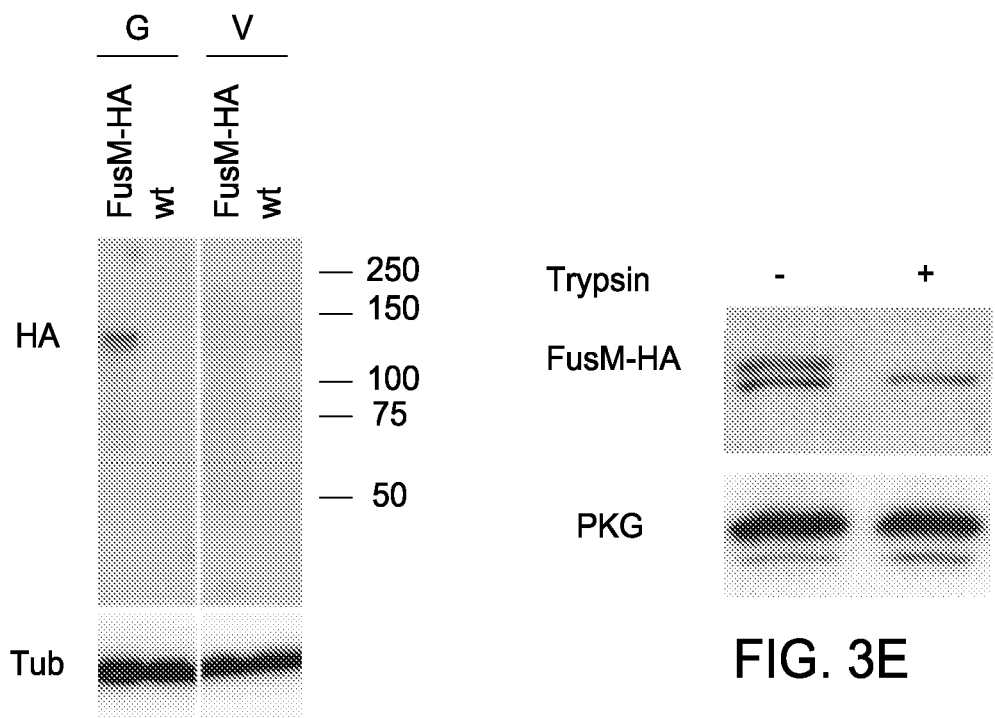
FIG. 3D
FIG. 3E
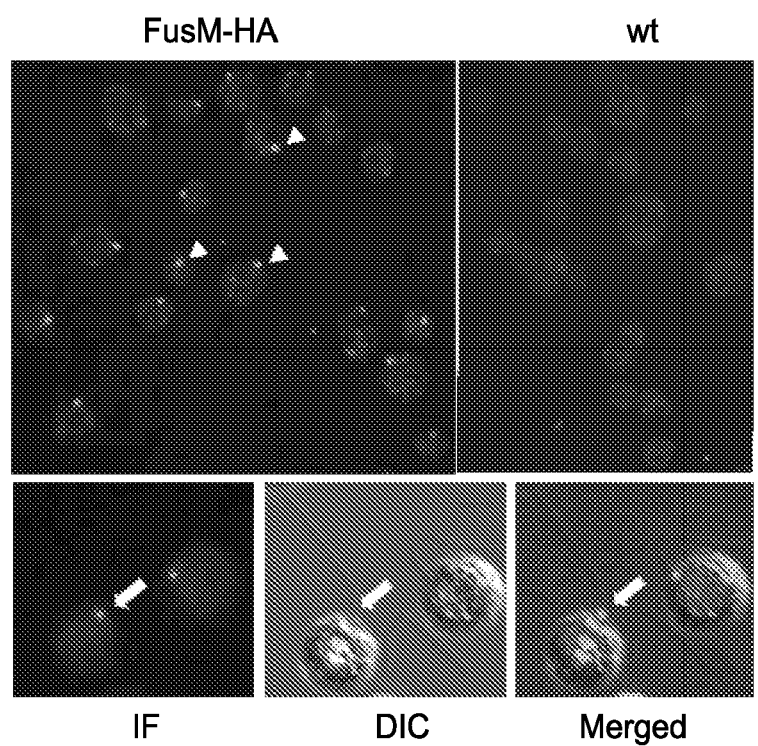
FIG. 3F

PARASITE VACCINE

CROSS-REFERENCE TO RELATED APPLICATIONS

This application claims priority to U.S. Provisional Patent Application Ser. No. 60/845,122, filed Sep. 16, 2006, the entire contents of which are incorporated herein by reference.

STATEMENT OF FEDERALLY FUNDED RESEARCH

This invention was made with U.S. Government support under Contract No. R01GM56778-6 awarded by the NIH. The government may have certain rights in this invention.

TECHNICAL FIELD OF THE INVENTION

The present relates to vaccination against parasites, and more particularly, compositions and methods for the therapeutic use of FusM protein and portions thereof to vaccinate patients and patient populations.

BACKGROUND OF THE INVENTION

Without limiting the scope of the invention, its background is described in connection with anti-parasitic vaccines.

Malaria and related parasitic diseases continue to bring misery to much of the world's population. Malaria and related parasitic protozoa cause untold human misery worldwide. It is estimated that over 1 billion people are infected with the malaria-causing organism, *Plasmodium*, and 3 million persons die each year from the disease (Breman et al., 2004). Those who do not die endure long suffering. The disease causes billions of dollars in lost productivity. Humans with Sleeping Sickness, Chagas disease, Cryptosporidiosis, and Toxoplasmosis also suffer greatly. Many people die from the diseases, or lose their ability to be productive members of their communities. Similarly, these and other parasites annually kill large numbers of the vertebrates (cows, sheep, goats, sheep, pigs, and chickens) that are human primary food sources worldwide (Roberts and Janovy, 2005).

Several methods are being used to roll back malaria and other of these parasitic diseases, including reduction of insect vectors, drugs, and vaccines. None of these are completely effective, though, and it is estimated that more humans are infected now with malaria than were infected 20 years ago. One problem with existing vaccines is that they target surface antigens of poorly understood or unknown function. In addition, the targets mutate and render the organism resistant to the vaccine. Therefore, new discoveries and new approaches are essential to combat malaria and related parasitic protozoan diseases.

SUMMARY OF THE INVENTION

The present invention includes vaccines, constructions, host cells, and vectors that include or express one or more protozoan FusM antigens for use with, e.g., a carrier adapted to trigger a FusM-specific immune response. The skilled artisan may also recognize that FusM has been referred to as HAP2 (Hapless 2) or GCS1 (generative cell specific 1). In one embodiment, the present invention is a vaccine having at least a portion of a protozoan FusM mating protein that is immunogenic; and a carrier. The vaccine may also include an adjuvant, a pharmaceutically acceptable salt, an excipient, a preservative, a binder or a pharmaceutically acceptable liquid. The FusM protein is obtained from a protozoan that has been heat-killed, attenuated, chemically-inactivated, mechanically inactivated or combinations thereof, e.g., the FusM protein may be recombinant, and the portion of the FusM protein may even be selected to trigger a cytotoxic T-cell immune response, a humoral immune response, a mucosal immune response or a combination thereof. The vaccine may include a FusM protein may be lyophilized, vacuum-dried, vacuum heat-dried, freeze-sprayed or combinations thereof. Examples of carriers for the vaccine include an excipient, an adjuvant, an absorption enhancer, a release-rate controlling polymer, a stability enhancer, or combinations thereof. In one example, the FusM protein is inserted for expression in a carrier virus, an attenuated bacterium or an attenuated blood-stage/sporozoite. In another example, the FusM protein may be inserted as gene or gene fragments that are expressed in a carrier virus. The carrier may be an adjuvant selected from Complete Freund's Adjuvant, Incomplete Freund's Adjuvant, alum, a carrier virus, high molecular weight polysaccharides, glycoproteins, microparticles, liposomes, and combinations thereof.

Examples of protozoan sources for the vaccine include those selected from the group consisting of the Phylum Apicomplexa or the Class Kinetoplastida. More particular examples of the sources for the protein, genes and/or antigen include protozoans selected from the group consisting of the Phylum Apicomplexa further defined as comprising *Babesia* sp., *Cryptosporidium* sp., *Plasmodium* sp., and *Toxoplasma* sp. *Plasmodium* sp., *Plasmodium falciparum*, *Plasmodium vivax*, *Cryptosporidium parvum*, *Cryptosporidium hominis*, *Eimeria* sp., *Eimeria tenella*, *Theileria* sp., *Theileria parva*, *Toxoplasma* sp. and *Toxoplasma gondii*. Other examples include protozoans selected from the Class Kinetoplastida, further defined as comprising *Trypanosoma brucei* subspecies, *Trypanosoma cruzi*, *Leishmania* sp., and *Leishmania major*. The vaccine may be formulated for oral, subcutaneous, intramuscular, nasal, intradermal, pulmonary, intraalveolar, intravaginal, intrarectal, intraperitoneal or intravenous administration. Examples of portions of a protozoan FusM mating protein may be selected from SEQ ID NOS 1-14, or enough contiguous nucleic acids or amino acids to generate an immunogenic FusM antigen.

Another embodiment of the present invention includes a method for modulating a protozoan population by identifying a human population in need of reduction in a protozoan population; and vaccinating a majority of the population with a vaccine comprising an immunogenic portion of a FusM protein. Another method of the present invention includes a method of providing immunity to a vertebrate host by vaccinating the host with an antigen comprising a polypeptide that causes immunity against a protozoan FusM protein. The immunity may be innate immunity, passive immunity, active immunity or a combination thereof. For use with the method, the protozoan is selected from the group consisting of the Phylum Apicomplexa or the Class Kinetoplastida, Phylum Apicomplexa further defined as comprising *Babesia* sp., *Cryptosporidium* sp., *Plasmodium* sp., and *Toxoplasma* sp. *Plasmodium* sp., *Plasmodium falciparum*, *Plasmodium vivax*, *Cryptosporidium parvum*, *Cryptosporidium hominis*, *Eimeria* sp., *Eimeria tenella*, *Theileria* sp., *Theileria parva*, *Toxoplasma* sp. and *Toxoplasma gondii* or even Class Kinetoplastida, further defined as comprising *Trypanosoma brucei*, *Trypanosoma cruzi*, *Leishmania* sp., and *Leishmania major*. The host that is vaccinated may be a human, a dog, a cat, a monkey, a horse, a cow, a pig or a chicken.

Another embodiment of the present invention is a vaccine against malaria comprising at least a portion of a protozoan FusM protein that is immunogenic, wherein the protozoan is selected from the group consisting of *Plasmodium* sp., *Plasmodium falciparum, Plasmodium vivax,* and *Plasmodium berghei, Plasmodium ovale* and *Plasmodium malariae*. Another embodiment is a transmission-blocking vaccine that includes an amount of an anti-FusM antibody or a fragment thereof sufficient to passively block the majority of the mating of a protozoan in vivo. The antibody or a fragment thereof is administered to a patient in need of passive immunity. The present invention also includes an inhibitor of protozoan mating by providing a medicament (and the use thereof) that includes an anti-FusM antibody or fragment thereof. In one aspect, the antibody or fragment thereof is disposed in a carrier that is suitable for aerosol delivery, immediate release, time-release dosage, mixed-release or suitable for release into a water reservoir.

Another embodiment of the present invention includes a method for screening anti-parasitic drugs by obtaining one or more FusM mutant proteins; contacting the one or more FusM mutant proteins with one or more candidate agents that to determine if they inhibit the formation of a FusM complex, and further isolating and characterizing the candidate agents for those that prevent gamete formation of parasites. The method may also include the step of testing the one or more candidate agents for toxicity in vertebrates. The method may also include the step of testing the one or more candidate agents for toxicity in humans. The method may also include the step of characterizing the molecular structure of the one or more candidate agents.

Yet another embodiment of the present invention includes a live-attenuated mutant protozoan vaccine comprising a protozoan that is blocked developmentally phenotypically or chemically at the gamete phase, such that the host raises immunity to the FusM protein. Other embodiment includes an isolated nucleic acid molecule, the complementary sequence of which hybridizes fully, under highly stringent conditions (aqueous buffer, 65° C.) to the nucleotide sequences set forth in SEQ ID NO: 1 to 14, wherein the nucleic acid molecule encodes a protozoan mating protein antigen, wherein the protozoan mating protein antigen encodes a protein that triggers an immune response in a mammal, or even an isolated nucleic acid molecule that encodes a FusM mating protein comprising the nucleotide sequence of SEQ ID NO: 11 to 20. The isolated nucleic acid molecule comprising a nucleotide sequence which encodes a protein comprising the amino acid sequence of SEQ ID NOS.: 1-14 or the amino acid expressed therefrom. Another embodiment of the present invention is an expression vector comprising the isolated nucleic acid molecule of SEQ ID NOS.: 1 to 14, operably linked to a promoter. Another embodiment is a recombinant vector, transformed or transfected with the isolated nucleic acid molecule of SEQ ID NOS.: 1 to 14 or the amino acid expressed therefrom. The recombinant vector is further defined as a live, attenuated virus, bacterium or protozoan vector; a heat-killed virus, bacterium or protozoan vector; a chemically inactivated virus, bacterium or protozoan vector; a mechanically inactivated virus, bacterium or protozoan vector; or combinations thereof.

BRIEF DESCRIPTION OF THE DRAWINGS

For a more complete understanding of the features and advantages of the present invention, reference is now made to the detailed description of the invention along with the accompanying figures and in which:

Figure 1F:
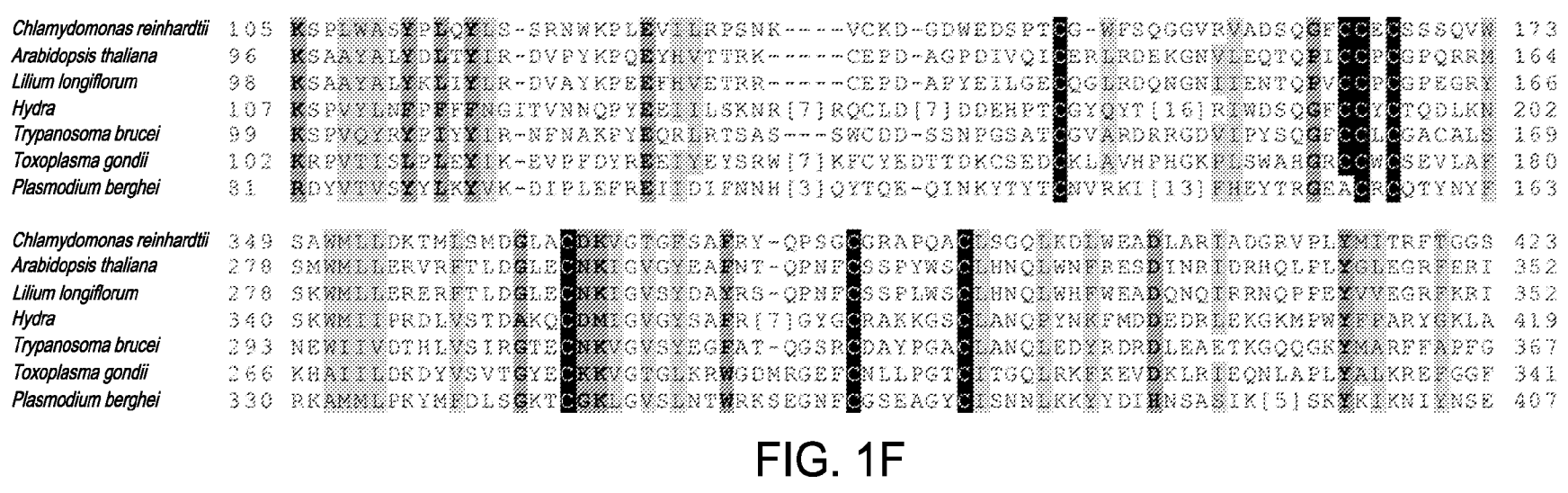

FIGS. 1A to 1F. FusM is required for fertilization in *Chlamydomonas* and phylogenetically conserved in many eukaryotes. (FIG. 1A) Differential interference contrast microscopy (DIC) images of (left panel) a quadriflagellated zygote formed from fusion of a wt female gamete with a wt male gamete and (right panel) a wt female gamete undergoing flagellar adhesion with a 63B10 male, but failing to fuse. (FIG. 1B) Structure of the FusM gene and location of the aphVIII plasmid. (FIG. 1C) PCR using primers p1/p2 and p1-p17 showing the absence of intact FusM in 63B10 gametes and its reappearance in several 63B10 gametes rescued for fusion with the wt FusM gene. (FIG. 1D) Large aggregates of zygotes were present only in mixtures of wt female and male gametes and wt female and 63B10 male gametes rescued with the wt FusM gene (63B10-C9). (FIG. 1E) Phylogenetic tree illustrating the relationships of FusM proteins from several species. (FIG. 1F) Alignment of two conserved regions of FusMs from several species (SEQ ID NOs.: 1-14, respectively). Positions with conserved cysteines are in black background, other conserved positions are in gray background. Uncharged residues in positions with mainly hydrophobic residues are in yellow background. Residues in long loops are not shown in this figure and are replaced by brackets that indicate the number of residues in the loop. The numbers of beginning and ending residues for the regions are shown. See Table S1 for the full alignments of the proteins.

(FIG. 2A) Structure of the *Plasmodium* FusM gene and gene replacement construct. Short arrows indicate oligonucleotides used for PCR genotyping. (FIG. 2B) Southern hybridization of EcoRI-digested genomic DNA using the 5' targeting sequence as a probe. Arrowheads indicate diagnostic 2.8 kb (wt) and 5.0 kb (FusM) bands. (FIG. 2C) Diagnostic PCR with genomic DNA templates and oligonucleotides 525/526 to test for the presence of FusM, and oligonucleotides 524/70 to detect a unique 1 kb product across the integration site. (FIG. 2D) RT-PCR detection of FusM transcript in parasite lines and stages (the expected larger product from genomic DNA includes one intron). (FIG. 2E) Representative images of midguts from *A. stephensi* mosquitoes 10 d after feeding on wt and fusm infected mice (scale bar, 100 μm) and bar chart showing average numbers of oocysts per gut (error bar=s.e.m., n=47 wt or fusm-exposed mosquitoes from 3 independent experiments). The overall prevalence of infection was 87% for wt, and 0% for fusm. (FIG. 2F) Immunofluorescence images of live 20 h *Plasmodium* cultures immunostained for the macrogamete/zygote marker P28 as described (24). Elongate ookinetes (asterisks) were absent from the fusm mutant (scale bar, 10 μm), which possessed only round macrogametes. The bar chart shows ookinete conversion rates for wt and fusm clone 8. Conversion rate is expressed as the percentage of P28-positive parasites that had progressed to the ookinete stage (error bar=s.d.; n=3).

FIGS. 3A to 3F. FusM is present at the surface of the male mating structure in *Chlamydomonas* and has a male-specific function late in fertilization in both *Chlamydomonas* and *Plasmodium*. (FIG. 3A) Unlike *Chlamydomonas* fusm males, which failed to fuse when mixed with wt females, *Chlamydomonas* fusm females were capable of fusion with wt males (see Methods for strategy used to generate females missing the wt FusM and containing only the mutant fusm). The upper panel shows Southern hybridization of wt and mutant strains, documenting that the fusm females contained only the disrupted FusM gene. The upper, wt FusM NotI fragment is 5.3 kb and the lower fragment from the 63B10 allele is 1.3 kb. The lower panel shows the percent of the indicated gametes that fused when mixed with wt gametes of the opposite sex. (FIG. 3B) In vitro malaria ookinete conversion analysis demonstrates that the *Plasmodium* fusm mutant shows productive cross-fertilization with the nek4 sterility mutant, which produces functional males only, and not with cdpk4, which produces functional females only (error bar=s.d.; n=3). The ookinete conversion rates are about half that of wt, because only 50% of the female gametes are competent to be fertilized. (FIG. 3C) *Chlamydomonas* FusM functions after gamete activation. 63B10 gametes were incubated with wt females, flagella isolated from wt females, db-cAMP, or medium (control) and the percent of cells that were activated was determined by measuring cell wall loss. (FIG. 3D) Immunoblotting with an anti-HA antibody documents that 63B10 cells rescued with HA-tagged FusM expressed FusM-HA protein only in the gamete phase of their life cycle. (FIG. 3E) Immunoblotting with anti-HA antibody shows that the upper form of FusM-HA on live FusM-HA gametes was sensitive to treatment with 0.01% trypsin for 20 min at room temperature. (FIG. 3F) Anti-HA immunostaining combined with DIC microscopy of FusM-HA gametes shows that FusM-HA is expressed between the two flagella at the site of the male mating structure.

(FIG. 4A) Activated live 63B10 gametes, like activated live wt males, adhered via their mating structures to activated, fixed, fluorescently tagged imp2 females, which are incapable of flagellar adhesion (upper panel, differential interference microscopy; lower panel, fluorescence; arrowheads indicate the imp2 females). The percent (+/−s.e.m.) of imp2 gametes forming pairs when mixed with an excess of activated 63B10 or wt males is shown below the figure (average from 2 independent experiments; n=150-200 imp2 cells examined in each). Similar results were obtained when the agglutinin mutant imp5 was used (not shown). Between 0 and 6% pairs were detected in controls in which activated live imp2 gametes were mixed with the fixed imp2 gametes (not shown). (FIG. 4B) FusM is essential for membrane merger. The plasma membranes of activated female gametes were labeled with the fluorescent lipid PKH26, mixed with wt or 63B10 male gametes, and the live cells were examined by epifluorescence and DIC microscopy. (FIG. 4C) Efficiency of exflagellation, gamete adhesion and gamete fusion in wt, p48/45, and fusm strains of *Plasmodium* (error bar=s.d.; n=3 experiments, each examining 100 gametocytes).

DETAILED DESCRIPTION OF THE INVENTION

Figure 1B:
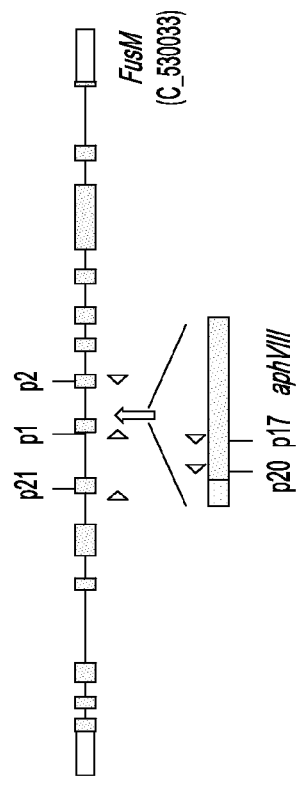
Figure 1D:
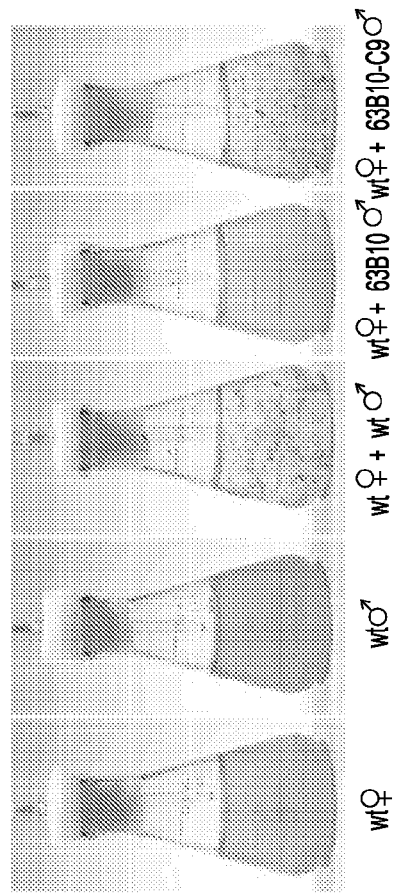
Figure 1A:
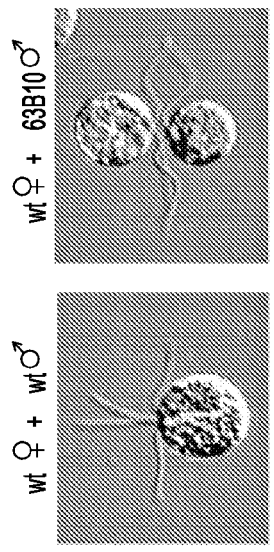
Figure 1C:
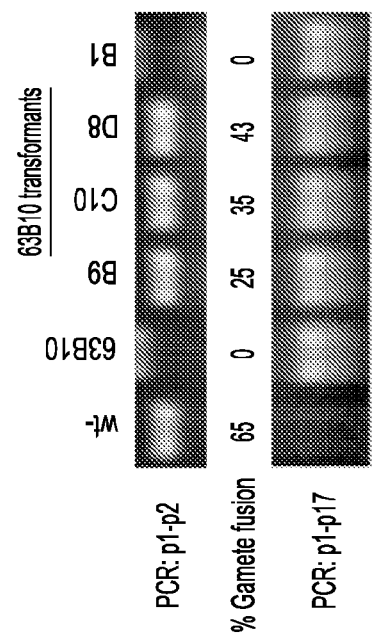
Figure 1E:
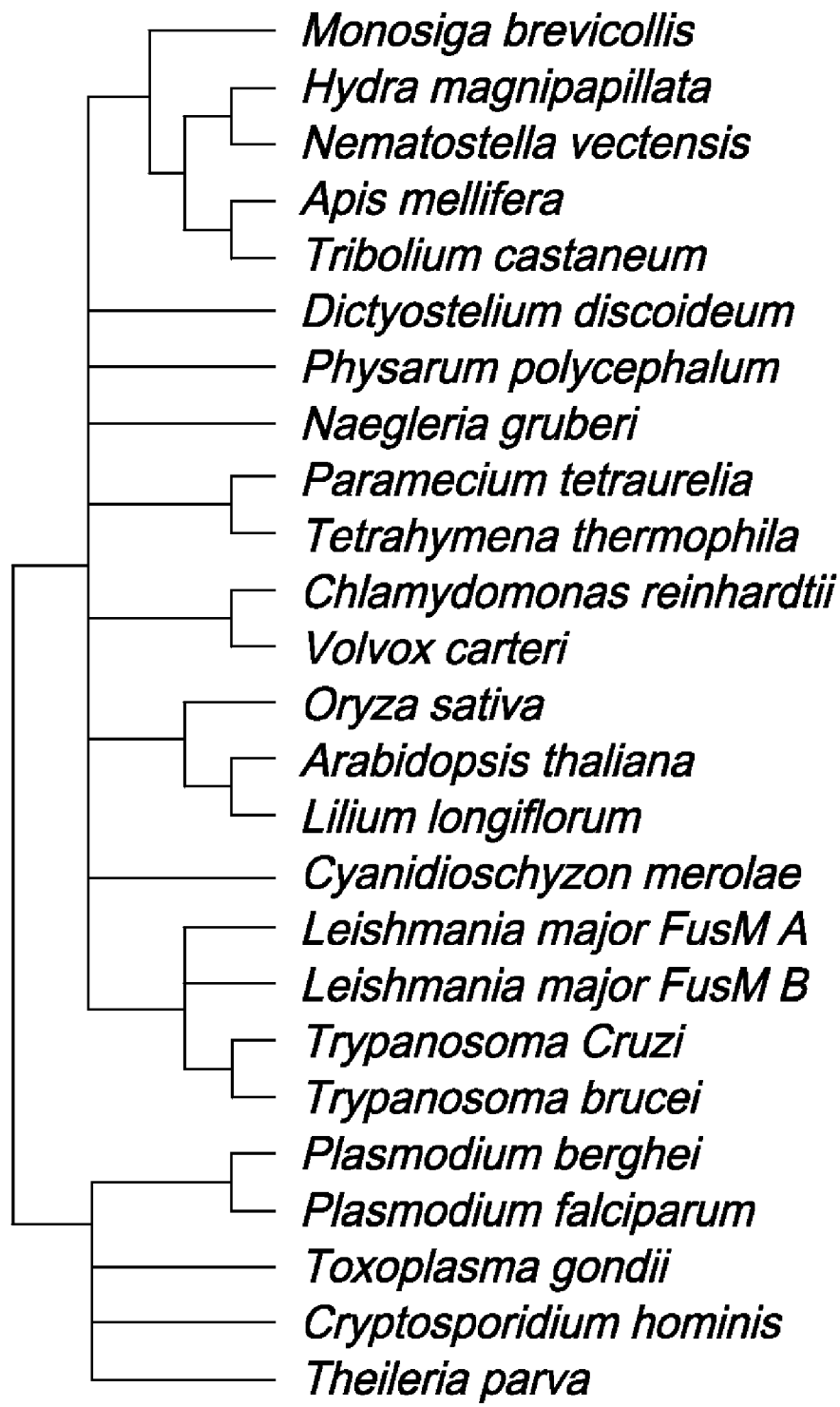
Figure 2A:
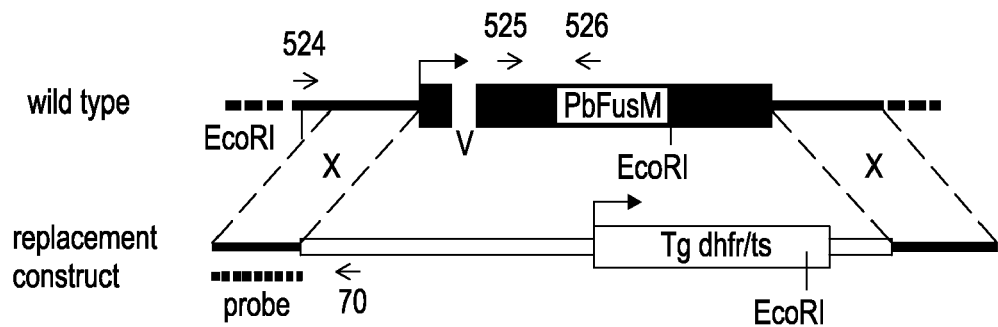
FIGS. 2A to 2F. FusM is essential for sexual development and mosquito transmission of *P. berghei*.
Figure 2B:
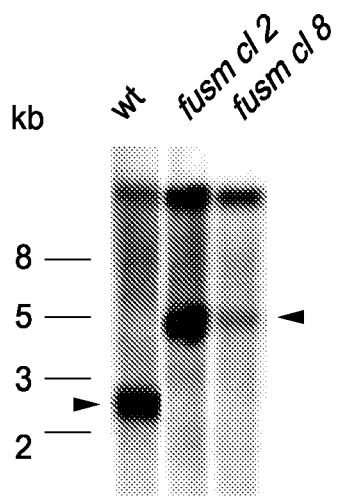
Figure 2C:
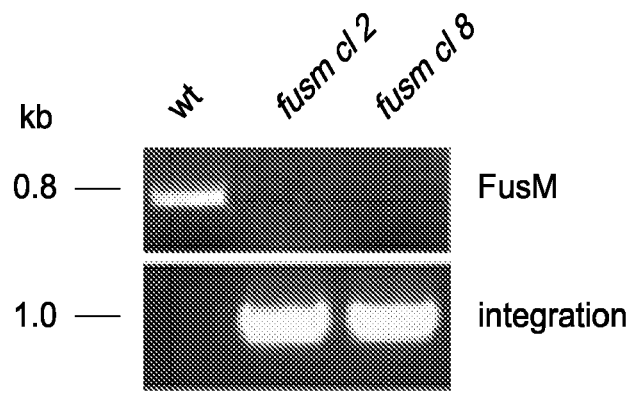
Figure 2D:
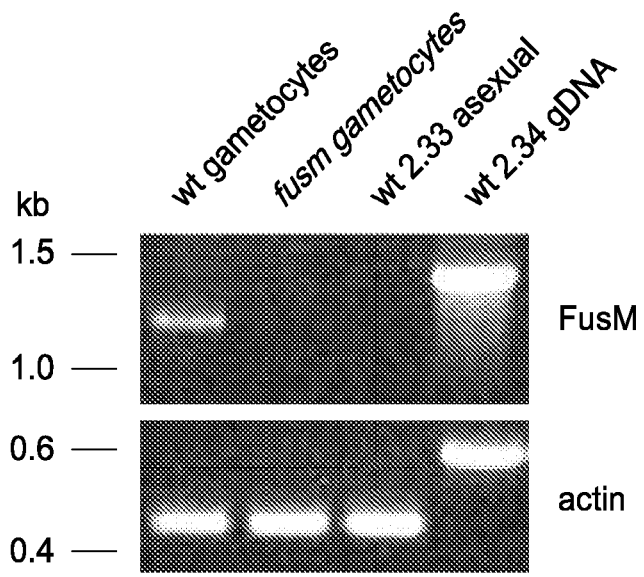
Figure 2E:
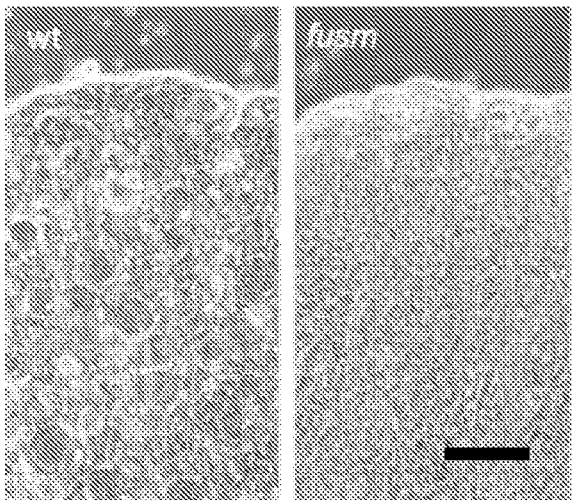
Figure 2E:
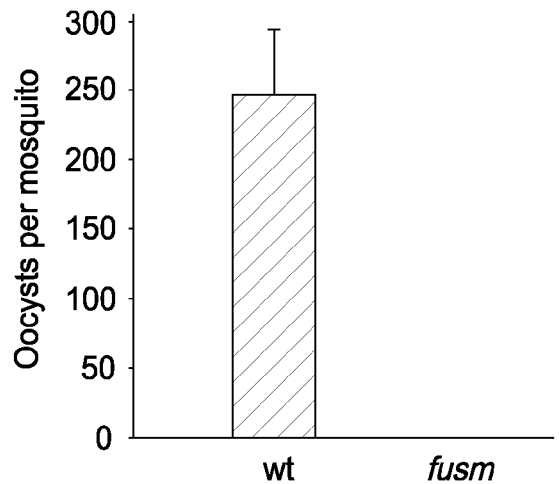
Figure 2F:
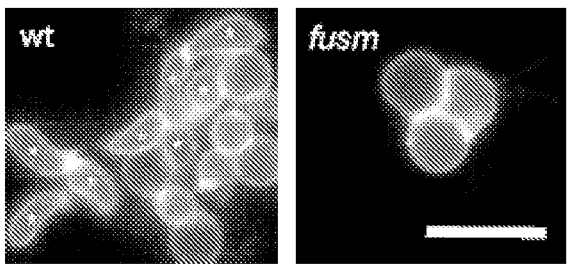
Figure 2F:
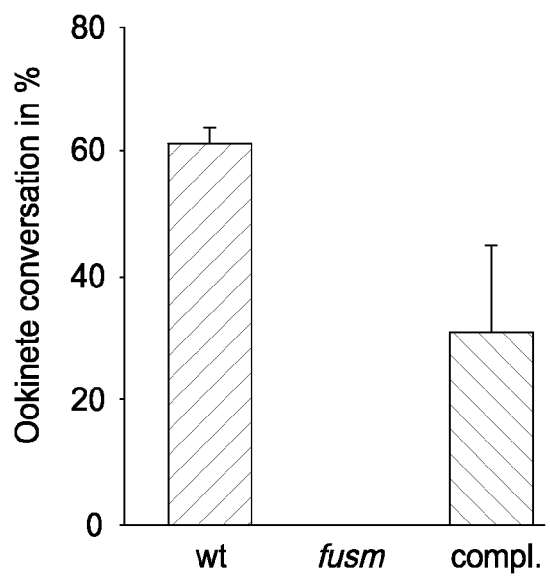

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A number of vaccines have a short shelf life and must be stored at refrigeration temperatures. Optimally, a vaccine should have a long shelf life when stored at room temperatures, however, live vaccines tend to require storage at cold temperatures (even when the vaccine is lyophilized), due to the fact that the number of viable vaccine units drops with prolonged storage at warmer temperatures. While killed or dead vaccines are more stable than live vaccines, live attenuated vaccines are more often used for intestinal vaccination due to the long-term, residual immunity that they provide and the low infectivity of the vaccine.

In general, only a few vaccines are administered orally, the only commonly used oral vaccine is the attenuated polio virus. While the attenuated virus may be killed by acid conditions in the stomach, the vaccine has been formulated in a manner that sufficient viable virus particles pass through the stomach to be active in the small intestine.

As used herein, the term "antigen" refers to a molecule with one or more epitopes that stimulate a host's immune system to make a secretory, humoral and/or cellular antigen-specific response against FusM (also known as HAP2 (Hapless 2) or GCS1 (generative cell specific 1)), or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof. For use with the present invention, one or more FusM antigens (native protein or protein fragment), may be provided directly or as part of a recombinant nucleic acid expression system to provide an antigenic FusM product to trigger a host immune response. The FusM antigen may further be a DNA molecule which produces the FusM antigen in the host.

As used herein, the term "gene" refers to a functional protein, polypeptide or peptide-encoding nucleic acid unit, e.g., the FusM encoding nucleic acids. As will be understood by those in the art, this functional term includes genomic sequences, cDNA sequences, probes, oligonucleotides or fragments thereof (and combinations thereof), as well as gene products, including those that may have been designed and/or altered by the user. Purified genes, nucleic acids, protein and the like are used to refer to these entities when identified and separated from at least one contaminating nucleic acid or protein with which it is ordinarily associated.

As used herein, the term "host cell" refers to cells that have been engineered to contain nucleic acid segments or altered segments, whether archeal, prokaryotic, or eukaryotic. Thus, engineered, or recombinant cells, are distinguishable from naturally occurring cells that do not have the recombinantly introduced genes. In one specific example of the present invention, the host cell has been modified by the introduction of exogenous nucleic acids that alter the expression of FusM, e.g., introduce a non-binding mutant of FusM. Alternatively, the host cell is a wild-type protozoan that has been mutated to express a mutant form of the FusM protein or to block the protozoan in a "mating state", e.g., a *Plasmodium* sp. that is non-pathogenic in humans that over-expresses the FusM and/or the FusM target for the vaccine of the present invention.

As used herein, the expressions "cell" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations for the type and source for a cell, e.g., protozoan, prokaryotic, etc., will be clear to those of skill in the art from the designation of the cell within the context of the discussion and the examples of the present invention.

As used herein, the term "plasmids" refers to extrachromosomal, at least partially self-replicating nucleic acids. Plasmids are designated by a lower case p preceded and/or followed by capital letters and/or numbers that name the plasmid. Many plasmids are commercially available, are publicly available on an unrestricted basis, or can be constructed from such available plasmids in accord with published procedures. In addition, other equivalent plasmids are known in the art and will be apparent to the ordinary artisan.

As used herein, the term "protein-protein complex" or "protein complex" refers to an association of more than one protein. The proteins of the complex may be associated by a variety of methods, or by any combination of methods, including but not limited to functional, stereochemical, conformational, biochemical, or electrostatic association. It is intended that the term encompass associations of any number of proteins.

As used herein, the terms "protein", "polypeptide" and "peptide" refer to compounds comprising amino acids joined via peptide bonds and are used interchangeably.

As used herein, the term "transformation," refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

As used herein, the term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells which transiently express the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "selectable marker" refers to the use of a gene that encodes an enzymatic activity and which confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. A review of the use of selectable markers in mammalian cell lines is provided in Sambrook, J., et al., Molecular Cloning: A Laboratory Manual, 2nd ed., Cold Spring Harbor Laboratory Press, New York (1989) pp. 16.9-16.15.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes or eukaryotes usually include a promoter, an operator (optional), and a ribosome binding site, often along with other sequences. Eukaryotic cells are known to use promoters, enhancers, and termination and polyadenylation signals. Another, and different, way in which the term "vector," is used herein refers to the insect or other host that serves to deliver a parasite between organisms, e.g., mosquitoes are common "vectors" for parasites that are transmitted between humans or animals via the mosquito "vector." Other vectors include, e.g., fleas, mites, flies and the like, as will be known to those of skill in the art. Finally, the term "vector" may be used to describe the use of a carrier or other delivery system or organism to deliver the antigen(s) of the present invention to a host in order to trigger an immune response as part of a vaccine. Non-limiting examples of these vaccine vectors include viruses, bacteria, protozoans, cells (e.g., homologous or heterologous), etc., which may be live, live-attenuated, heat-killed, mechanically-killed, chemically-killed, recombinant (e.g., peptides, proteins and the like), as will be known to those skilled in the art of vaccine preparation. The skilled artisan will readily recognize the type of "vector" to which this specification and claims refer based on the description of the materials and methods used and described herein.

As used herein, the term "amplify", when used in reference to nucleic acids refers to the production of a large number of copies of a nucleic acid sequence by any method known in the art. Amplification is a special case of nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer may be single stranded for maximum efficiency in amplification but may alternatively be double stranded. If double stranded, the primer is first treated to separate its strands before being used to prepare extension products. The primer must be sufficiently long to prime the synthesis of extension products in the presence of the inducing agent. The exact lengths of the primers chosen will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g. ELISA, as well as enzyme-based histochemical assays), fluorescent, radioactive, and luminescent systems. It is not intended that the present invention be limited to any particular detection system or label.

As used herein, the term "target" when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as DCTP or DATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

As used herein, the term "immunological response" refers to a composition or vaccine that includes a FusM antigen and that triggers in the host a cellular- and/or antibody-mediated immune response to FusM-derived antigens. Usually, such a response may include antibody production (e.g., in the intestinal tract, from germinal centers in lymph nodes, etc.), B cell proliferation, helper T cells, cytotoxic T cell proliferation, Natural Killer activation specifically to FusM antigen or antigens against the FusM target itself and/or fluids, secretions, tissues, cells or hosts infected therewith.

As used herein, the terms "vaccine composition" or "vaccine" refer to a FusM antigen that is used to stimulate the immune system of a vertebrate, e.g., a bird, a fish, a mammal, or even a human, so that current harm is alleviated, or protection against future harm is provided by an adaptive immune response. An immune response may also be provided passively, by transferring immune protection (e.g., antibodies) from one "immunized" host to the recipient that has not been challenged by the antigen and/or is unable to generate an immune response to the antigen. An immune response may also carry from the host into the vector, wherein the antibodies that are ingested by the vector along with the parasites block parasite mating.

As used herein, the term "immunization" refers to the process of inducing a continuing protective level of antibody and/or cellular immune response which is directed against a FusM antigen, either before or after exposure of the host to FusM.

As used herein, the term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

A nucleic acid having a sequence that is "substantially homologous" to a FusM antigen of SEQ ID NO:X is defined herein as an oligonucleotide sequence that exhibits greater than or equal to 75, 80, 85, 90 or 95% identity to the sequence of SEQ ID NO:X when sequences having a length of 20, 50, 100 bp or larger are compared. The equivalent term may be used to describe an amino acid sequence, that is, that a sequence may be "substantially homologous" at the amino acid level.

As used herein, the terms "altered", or "alterations" or "modified" refer to nucleic acid or amino acid sequences and includes changes such as insertions, deletions, substitutions, fusions with related or unrelated sequences, such as might occur by the hand of man, or those that may occur naturally such as polymorphisms, alleles and other structural types that lead to an antigenic or immunogenic peptide or protein that is substantially homologous or identical to a parasitic FusM. Alterations encompass genomic DNA and RNA sequences that may differ with respect to their hybridization properties using a given hybridization probe. Alterations of polynucleotide sequences for FusM, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

As used herein, the term "immunogen" refers to a antigen that is capable of initiating lymphocyte activation resulting in an antigen-specific immune response. An immunogen therefore includes any molecule which contains one or more epitopes that will stimulate a host's immune system to initiate a secretory, humoral and/or cellular antigen-specific response.

As used herein, the term "antibody" refers to polyclonal and monoclonal antibody preparations, as well as preparations including hybrid antibodies, altered antibodies, $F(ab')_2$ fragments, F(ab) fragments, Fv fragments, single domain antibodies, chimeric antibodies, humanized antibodies, and functional fragments thereof which exhibit immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments that exhibit immunological binding properties of the parent monoclonal antibody molecule.

Methods of making polyclonal and monoclonal antibodies are known in the art. Polyclonal antibodies are generated by immunizing a suitable animal, such as a mouse, rat, rabbit, sheep or goat, with an antigen of interest. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof. Rabbits, sheep, mice, rats, hamsters, horses, cows and goats are often used for the preparation of polyclonal sera when large volumes of sera are desired. These animals are good design choices also because of the availability of labeled anti-host antibodies. Immunization is performed by mixing or emulsifying the antigen in saline, preferably in an adjuvant such as Complete Freund's Adjuvant ("CFA") and injected. The animal is boosted 2-6 weeks later with one or more injections of the antigen in saline, often with the antigen emulsified with Incomplete Freund's adjuvant ("IFA"). Antibodies may also be generated by in vitro immunization, using methods known in the art. Polyclonal antisera is then obtained from the immunized animal.

Monoclonal antibodies are generally prepared using the method of Kohler and Milstein, Nature (1975) 256:495-497, or a modification thereof. Typically, a mouse, hamster, huMouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

As used herein, the terms "antigen-binding site" or "binding portion" refer to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

As used herein, the term "Fab'," refers to a polypeptide that is a heterodimer of the variable domain and the first constant domain of an antibody heavy chain, plus the variable domain and constant domain of an antibody light chain, plus at least one additional amino acid residue at the carboxy terminus of the heavy chain $C_H1$ domain including one or more cysteine residues. $F(ab')_2$ antibody fragments are pairs of Fab' antibody fragments which are linked by a covalent bond(s). The Fab' heavy chain may include a hinge region. This may be any desired hinge amino acid sequence. Alternatively the hinge may be entirely omitted in favor of a single cysteine residue or, a short (about 1-10 residues) cysteine-containing polypeptide. In certain applications, a common naturally occurring antibody hinge sequence (cysteine followed by two prolines and then another cysteine) is used; this sequence is found in the hinge of human $IgG_1$ molecules (E. A. Kabat, et al., Sequences of Proteins of Immunological Interest 3rd edition (National Institutes of Health, Bethesda, Md., 1987)). In other embodiments, the hinge region is selected from another desired antibody class or isotype. In certain preferred embodiments of this invention, the C-terminus of the $C_H1$ of Fab' is fused to the sequence Cys X X (X preferably is Ala, although it may be any other residue such as Arg, Asp, or Pro; one or both X amino acid residues may be deleted).

As used herein, the term "hinge region" refers to an amino acid sequence located between $C_H1$ and $C_H2$ in native immunoglobulins or any sequence variant thereof. Analogous regions of other immunoglobulins will be employed, although it will be understood that the size and sequence of the hinge region may vary widely. For example, the hinge region of a human $IgG_1$ is only about 10 residues, whereas that of human $IgG_3$ is about 60 residues.

As used herein, the term Fv refers to a covalently or non-covalently-associated heavy and light chain heterodimer which does not contain constant domains. As used herein, the terms "Fv-SH" or "Fab'-SH" refers to an Fv or Fab' polypeptide having a cysteinyl free thiol. The free thiol is in the hinge region, with the light and heavy chain cysteine residues that ordinarily participate in inter-chain bonding being present in their native form. In the most preferred embodiments of this invention, the Fab'-SH polypeptide composition is free of heterogenous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products.

As used herein, the term "humanized antibody" refers to an immunoglobulin amino acid sequence variant or fragment thereof that is capable of binding to a predetermined antigen and that includes an FR region having substantially the amino acid sequence of a human immunoglobulin and a CDR having substantially the amino acid sequence of a non-human immunoglobulin or a sequence engineered to bind to a preselected antigen.

As used herein, the term "control sequences" refers to DNA sequences necessary for the expression of an operably linked coding sequence in a particular host organism. The control sequences that are suitable for prokaryotes, for example, include a promoter, optionally an operator sequence, a ribosome binding site, and transcriptional terminators. Highly regulated inducible promoters that suppress Fab' polypeptide synthesis at levels below growth-inhibitory amounts while the cell culture is growing and maturing, for example, during the log phase may be used.

As used herein, a nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to e coding sequence if it is positioned so as to facilitate translation. Generally, "operably linked" means that the DNA sequences being linked are contiguous and, in the case of a secretory leader, contiguous and in same reading frame. Enhancers do not have to be contiguous. Linking is accomplished by ligation at convenient restriction sites. If such sites do not exist, then synthetic oligonucleotide adaptors or linkers are used in accord with conventional practice.

As used herein, the term "transgene" refers to such heterologous nucleic acid, e.g., heterologous nucleic acid in the form of, e.g., an expression construct (e.g., for the production of a "knock-in" transgenic animal) or a heterologous nucleic acid that upon insertion within or adjacent a target gene results in a decrease in target gene expression (e.g., for production of a "knock-out" transgenic animal). A "knock-out" of a gene means an alteration in the sequence of the gene that results in a decrease of function of the target gene, preferably such that target gene expression is undetectable or insignificant. Transgenic knock-out animals include a heterozygous knock-out of a target gene, or a homozygous knock-out of a target gene.

As used herein, the terms "Knock-out" and "conditional knock-out" refer to the alteration of a target gene that can be activated by exposure of the animal to a substance that promotes target gene alteration, introduction of an enzyme that promotes recombination at the target gene site (e.g., Cre in the Cre-lox system), or other method for directing the target gene alteration.

As used herein, the term "knock-in" refers to an alteration in a host cell genome that results in altered expression (e.g., increased or decreased expression) of a target gene, e.g., by introduction of an additional copy of the target gene, or by operatively inserting a regulatory sequence that provides for enhanced expression of an endogenous copy of the target gene. "Knock-in" transgenics include heterozygous knock-in of the target gene or a homozygous knock-in of a target gene and include conditional knock-ins.

The present invention is also directed to protein or peptide compositions, free from total cells and other peptides, which comprise a purified protein or peptide which incorporates an epitope that is immunologically cross-reactive with one or more anti-FusM antibodies.

The skilled artisan will recognize that epitopes may be mapped by simple deletion constructs that incorporate one or more epitope(s) that are immunologically cross-reactive with FusM. The peptide or protein antigen may include a primary, secondary or tertiary structure similar to an epitope located within the FusM polypeptide. The level of similarity will generally be to such a degree that monoclonal or polyclonal antibodies directed against the FusM polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of cytotoxic or helper T-cell-stimulating immunodominant epitopes against FusM, and/or their functional equivalents, may be suitable for use in vaccines. For example, the skilled artisan may employ the methods of Hopp (U.S. Pat. No. 4,554,101, relevant portions incorporated herein by reference), which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101, relevant portions incorporated herein by reference). The amino acid sequence of these "epitopic core sequences" may then be readily incorporated into peptides, either through the application of peptide synthesis or recombinant technology.

Peptides for T cell epitopes for use with the present invention will generally be on the order of 8 to 20 amino acids in length, and more preferably about 8 to about 15 amino acids in length. Depending on the Major Histocompatibility (MHC) of the host, shorter or longer antigenic cytotoxic of helper T-cell-stimulating peptides will provide advantages in certain circumstances, for example, in the preparation of vaccines or in immunologic detection assays. Exemplary advantages include the ease of preparation and purification, the relatively low cost and improved reproducibility of production, and advantageous biodistribution.

For example, synthetic peptides may be made that include modified and/or extended epitopic/immunogenic core sequences which result in a "universal" epitopic peptide directed to FusM. These epitopic core sequences are identified herein in particular aspects as hydrophilic regions of the FusM polypeptide antigen. It is proposed that these regions represent those which are most likely to promote T-cell or B-cell stimulation, and, hence, elicit specific antibody production.

The identification of epitopic core sequences is known to those of skill in the art, for example, as described by Hopp (U.S. Pat. No. 4,554,101, relevant portions incorporated herein by reference), which teaches the identification and preparation of epitopes from amino acid sequences on the basis of hydrophilicity. Moreover, numerous computer programs are available for use in predicting antigenic portions of proteins (see e.g., Jameson & Wolf, 1988; Wolf et al., 1988). Computerized peptide sequence analysis programs (e.g., DNAStar Software, DNAStar, Inc., Madison, Wis.) may also be useful in designing synthetic peptides in accordance with the present disclosure.

Synthesis of epitopic sequences or peptides that include antigenic epitopes within their sequence are readily achieved using conventional synthetic techniques such as the solid phase method (e.g., through the use of commercially available peptide synthesizer such as an Applied Biosystems ABI 433A Peptide Synthesizer). Peptide antigens synthesized in this manner may then be aliquotted in predetermined amounts and stored in conventional manners, such as in aqueous solutions or in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C. or frozen. Of course, where the peptides are stored in a lyophilized or powdered state, they may be stored virtually indefinitely, e.g., in metered aliquots that may be rehydrated with a predetermined amount of water (e.g., distilled) or buffer prior to use.

As used herein, the terms a "pharmacologic dose" or "therapeutically effective dose" refer to an amount sufficient to gives a desired physiological effect.

For oral therapeutic administration, the FusM antigen(s) may be incorporated with excipients and/or adjuvants and used in the form of ingestible tablets, buccal tables, troches, capsules, elixirs, suspensions, syrups, wafers, and the like. Such compositions and preparations should include at least 0.1% weight percent of the FusM antigen(s). The percentage of the compositions and preparations may, of course, be varied and may conveniently be between about 2 to about 60% of the weight of the unit. When targeting for mucosal immunity, the FusM antigen of the present invention may be provided along with any or a number of known vectors and/or carrier that produce a mucosal immune response, e.g., as taught by V. Gerdts, et al., Mucosal Delivery of Vaccines in Domestic Animals, Vet. Res. 37 (2006) 487-510, relevant portions incorporated herein by reference. The amount of the FusM antigen(s) may be selected and may be increased or decreased, as will be know to those of skill in the art of vaccination, depending on the therapeutically useful results of one or more vaccinations such that a suitable dosage will be obtained that is immunogenic, that is, it triggers an immune response.

The FusM antigen(s) may also be administered parenterally or intraperitoneally. Solutions of the FusM antigen(s) (or vectors that deliver the FusM antigen(s)) may be provided as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable, oral or other use include sterile aqueous solutions or dispersions and sterile powders for FusM vaccine delivery.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The FusM antigen(s) may be included for intramuscular, subcutaneous or even for transdermal administration and may include a reservoir adapted to retain during storage and release in operation the particles containing the FusM antigen(s) of the present invention. It will be appreciated that a wide variety of transdermal devices have been described in the art and are suitable for use in the present invention. An exemplary transdermal device generally includes a reservoir defined by an impermeable backing layer and a membrane. The backing layer and the membrane are joined together about the outer periphery of the device. These layers may be joined by an adhesive, a heat seal or the like. The transdermal device may also include an adhesive layer to attach the device to the skin of a subject. A release liner will generally cover the adhesive that the user removes prior to use of the device to expose adhesive layer.

Example 1

Identification of a family of protist plasma membrane proteins whose expression is restricted to male gametes and whose function is essential for the life cycle of parasitic protozoa. It has been found that FusM is a critical mating protein involved in the fusion of parasite gametes.

The present invention includes the identification of a novel family of cell surface gamete fusion proteins, named FusM, whose members are present in several species of parasitic protozoa. These proteins are critical for gamete fusion and have been targeted for the manufacture of a vaccine to prevent zygote formation. It is shown herein that the FusM family is a heretofore unrecognized candidate for transmission-blocking vaccines. FusM was found to be essential for gamete fusion in a related protist, the green alga, *Chlamydomonas reinhardtii*, an important model organism for investigating fertilization.

Using bioinformatics analysis and techniques, it was found that these proteins are conserved in parasitic protozoa. It is demonstrated herein that the parasitic protozoan FusM is critical for cell surface gamete fusion. FusM homologues are present in the following parasitic protozoa: *Plasmodium falciparum* and *Plasmodium vivax* (both responsible for malaria in humans), *Plasmodium berghei* (causative agent of rodent malaria)(the skilled artisan will recognize that all malaria species should include FusM, including *P. malariae* and *P. ovale*), *Trypansosoma brucei* subspecies (African Sleeping Sickness in humans), *Trypanosoma cruzi* (Chagas disease, a human disease in the Americas), *Cryptosporidium parvum* (Cryptosporidiosis in humans), *Eimeria tenella* (Coccidiosis in poultry), *Theileria* (Theileriosis, which causes heavy losses of ruminants in Africa, Asia, and Europe), and *Toxoplasma gondii* (Toxoplasmosis in humans). Previous studies reported that a FusM protein homolog (designated HAP2 [Johnson et al., 2004] or GCS1 [Mori et al., 2006]) was essential for fertilization in the mustard plant *Arabidopsis thaliana* but no functional results with the protein were shown beyond angiosperms.

The present inventors first demonstrated that *Chlamydomonas* FusM is essential for the final step in fertilization, fusion of the male with the female gamete of *Chlamydomonas* and that it is required only by male gametes. The inventors sought to disrupt the parasitic protozoan FusM. Using these parasitic protozoan FusM mutants it is demonstrated herein that FusM is essential in the male gamete for fusion of male and female gametes in *Plasmodium berghei*, a *Plasmodium* that infects mouse and that is used as a well-described and recognized model for the human form of malaria. In all *Plasmodium* species, fusion of male and female gametes to form zygotes is absolutely essential for transmission of the disease (through a mosquito) from one human to another. It was found that disruption of FusM function interferes with the life cycle of these organisms at the last step of gamete interactions, gamete fusion, and made it possible to develop anti-FusM vaccines that will interfere with transmission of devastating animal and human diseases.

It was found by the present inventors that the FusM protein is expressed by gametes in *Plasmodium* where its function in fertilization is essential for completion of the life cycle and transmission. It has been demonstrated that other proteins in this location can be successfully used as targets for vaccination (Quakyi et al., 1987; Milek et al., 1998). It has also been demonstrated that antibodies against proteins of analogous function in mammals block fertilization (Inoue et al., 2005). Antibodies or other molecular ligands that directly or indirectly interfere with FusM function will block the life cycle of the *Plasmodium*. Furthermore, the finding that FusM is essential for gamete fusion in two distantly related organisms, *Chlamydomonas* and *Plasmodium*, coupled with the presence of FusM family members in the Apicomplexans and Kinetoplastids, predict that FusM family members will have similar functions in these organisms. Thus, antibodies or other molecular ligands that directly or indirectly interfere with the function of FusM family members in the Apicomplexans and Kinetoplastids also have significant potential to block the life cycles of these organisms.

Discovery and characterization of FusM in the flagellated protozoa, *Chlamydomonas reinhardtii*. The molecular mechanisms that underlie the fusion of male and female gametes during fertilization in eukaryotes have been difficult to investigate. Until the report last year of the mouse sperm protein Izumo (Inoue et al., 2005), which does not have homologs in protists, only one other gamete fusion protein had been identified in any eukaryotic organism. That protein was Fus1 and it is required in female gametes for zygote formation in the unicellular green alga, *Chlamydomonas reinhardtii* (Ferris et al., 1996; Misamore et al., 2003). The mechanisms of gamete fusion are important to understand as part of the goal of identifying fundamental cellular and molecular mechanisms in fertilization that are common across species. Because the Fus1 gene is unique to *Chlamydomonas*, the present inventors isolated, characterized and identified the fusion protein in male gametes, anticipating that it would be more widely distributed in nature. Using insertional mutagenesis to randomly disrupt genes in the male strain of *Chlamydomonas* and bioassays to screen the mutants for cells whose gametes would recognize and become activated during interactions with female gametes but would be unable to fuse, the present inventors were able to identify the FusM protein. It was found that the gene FusM is essential for gamete fusion in *Chlamydomonas*. Moreover, its was found that FusM is a member of a gene family that is present in several parasitic protozoa that cause devastating human and animal diseases, including *Plasmodium*, the causative agent of malaria.

Materials and Methods. Culturing *Chlamydomonas*, mutagenesis, and screening for fusion mutants. Growth of *Chlamydomonas* vegetative cells and gametes, induction of gametogenesis, and assay of gamete adhesion, gamete activation and gamete fusion to form a zygote have been described previously (Pan and Snell, 2000). Insertional mutagenesis with a plasmid encoding a bacterially-derived paromomycin resistance gene was carried out as described (Pollock et al., 2003) using male strain B215. Over 6,000 insertional mutant clones that grew on paromomycin were analyzed. The clones were screened using phase contrast microscopy for cells that produced male gametes that could adhere to female gametes but were unable to fuse. One fusion-defective, insertional mutant clone, 63B10, was selected for further characterization.

Identification of the gene disrupted in fusion-defective clone 63B10. Genomic DNA from clone 63B10 was used as a template in TAIL PCR reactions to identify genomic DNA adjacent to the plasmid DNA that was used for insertional mutagenesis (Liu et al., 2005). The PCR product was cloned and sequenced using standard methods and contained 0.12 kb of genomic DNA. A BLAST search of version 2 of the Chlamydomonas genome database (genome.jgi-psf.org/chlre2/chlre2.home.html) showed that the 0.12 kb sequence was present in gene model C_530033. From a BAC clone containing this gene model, an 8.3 kb fragment was cloned that contained only gene model C_530033. To confirm that disruption of C_530033 indeed was responsible for the fusion-defective phenotype, a wild-type gene was introduced into the 63B10 mutant using co-transformation with the NIT gene (Kindle et al., 1989). Of 48 clones that grew on the selective medium, 4 clones produced gametes that were capable of gamete fusion (range=20-60% fusion). Using PCR methods it was shown that all 4 clones had received the wild-type gene, thereby confirming that C_530033 was essential for gamete fusion. The gene was named FusM, for fusion protein, male.

Expression of CrFusM transcripts is sex-specific and gamete-specific and essential for fusion in male gametes only. Analysis of genomic DNA showed that the FusM gene was not sex-linked but was present in both the male and female strains. To determine the pattern of expression of the gene, PCR methods were used. RT-PCR using mRNA isolated from wild-type male and female cells in the vegetative and gametic stages of their life cycle showed that FusM transcripts were present only in male gametes. In an independent approach, wild-type female gametes were crossed with a 63B10 male gamete that had been rescued for fusion with the wild-type FusM gene. Using PCR, the inventors screened for female progeny of meiosis that contained only the disrupted form of FusM. When mixed with wild-type male gametes, these FusM defective female gametes were fully capable of gamete fusion. Therefore, FusM is essential for fusion activity of only male gametes in Chlamydomonas.

CrFusM is not required for the initial steps in gamete interactions, including gamete recognition and gamete activation; it is essential only for gamete fusion. When male and female gametes of Chlamydomonas are mixed together they adhere to each other via their flagella. Flagellar adhesion triggers a complex flagellar signaling pathway within the flagella of each gamete that stimulates production of cAMP leading to activation of the gametes for cell fusion. The activated gametes release enzymes that degrade the extracellular matrix and both gametes reorganize fusogenic membrane specializations on their plasma membranes at the apical ends of the cell. Flagellar adhesion brings the fusogenic membranes into close contact, followed immediately by fusion of the plasma membranes of the two gametes. Within seconds the two gametes merge their cytoplasmic contents, reorient their flagella, and become a zygote (Goodenough, 1991). It was found that 63B10 gametes were incapable of gamete fusion. Next, the step in fertilization at which the blockage occurred was identified. By use of bright field and phase contrast microscopy, it was found that 63B10 male gametes underwent flagellar adhesion with wild-type female gametes that was indistinguishable from flagellar adhesion of wild-type male gametes. Bioassays that detect the presence of the extracellular matrix, showed that the 63B10 gametes also degraded their extracellular matrix when incubated with a cell-permeable form of cAMP or when mixed with wild-type female gametes, thereby demonstrating that they were capable of gamete activation. Moreover, addition of the membrane-permeable form of cAMP to 63B10 gametes adhering to wild-type female gametes did not rescue gamete fusion. Therefore, FusM was dispensable for gamete adhesion and gamete activation, and was essential only for fusion of the plasma membranes of the interacting gametes.

FusM family members are present in higher plants, primitive multicellular animals, and parasitic protozoa, including Plasmodium. By use of bioinformatics methods, including BLAST searches, FusM family members in Oryza sativa (rice), Zea mays (corn) and most other higher plants whose genomes are publicly available were also identified. FusM family members were also identified in Hydra and the Startlet Sea Anemone, but not in other multicellular animals to date. FusM is present in many non-parasitic unicellular protozoa, including Tetrahymena thermophila and Dictyostelium discoideum. Finally, FusM family members are present in many parasitic protozoa, including Plasmodium falciparum, Plasmodium vivax, Plasmodium berghei, Trypansosoma brucei, Trypanosoma cruzi, Cryptosporidium hominis, Eimeria tenella, Theileria parva, and Toxoplasma gondii. FIG. 1 shows an alignment of the sequences of FusM family members in several of these parasitic protozoa, SEQ ID NOS, 1-10, respectively.

TABLE 1

Properties of FusM mutants of Chlamydomonas and Plasmodium

| Organism | Asexual growth | Gametogenesis | Initial gamete interactions | Female gamete fusion | Male gamete fusion | Zygote maturation |
|---|---|---|---|---|---|---|
| Chlamydomonas | Wild type phenotype | Wild type phenotype | Wild type phenotype | Wild type phenotype | None | None |
| Plasmodium | Wild type phenotype | Wild type phenotype | Wild type phenotype | Wild type phenotype | None | None |

The Plasmodium FusM is a microgamete (male gamete) fusion protein. Although several important cellular and molecular events of the sexual phase of the life cycle of Plasmodium have been elucidated, the proteins that accomplish gamete interactions and gamete fusion have not been identified. Fertilization in Plasmodium occurs in the gut of mosquito after it has ingested the blood of an infected host. Once in the environment of the mosquito gut, male gametocytes (microgametocytes) and female gametocytes (macrogametocytes) within the red blood cells of the ingested blood meal are released from the cells and are stimulated to undergo gametogenesis to form male gametes (microgametes) and female gametes (macrogametes), events that are completed within 10-15 minutes. The male gametes possess a single flagellum which they use for propulsion. Upon collision with a female gamete (which is immotile), the male gamete adheres transiently and then fuses with the female gamete to become a zygote. The zygote elongates to become an ookinete, which migrates through the wall of the gut where it becomes an oocyst. Further meiotic and mitotic divisions eventually produce sporozoites that migrate to the salivary gland from which they are injected into a new host at the next feeding, thereby transmitting the disease (Sinden, 1983). To identify a possible role for FusM in Plasmodium sexual reproduction, molecular methods were used to disrupt the Plasmodium FusM gene. It was found that the FusM protein is essential for fusion of male and female gametes in Plasmo-

*dium berghei* (FIG. 2). Thus, as predicted from the results in *Chlamydomonas*, interference with the *Plasmodium* FusM gene blocks the sexual life cycle of this deadly protozoan parasite.

Generation of a *Plasmodium* mutant clone containing a disrupted FusM gene. Using an established method for generation of gene targeting constructs in *Plasmodium berghei* (Menard and Janse, 1997), a strain was produced in which the FusM gene (PbFusM) was disrupted. Subcloning using standard methods followed by PCR analysis confirmed the absence of the wild-type gene.

The FusM mutant *Plasmodium* strain exhibited no detectable phenotype in the asexual phases of its life cycle, but the mutant gametes failed to fuse and failed to produce ookinetes. Blood from mice infected with the FusM mutant strain was incubated in vitro under conditions that stimulated release of microgametes and macrogametocytes from red blood cells (Billker et al., 1998). Examination of the samples by light microscopy revealed that macrogametocytes underwent exflagellation and produced flagellated microgametes whose morphology and motile properties were indistinguishable from wild-type cells.

In addition, the mutant macrogametes exhibited wild-type morphology. Analysis by light microscopy, however, indicated that the male gametes exhibited a non-wild-type interaction with the female gametes. Whereas wild-type gametes approached the female, briefly interacted, and then merged with the female, no merging of the cells could be detected in the mutant cultures. Furthermore, analysis of the cultures 24 hours after beginning of the incubation utilizing an immunofluorescence assay (Winger et al., 1988) demonstrated that no ookinetes had formed. And, finally, examination of the midguts of female *Anopheles* mosquitoes that had fed on mice containing wild-type and FusM mutant forms of *Plasmodium*, revealed that only mosquitoes that had fed on wild-type mice contained *Plasmodium* oocysts. Mosquitoes that had fed on the mice containing *Plasmodium* whose FusM gene was disrupted did not contain any oocysts. Thus, based on multiple, well-accepted scientific criteria, FusM was found to be essential for zygote formation in *Plasmodium*. Therefore, FusM is a critical target for vaccination.

FusM is essential only in male gametes. Since both the male and female gametes produced by the mutant strain possessed the disrupted FusM gene, additional studies were carried out to determine whether FusM was required in the male or female gamete or both. Blood containing the FusM mutant strain was mixed with blood from a mutant strain incapable of producing male gametes (Billker et al., 2004) or with blood from a mutant strain incapable of producing female gametes (Reininger et al., 2005). Analysis of the samples showed that when FusM mutant samples were mixed with blood from a mutant that produced only female gametes, no ookinetes were formed. On the other hand, when FusM mutant samples were mixed with blood from a mutant that produced only male gametes, ookinetes were formed. These results indicated that FusM mutant female gametes were capable of fusion, whereas FusM mutant male gametes were incapable of fusion. Thus, FusM is essential only in the male gamete.

Example 2

Unlike FUS1, which is species-specific (13, 16), FusM is widely conserved and contains no previously described domains. Mori et al. had reported that in addition to its presence in higher plants (including rice), database searches showed homologs in *Chlamydomonas* and red algae, a slime mold, and *Plasmodium* and *Leishmania*. Using PSI-BLAST the family was expanded, finding members in many other non-pathogenic and pathogenic protists, and importantly in multicellular animals including hydra and sea anemone (7). The presence of FusM in protists, higher plants, and some metazoans is in marked contrast with the rapid evolution of other genes involved in gamete interactions (16, 17). It was then determined whether the function of FusM in fertilization was conserved between *Chlamydomonas* and malaria parasites (genus *Plasmodium*), whose transmission to the mosquito relies on sexual reproduction. Sexual precursor stages, the gametocytes, form in the vertebrate host inside infected erythrocytes but remain quiescent until ingested by a susceptible *Anopheles* mosquito. In the bloodmeal, gametocytes emerge from their host cells and within minutes differentiate into gametes. Each female (macro) gametocyte gives rise to a single immotile macrogamete, while microgametocytes generate up to eight flagellated microgametes in a process termed exflagellation; within minutes after release, the gametes meet, adhere tightly for a few seconds, and then fuse to form a zygote (18). Microgamete adhesion to macrogametes requires the surface protein and transmission-blocking vaccine candidate P48/45 (19). Its role in microgamete adhesion may be direct or indirect, since P48/45 is known to interact physically with at least one other microgametocyte protein, P230 (20) and in *P. falciparum* is required to retain the complex on the surface of the microgamete (21). Within 15-20 h the zygote transforms into a motile ookinete, which penetrates the midgut epithelium and establishes the infection in the mosquito by forming an oocyst between the midgut epithelial cells and their underlying basal lamina. Thus, gamete adhesion and fusion are obligate steps in transmission and attractive targets for transmission-blocking vaccines. In the rodent malaria parasite *P. berghei*, gametocytes respond efficiently to well-characterized developmental triggers (22) in vitro, and gametogenesis, fertilization and ookinete formation are accessible to analysis in culture.

Targeted deletion of *P. berghei* FusM (GenBank accession number XM_671808) resulted in two knock-out clones (FIG. 2, A-C). RT-PCR detected FusM transcripts in wt gametocytes, but not in fusm gametocytes or in wt asexual erythrocytic stages of a gametocyte-deficient parasite strain (FIG. 2D). Consistent with this sexual stage-specific transcription, fusm clones showed normal asexual intraerythrocytic parasite development in mice. Neither the rate of gametocyte formation nor the sex ratio were affected (data not shown), but mosquitoes that had fed on mice infected with fusm parasites failed to develop oocysts on their midguts (FIG. 2E). The complete block in malaria transmission in vivo correlates with the absence of formation of ookinetes (FIG. 2F) in vitro, a process that occurs efficiently in wt parasites. Genetic complementation of the *P. berghei* fusm mutant restored ookinete formation. Thus, results in both *Chlamydomonas* and *Plasmodium* pointed to a role for FusM in fertilization.

Figure 3A:
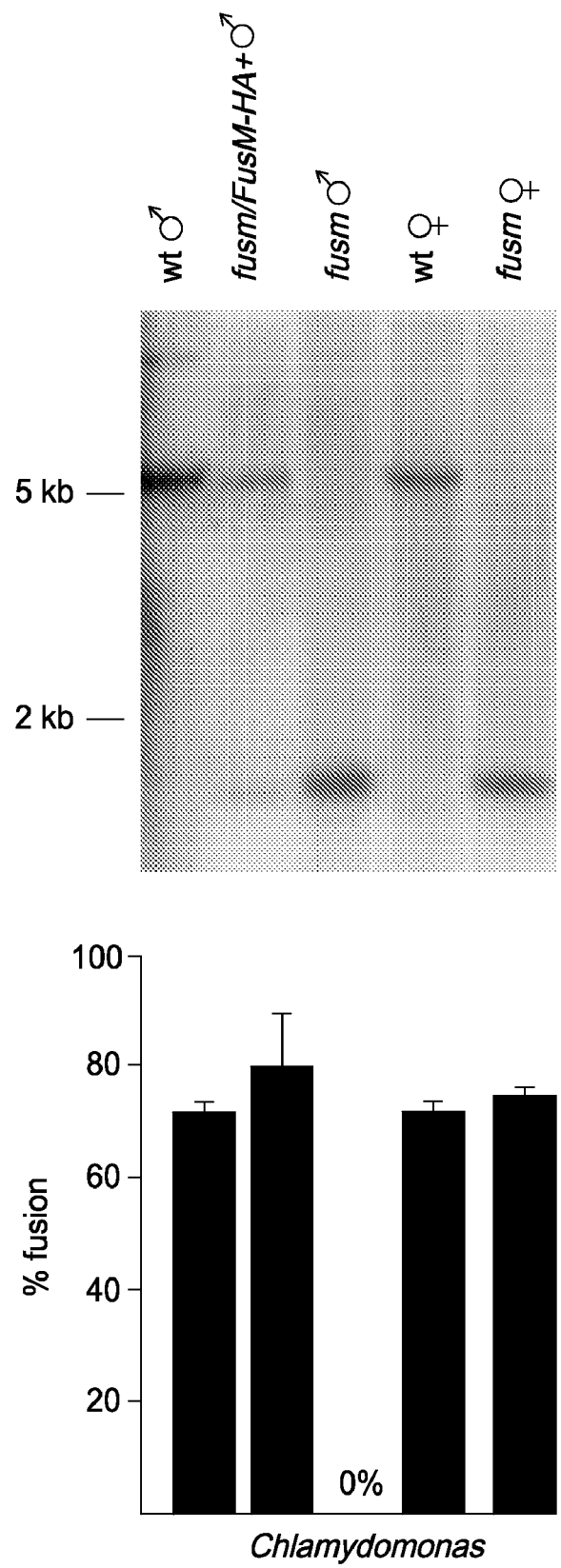
Figure 3B:
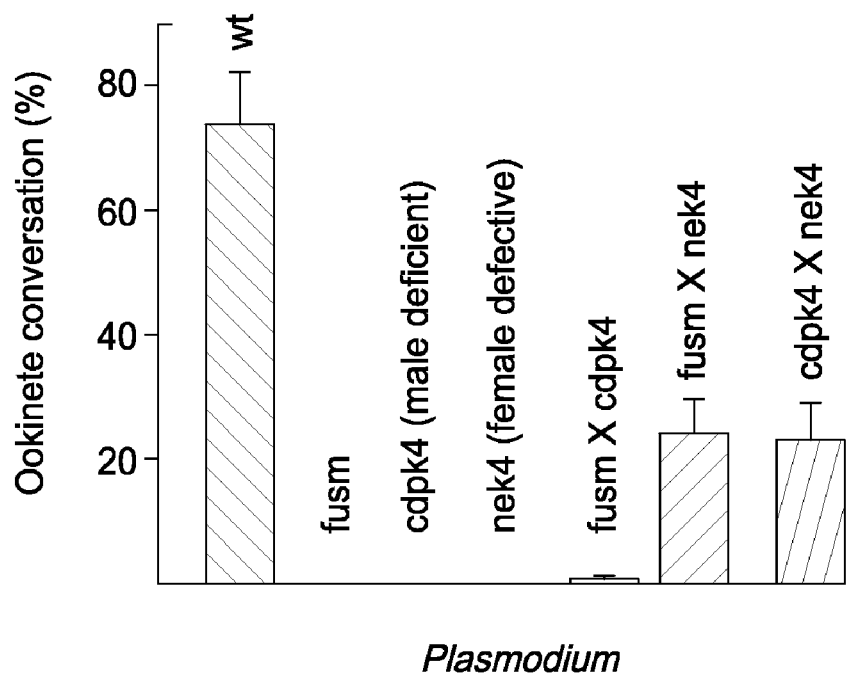

To dissect the function of FusM in *Chlamydomonas* fertilization, it was next determined whether FusM is required in male or female gametes or both. Briefly, wt females were crossed with 63B10 males that had been rendered fusion-competent by transformation with the wild type FusM gene, and selected female progeny that contained only the disrupted FusM gene (Southern blot, FIG. 3A, upper panel). Female gametes that lacked a functional FusM gene exhibited no detectable mutant phenotype as vegetative cells or gametes and underwent gamete fusion similarly to wt (FIG. 3A, lower panel). Consistent with results of Mori et al. (7) a strong RT-PCR signal for FusM in male gametes of *Chlamydomonas* and low amounts in female gametes was detected, although it was also detected in low amounts in male vegetative cells (data not shown). Thus, in spite of the detection of FusM transcripts in females, FusM is essential in fusion of *Chlamydomonas* male gametes only. In malaria parasites, gender-specific sterility phenotypes are revealed in cross-fertilization experiments with known sexual development mutants, such as the male-deficient cdpk4 or the female-defective nek4 mutant (23, 24). Neither cdpk4 nor nek4 strains produced ookinetes when cultured on their own, but when gametocytes of both mutants were mixed, nek4 microgametes productively fertilized cdpk4 macrogametes, restoring the capacity to form ookinetes (FIG. 3B). The fusm mutant was successfully cross-fertilized by nek4 male gametes, showing that fusm macrogametes were fusion competent. Taken together these results demonstrate that during fertilization in both *Chlamydomonas* and *Plasmodium* FusM is essential in male gametes only.

Figure 3C:
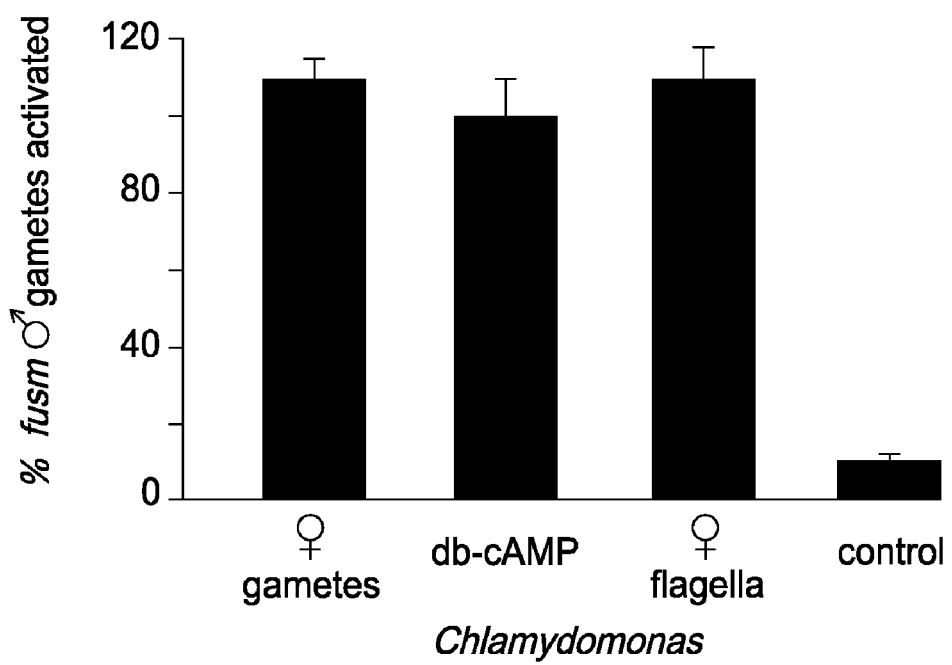

Unlike many organisms whose gametes possess an extracellular matrix that must be removed before fusion, *Plasmodium*'s gametes are "naked" (18). Therefore, it was determined whether FusM would also function at a step in *Chlamydomonas* fertilization when the gametes are "naked," that is, after flagellar-adhesion-induced gamete activation and release of cell walls. Consistent with this prediction, in mixtures of wt females and 63B10 male gametes, flagellar adhesion led to activation of both gametes as assessed by wall loss (FIG. 3C) and activation of female mating structures (not shown). 63B10 gametes also responded to the activation-triggering agent, db-cAMP, by releasing their walls (FIG. 3C). Because our results pointed to a role for FusM late in gamete interactions, possibly at the site of membrane fusion, the properties of FusM in 63B10 gametes expressing an HA-tagged FusM were investigated. Immunoblotting (FIG. 3D) showed that FusM-HA was expressed only in gametes. The detection of two closely spaced isoforms of FusM-HA suggested that the protein undergoes posttranslational modification. The more slowly migrating form disappeared upon treatment of live cells with trypsin, indicating that one form of FusM is exposed on the external surface of gametes (FIG. 3E). Moreover, immunofluorescence imaging showed that FusM was present as a single spot near the bases of the two flagella, the location of the mating structure (FIG. 3F) (11). Thus, the topology and the location of FusM were consistent with a function in either adhesion or fusion at the fusogenic plasma membrane sites.

Figure 4A:
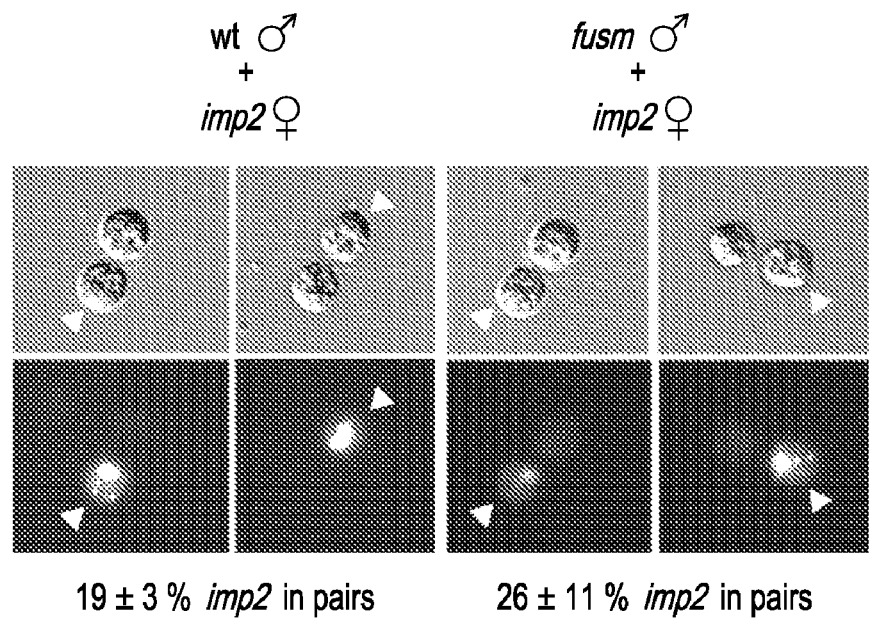
FIGS. 4A to 4C. FusM functions in the gamete fusion reaction downstream of gamete membrane adhesion.
Figure 4B:
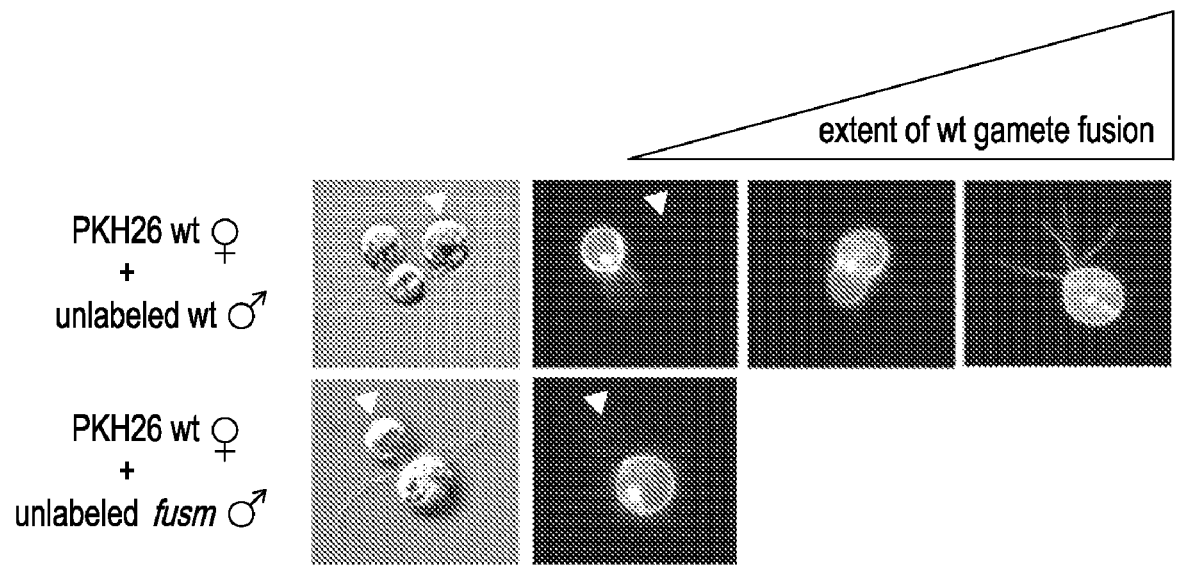

To examine the adhesion properties of the fusogenic membrane on 63B10 gametes without the interference of flagellar adhesion, 63B10 gametes were activated with db-cAMP and mixed them with similarly activated imp2 female gametes, which do not possess flagellar adhesion molecules. Surprisingly, the 63B10 males adhered tightly to the female gametes at the site where fusion normally occurs (FIG. 4A, right two panels), in a manner indistinguishable from adhesion of wild-type (wt) males and females at the site of fusion (13) (FIG. 4A, left two panels). Although the absence of zygote aggregates in 63B10/wt mixtures (FIG. 1D) demonstrated that cytoplasmic mixing of the two gametes and the consequent activation of the zygote developmental pathway (26) required FusM (26), it was possible that the 63B10 gametes underwent membrane fusion, and that FusM functioned after gamete membranes began to merge. Studies designed to assess membrane merger as detected by movement of a fluorescent lipid (PKH26) from the plasma membranes of labeled female gametes to wt and mutant males, however, ruled out this latter possibility. Whereas lipid mixing between wt females and wt males was evident soon after the mating structures interacted and complete mixing occurred immediately thereafter (FIG. 4B, upper panels), membrane merger was never detected in the hundreds of 63B10 male/wt female pairs examined in several independent experiments (FIG. 4B, lower panels). Taken together, these results demonstrated that male gametes employ a protein different from FusM to bind to the female-specific, mating structure adhesion protein FUS1, and that FusM is essential at a step in the gamete membrane fusion reaction immediately after species-specific adhesion of the fusogenic membranes.

Figure 4C:
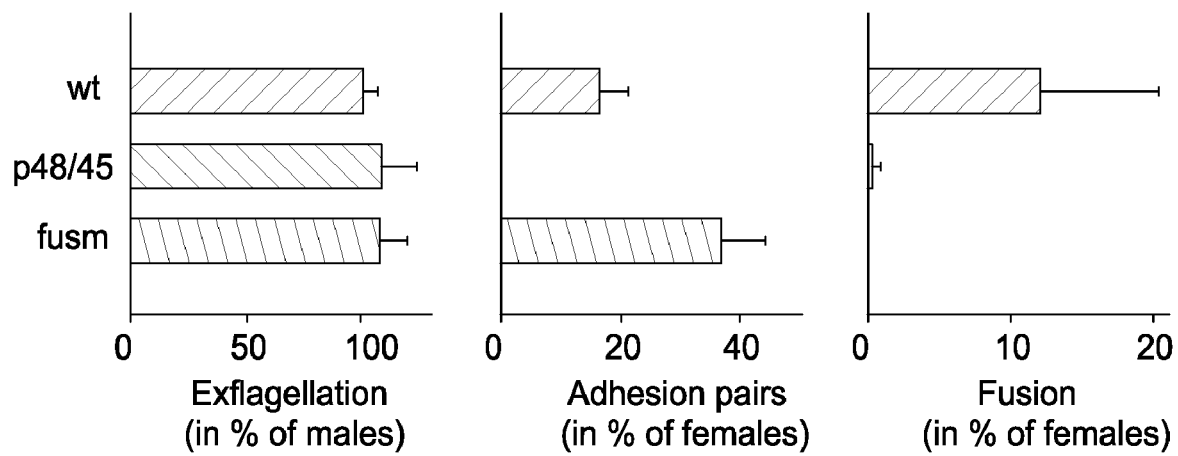

Similarly, FusM functions downstream of gamete adhesion in *Plasmodium*. Microscopic examination of fertilization in vitro showed that in the absence of FusM the incidence of male/female *Plasmodium* gamete pairs was approximately doubled compared to wild type (FIG. 4C); the failure to detect fertilization indicated that fusm pairs formed and persisted, but failed to progress from adhesion to membrane fusion. In marked contrast, in fertilization experiments with a p48/45 mutant, a complete lack of gamete binding explained fully the absence of fertilization (FIG. 4C), confirming the importance of the *Plasmodium*-specific P48/45 (19) complex in gamete adhesion.

The FusM mutants in *Chlamydomonas* and *Plasmodium* were used to genetically dissect the membrane fusion reaction in both species into molecularly distinct events of membrane adhesion and membrane fusion. Whether FusM functions directly as a fusogen, or has a more indirect role in the seconds between adhesion and fusion, may be determined. Membrane fusion reaction mechanisms are infrequent during evolution and the conserved function of FusM in gamete membrane fusion in two widely disparate organisms is consistent with a direct role for FusM in the final event of fertilization. Viruses use a single protein for both specific contact and for fusion itself, and the several classes of viral fusion proteins apparently evolved independently (4). Intracellular vesicle fusion employs distinct sets of conserved protein families for each step—rabs and their effectors for specific adhesion, and SNARES for membrane merger (1). These results show that the gamete membrane fusion reaction likewise depends on separate sets of proteins for specific adhesion and for fusion per se. In this manifestation of fusion, however, membrane adhesion depends on species-limited proteins, such as FUS1, possibly reflecting their roles in speciation, whereas membrane merger depends on the broadly conserved FusM protein family. The obligate role of zygote formation in malaria transmission and the apparently strong selective pressure against mutations in FusM make it a potential target for transmission-blocking malaria interventions.

Example 3

Vaccination and production of antibodies against *Chlamydomonas* FusM protein. Expression and purification of recombinant FusM protein. Bacterial expression plasmid PYJ61 containing FusM cDNA (see below) was transformed into M15 bacteria strain for expression of His-tagged FusM recombinant protein. Protein production and purification were carried out as follows: 10 ml of overnight bacteria culture were inoculated into 1 liter LB broth media with 100 ug/ml of Ampicillin. After shaking for 1 hr at 37° C., the culture was induced with 0.1 mM IPTG for 3 hrs at 37° C. ($OD_{600}$=0.6). Bacteria were harvested by centrifugation and suspended in 10 ml lysis buffer (20 mM Tris, 300 mM NaCl, 10 mM imidazole, protease inhibitor cocktail from Roach). Cell lysate were added with lysozyme to 1 mg/ml and incubated for 30 min on ice. 1.5% Sarkosyl (final concentration) was added to the lysate and the lysate was sonicated for 5 min. After sonication, the lysate was centrifuged at 12,000 g for 30 min. Triton-X-100 (final concentration 2%) was added to the supernatant, which was then passed through a 1 ml Ni-NTA affinity column (Qiagen). For maximum binding of protein, the lysate was incubated with Ni-NTA affinity beads for 1 hr. The column was washed with 50 ml wash buffer (20 mM imidazole, 20 mM Tris, 300 mM NaCl, 1% Triton, protease inhibitor cocktail). Bound recombinant protein was eluted with 10 ml elution buffer (20 mM Tris, 300 mM NaCl, 1% Triton, 250 mM imidazole, protease inhibitor cocktail). Eluted proteins were separated by SDS-PAGE. Recombinant FusM protein (75 Kd) was excised from the SDS-PAGE gel slice and electro-eluted for injection into animals.

CrFusM protein was affinity purified on an Ni-NTA column followed by SDS-PAGE. Coomassie stain shows the predominant band of CrFusM recombinant protein that runs as a 75 Kd protein (data not shown).

Vaccine production, immunization and antibody production and purification for immunoblotting and bioassays for gamete fusion. Rabbits were immunized with recombinant FusM protein using standard methods. Briefly, recombinant FusM protein purified as described and resuspended in phosphate buffered saline, was mixed with Freund's Complete adjuvant, final concentration of protein 1 mg/ml. After emulsification, the sample 0.5 ml was injected into a rabbit according to protocols approved Institutional Animal Care and Use Committee (IACCUC), subcutaneously in the flank. After 2-3 weeks the animals were boosted with 0.5 mg antigen in Freund's Incomplete Adjuvant subcutaneously. After 3 boosts over the course of 3 months, blood was collected from an ear vein by venous puncture using approved protocols. To prepare serum, the blood was allowed to clot, and the serum collected. Antibodies were affinity purified from the serum. Ten ml rabbit antiserum prepared against recombinant FusM protein was passed over a 2 ml protein A agarose antibody affinity column. The column was washed with 50 ml PBS, antibody was eluted with 10 ml 0.1M glycine (pH2.0) and antibody concentration was determined by absorbance at 280 nm. For gamete fusion bioassays, the purified antibody was dialyzed against 1 liter PBS or M-N media (nitrogen free media for *Chlamydomonas*). Antibody was stored at 2-8° C. with 0.2% sodium azide. For gamete fusion blocking experiments, no azide added.

Figure 5:
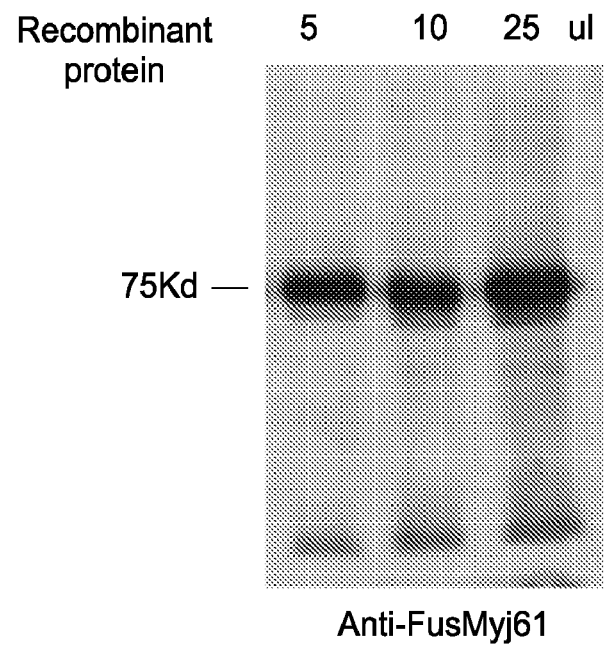
FIG. 5 shows the results of vaccination using the CrFusM antigen. Purified antibody against CrFusM stains recombinant FusM protein efficiently on immunoblots. Recombinant CrFusM protein was purified with Ni-NTA affinity column and loaded with increasing amounts on SDS-PAGE.

FIG. 5 shows that the vaccine was able to trigger a specific immune response. Purified antibody against CrFusM stains recombinant FusM protein efficiently on immunoblots. Recombinant CrFusM protein was purified with Ni-NTA affinity column and loaded with increasing amounts on SDS-PAGE.

Figure 6:
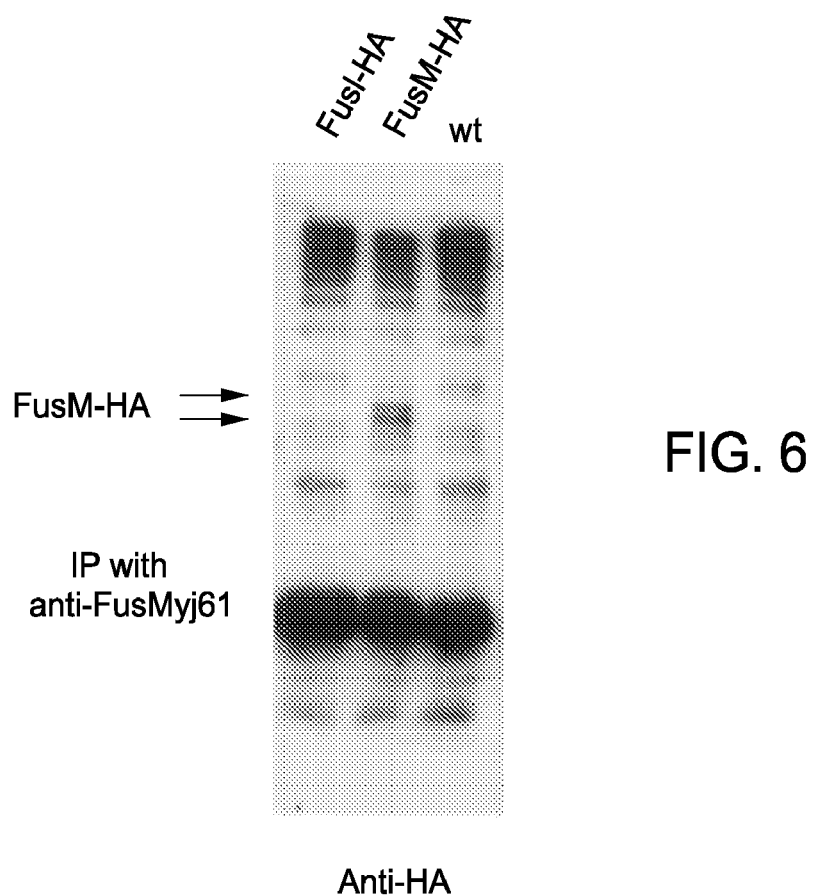
FIG. 6 the vaccine generated an immune response. Immunoblots show that purified anti-CrFusM antibodies immunoprecipitate endogenous FusM-HA protein. *Chlamydomonas* gametes of wild-type strain (wt) or strains expressing Fus1-HA (HA tagged Fus1 protein, a negative control) or FusM-HA were lysed and used for immunoprecipitation assay. Lysates were immunoprecipitated with purified anti-CrFusM antibodies and the immunoprecipitates were stained with anti-HA monoclonal antibody (Roach) on immunoblots. Only FusM-HA protein was immunoprecipitated by anti-CrFusM antibodies (two isoforms of FusM-HA shown with two arrows) and not Fus1-HA.

FIG. 6 demonstrates the specificity of the immune response by immunoblots show that purified anti-CrFusM antibodies immunoprecipitate endogenous FusM-HA protein. *Chlamydomonas* gametes of wild-type strain (wt) or strains expressing Fus1-HA (HA tagged Fus1 protein, a negative control) or FusM-HA were lysed and used for immunoprecipitation assay. Lysates were immunoprecipitated with purified anti-CrFusM antibodies and the immunoprecipitates were stained with anti-HA monoclonal antibody (Roach) on immunoblots. Only FusM-HA protein was immunoprecipitated by anti-CrFusM antibodies (two isoforms of FusM-HA shown with two arrows) and not Fus1-HA.

Anti-FusM antibodies for inhibition of gamete fusion. The vaccine was able to produce a FusM antigen-specific immune response that was able to block gamete formation. Briefly, Activated male ($5\times10^6$ cells/ml in M-N) were incubated with purified anti-recombinant FusM antibodies at 0.5, 1, 2.5 mg/ml final concentration for 1 hr, the treated gametes were mixed with an equal number of female gametes, and at 4 min after mixing the extent of gamete fusion was determined. As is indicated in the table below, antibody treatment in these initial experiments reduced fusion to 48% of the control cells (52% inhibition).

TABLE 2

Inhibition of gamete fusion by anti-FusM antibody

| Antibody concentration (mg/ml) | Gamete fusion (percent of control) |
| --- | --- |
| 0 (control) | 100% |
| 0.5 | 66% |
| 1 | 61%) |
| 2.5 | 48%) |

Figure 7:
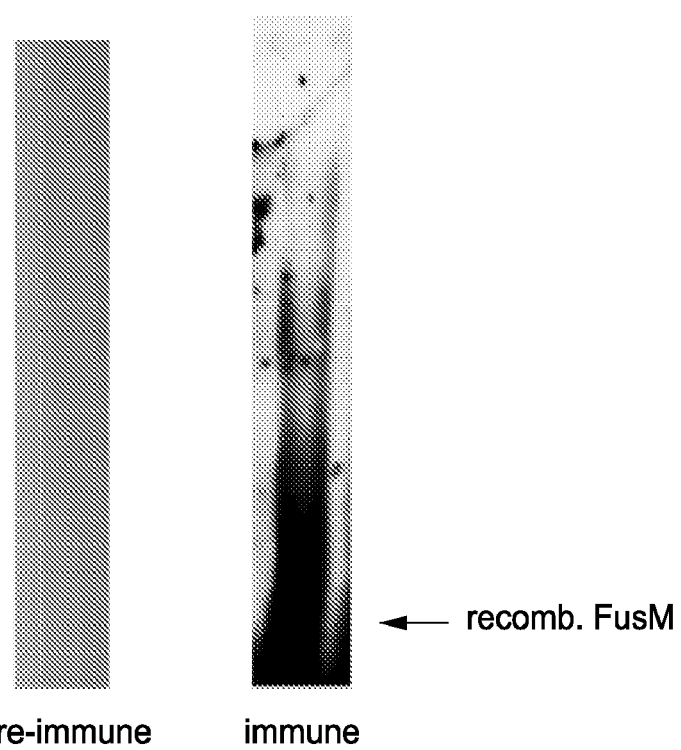
FIG. 7 shows the results of vaccinating a mouse. Immunoblots show that antiserum from mice injected with FusM protein for monoclonal antibody production recognizes recombinant CrFusM protein.

FIG. 7 shows the vaccination result from immunizing a different mammal. Immunoblots show that antiserum from mice injected with FusM protein for monoclonal antibody production recognizes recombinant CrFusM protein.

Example 4

Heterologous expression of *P. berghei* FusM in *E. coli* based expression systems. The FusM gene in *P. berghei* (locus PB-RP1579) consists of an open reading frame 2696 bp long, containing two exons, and an intron 209 bp long, located at position +228 within the gene. This gene encodes a protein 828 amino acids in length, with a single predicted transmembrane domain between residues 680 and 708, towards the C-terminus of the polypeptide. No other putative domains are identified via primary sequence homology, or bioinformatics-based secondary structure prediction algorithms. Initial attempts were made to clone and heterologously express regions of *P. berghei* FusM in appropriate *E. coli* (DE3) strains.

Initially, two sections of the gene were cloned into expression vectors. These sections corresponded to amino acids 82-371, and 255-660, and were named PbFusDomA and PbFusDomB respectively. PCR products were purified using a PCR purification kit (QIAGEN) and cloned into pET15b, pET46b and pET41b (Novagen). pET 15b and 46b produce N-terminal His$_6$ fusion proteins, whereas pET41b produces an N-terminal GST+His$_6$ fusion.

Each of these clones was confirmed initially by diagnostic PCR, followed by digestion, and finally, sequencing on both strands. Following sequencing, and the confirmation of the absence of any substitutions or frame shifts, the relevant constructs were cloned into *E. coli* BL21 (DE3) Star, *E. coli* BL21 (DE3) pLysS, *E. coli* Rosetta BL21 (DE3), *E. coli* Rosetta BL21 (DE3) pLysS and *E. coli* BL21 (DE3) pMico (Cinquin et al, *Mol. Biochem. Parasitol.* 117 (2), pp 245-247 (2001)). The expression of each construct was then checked using standard *E. coli* T7 based expression methods. Expression was identified by SDS-PAGE and subsequent coomassie staining of *E. coli* lysates 5 hours post induction of expression, and western-blotting using an anti-His$_6$ antibody (His-probe from Pierce). Of all the constructs and cell lines used, only two gave demonstrated any detectable expression—PbFusDomA (31.2 kDa) and PbFusDomB (35.8 kDa) were only expressed in pET46b, using the *E. coli* BL21 (DE3) pMico cell line (FIG. 2). This expression resulted solely in polypeptide contained within inclusion bodies, and no soluble protein of interest was detected, even upon expression under a wide range of different temperatures. FIG. 3 shows the detection of PbFusDomA and PbFusDomB via western blot using an anti-His$_6$ antibody.

Figure 8:
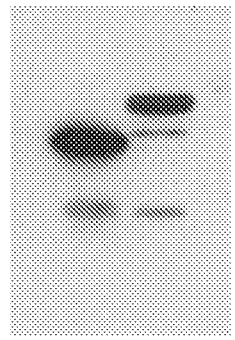
FIG. 8 is a Western blot of PbFusDomA and PbFusDomB expressed in pET46b and *E. coli* BL21 (DE3) pMico using anti-His$_6$ probe. 1; PbFusDomA expressed from total *E. coli* cell lysate, 2; PbFusDomB expressed from total cell lysate.

FIG. 8 is a Western blot of PbFusDomA and PbFusDomB expressed in pET46b and *E. coli* BL21 (DE3) pMico using anti-$His_6$ probe. Lane 1: PbFusDomA expressed from total *E. coli* cell lysate, Lane 2: PbFusDomB expressed from total cell lysate. For the production of antibodies, initially, SDS-PAGE gel slices containing approximately 250 μg PbFusMDomA and PbFusDomB were excised, ground to a fine powder, and resuspended in 1 ml MPL+TDM oil-in-water adjuvant (Sigma, M6536). For each of the two proteins to be investigated, a 200 μl dose was injected subcutaneously into five BalbC female mice, from which pre-immune sera had previously been collected. Each mouse was then boosted on day 21 (boost 1), and tail bled to a volume of 100 μl 4 days following this. Another two boosts followed this at 4 week intervals. Blood gleaned from tail bleeds was allowed to coagulate overnight at 4° C. overnight, and was then spun at 14,000 g for 20 mins. Separated sera was then removed from the resulting pellet, and stared at 4° C. until further use. To test for any immune response, sera were tested on a western blot against recombinant protein preparations of the appropriate *P. berghei* FusM domain. This sera was tested at the concentration of 1 in 50. The secondary antibody used was ECL Anti-mouse IgG, HRP linked whole antibody (from sheep; GE Healthcare NA931V). His-probe was used as a positive control, and pre-immune sera was used as a negative control. Immunisation using this method produced no obvious immune response to either of the FusM derived recombinant polypeptides, even after three boosts.

In order to investigate this further, for PbFusMDomA, a similar procedure was repeated, but this time, using a more powerful adjuvant (Freud's complete adjuvant for the initial immunization; Sigma, F5881, Freud's incomplete adjuvant for the boosts; Sigma, F5506). Also, protein preparations were not taken from SDS-PAGE gel slices, but from purified insoluble inclusion bodies following growth and induction of the appropriate *E. coli* expression strain. The immunization, boost and test-bleed protocols were as described previously. Following one boost, a potential immune response was seen at 35.8 kDa against recombinant PbFusMDomA in mouse 2A of 5 (FIG. 9).

Figure 9:
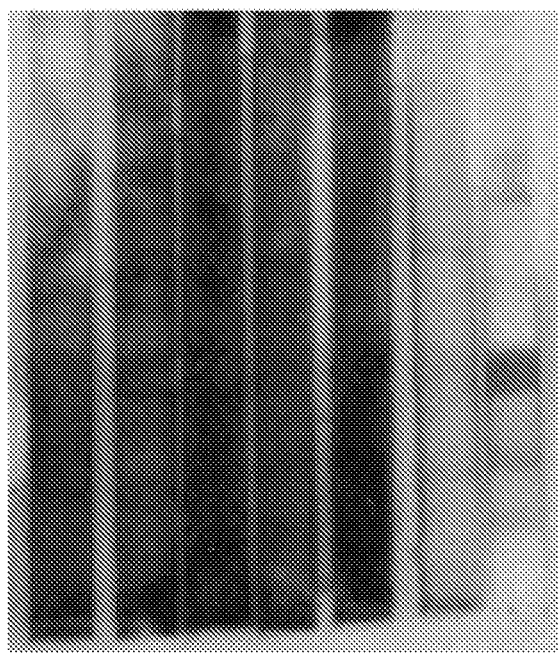
FIG. 9 shows the vaccination results as measured with a blot demonstrating serum response to recombinant PbFusDomA after first boost. 1; Sera from Mouse 1 (1 in 50) 2; Sera from Mouse 2 (1 in 50), 3; Sera from Mouse 3 (1 in 50), 4; Sera from Mouse 4 (1 in 50), 5; Sera from Mouse 5 (1 in 50), 6; negative control—pre-immune serum (1 in 50). 7; positive control—Anti His$_6$-probe (1 in 5000).

FIG. 9 is a blot demonstrating serum response to recombinant PbFusDomA after first boost. 1; Sera from Mouse 1 (1 in 50) 2; Sera from Mouse 2 (1 in 50), 3; Sera from Mouse 3 (1 in 50), 4; Sera from Mouse 4 (1 in 50), 5; Sera from Mouse 5 (1 in 50), 6; negative control—pre-immune serum (1 in 50). 7; positive control—Anti $His_6$-probe (1 in 5000).

Figure 10:
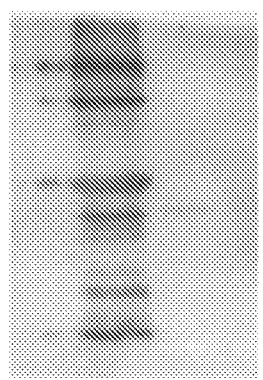
FIG. 10 is a Western blot using sera from mice vaccinated with the PbFusDomA antigen. The Western blot demonstrating mouse 2A response to recombinant PbFusDomA. 1; Sera from Mouse 1 (1 in 200) 2; negative control—pre-immune serum (1 in 50).

FIG. 10 is a Western blot demonstrating mouse 2A response to recombinant PbFusDomA. 1; Sera from Mouse 1 (1 in 200) 2; negative control—pre-immune serum (1 in 50).

Following this, mouse 2A was culled via cardiac puncture-resulting in 1.2 ml of blood. Sera was purified as described previously, and used on a western blot against recombinant PbFusMDomA. As can be clearly seen in FIG. 10, the serum from mouse 2 clearly recognizes recombinant FusM protein preparations (along with other *E. coli* proteins of varying sizes). A soluble version of *P. berghei* FusM (amino acids 355-660) coupled to an MBP molecule was produced. This polypeptide has been separated from *E. coli* Rosetta BL21 (DE3) pLysS cell lysates, and was used to immunize BalbC mice.

Nucleic acid sequences for use with the present invention may include at least portions of one or more of the following parasitic FusM genes:

*Plasmodium falciparum*
(SEQ ID NO.: 15)

```
ATGAACAAAAGGAAAAAGACAAAACACTTAAAAGTTAATTCTATATTGAG
AATCTTTTTTTTTTTTTTCCTTATTTCTTTTCTTTTTAGTAATTGTAAAT
TAAATGATTATATAAGAACAAAATACCCATTCATTCAATTTGTATATTCT
TATTCCAAAAAAAAGGTATGTACATCTTCTACAGATGATTCCACATGTCG
TACTGTCGTTTATGGAGATTTAGATGTTTCTAATAATTCGGTGTTAAGGT
TAAAGGTTTTAAGGTCTGAGGGGAAAGGCTATTTTGTTACTATTCGAAGA
GACTATGTAACAATATCTTACTATCTGAAATATATGAAAGATATTCCTTT
AAAGTATAGAGAAGTAGTTGATATATTTAATAATCATAAATATGAAAAAT
ATACAGAGAAACAAATAAAGGATTTTACTTATAATTGTACTGCTATTAAA
GTCGAAGATGCCAATAATACTGTAGGGGATTTTGCACCTCATTATCATGA
ATATACAAGAGGAGAATCTTGTATATGCCCTTCATATCATCTTTTTAAAA
ATGACAATTCAATAAAAAGAGCAAAATTAAAATGCACTTATTTTAATATG
TTATTTACAGATAGTGCTATAGTATATAGCCGTCATTGTGCTATAATGGA
TTTGTTTTATTTTTCTGTTTATGAAATTGACTATCCTCCAATATTTAATA
CATATATAGATATAACAATACAAGAATATACATATGATGATGTATCAGGT
ATGTCACTGAATAAACATGATTTAGTTACAAAAGAAAAGAAATATGAAAT
AAATGATTCGATGTCTGAAATAAGAGACGATTATTTTGATCTTTGGTTAT
TTTTAAGAGGAGAAAGACATGGAAAAAGAACTTTAATTAATTTATCAAAT
GATTATGTTGTTATTCCATCTTCACCTTTAGATGATGCGGATGTAATAGA
AACTGATGTTATGAGAAATTGTGGTTTGAAAGAAGATAATCCAGCTTTAA
AAGGATGTGATTATAAACATGAATGTAACATTATACATCCATGTTTAGTA
AAAGCAATGATGTTACCAAAATATCTTTTTGATTTAAGTGGTAAAACATG
TAATAAATTAGGTGTATCGTTAAATAAATGGAGAAATTCTGATGGGAATT
TTTGTGGTTCTTCAGCTGGGTATTGTTTATCTGAGAATTTGTTTAAATAT
TATTACATACATAAAACATCTGTTGGGAATAGAAAACCTTCGAAATATAA
AATTAAAAATATATATGGGTCTGAACCACAGACAAAAGTCTATACATCTG
CAAAATTACCTAATTATTTAAAAGATAAGGTAGATAGTAATAATAATAAA
TCTTATGATATTAATGATATAGATAATAAAATATTTTATAATGAAAACGC
TGCTGCACATAGTCATTTTATTGATTACAAATATAATGGAAATCATACTG
TTGAAATTAAATTCGAAACTAATGCATTAGAAGTACATGAAATCAGACCT
GTGTCATATGGAACTATTACACATATTACTATACCAAAAGATTGTTCATC
AAATCAAACAAATTCTAAAGAATGTATTCTTGTTGTACATACGTGGAATA
ATAATAAAACTATAGGAGCTAACTTCTCTTGTCATGTTTTATGTGTTGAT
AAAAGTACTCAACAAGTAGCAACACATATTAGTCCCATTAGTAAAATAAA
TGCACATATTGATGCAAATAAAAATTATGCCTTTTATTTCATTATTAAAT
TTTTAATAAATAAAAAAATAACAAGTAATTGTACAGCAATACTAAAAGAT
GCTGATGGTAGGGAATGTTCAAAACTTTCATTTAATTTAACATCTAAAGA
AACAATAAATGTAGTAGAATCAGGAATAGTAGCACAACCTGTAGAAAGTG
AAGCTCAAATAAATAAATATGATCCTGATGTATCAGGAGCATCTACGCCT
ACAGCTGATAAATGTGATTGTTATTTTAATTTATTATGTTATATACTTAA
```

-continued

TTTGAATACATGTGTTTCATATTATACTAAATTAATTAAAGATTACCTTG

GAAGATTTGTAACGATAGCTATATTAATTTTTCTTGCACCATCCTTAATA

CCCCTGTTACCATTTATCATTAAATTTTTTATATCATGTGCATCTCTCCC

AATGAAATTATTTTCCAACTTTTCTTCTTGGATGGAAAATAAAAAAAAAA

GTAATAATAGTACAAAGCAAAATAAAAATTATTTTCAAAGGAAATATGAA

AATTTCAAAAAAAGAGAACAAATATGAAGAAAAATAAATGTACATCATC

TTCCGTCTCTTCTTTAACAAATGTTTCAAGTATTTCTTCAAATAATACAA

TGAACAGTGATATAAAAAAGGACGTATCATTTAATAGGATTAAATCAAAT

AGGTACAATAAGGAGAATCATAAAAACAAAAGAGGAAAACAAAAGGTAA

CCATAGTAAATATAGTGGTACCTCGATGGAGAGTACACTAACAAATACAA

GTCCCTCAAGTACACCTGATAATTTAAGTGAATCTCATATAACATCTAAT

TCAAACAAAATAATTATTCATCAAAAAACAAGTGTAATATGCTATATAA

AAAAGAACATTCCAGGAAAAGTATAAGAAAAAAATCTATGGGGATATCTG

AATATTCTTCTTAA

*Plasmodium berghei*
(SEQ ID NO.: 16)
ATGATTATTATTATTTTTTTTGTATTATTTTAAAGTATTATAAATGGTG

TGACTTTAAAAATAAAGTATTTTTCATTCAATTAGTGTATTCTTTTGCGA

AAAAAAGTGTCTGTACTTCATCATTGGATGATTCAACATGTCACACAGTA

ACTTTTGGTGAATTGGATGTTTCTAATAATTCGGTAGTGAGATTAAAGGT

GATGAGAAAAGGAGGAAAAGGGTATTTCCTGACAATTCGAAGAGATTACG

TAACTGTCTCATATTATTTGAAGTATGTAAAGGACATTCCTTTAGAATTT

AGGGAAATTATAGATATATTTAATAACCATAAATTTGAGCAATACACACA

AGAGCAAATAAATAAATATACATATACATGTAATGTACGTAAAATTGAAG

ATATAGATAAATATGATGAAAAAAATCCAACTAAATTTCATGAATATACA

CGAGGAGAAGCATGCAGATGCCAAACATATAATTATTTTAAAGATGATGA

ATTTATAAAAGAGCGAAATTAAAATGTATTTATTATAATATGCTATTTA

CTGAATCAGCGACAGTATATAGACATTGTCCTATTATAGATTTAATGCAT

TTTGCAGTTTATGATATAGAATATCCACCAATATTTAATACAATTGTTAA

TATTACAATAGAAGAGTATTATTACAATGATGTATCATCTGTTTTGAACA

ATAAATCTGATTTAGTTACAAAAGAAAAAAAATATCAATTAAATGATACT

ATAACAGAAATAAGAGATGATTATTTTGATTTATGGTTATTTTTAAAAGG

TGAAACACATGGAAAAAGAACCCTTGTTAATTTATCAAATGATTATATTG

TTATTCCATCATCACCTATTAATAACAGAGATGTTATAGCTAGTGATATA

ACAAGAAATTGTGGACTATCACAAAATTCACCATTATTAAAAGGTTGCAA

TTATTCAAGTATATGTAATATTATGCATCCATGCTTACGAAAAGCTATGA

TGTTACCAAAATATATGTTTGATTTAAGTGGTAAAACATGTGGAAAGTTA

GGTGTATCTTTAAATACTTGGAGGAAGTCAGAAGGTAATTTTTGTGGGTC

AGAAGCTGGATATTGCATATCAAATAATCTCAAAAAATATTATGATATTC

ATAATTCTGCATCTATAAAAGATGGTATTTCTCTTTCAAAGTATAAAATA

AAAAATATATATAATTCAGAACCACAAACTAAAATATATGAATCCTATAA

-continued

GTTGCCTGATTATTTAAAAGATAAAATTAAGAATAATAATCATGCGGAAA

TGGATGAAAATGATTTAGATAATAAAATTTTTTATAAACCAAATGTAGCT

GCACATAGCCAATTCATTGATTATAAATACAATGGAAATCATAGTGTAGA

AATAAAATTCGAAACAGATGCTATAGAAGTATATGAAATAAGACCCGTTT

CCATTGCAACAATTACTCATGTTACTATACCAAATGATTGTGCATCTAAT

AATTCTAATTCAAATGAATGTGTCCTTATTATTCATGTATGGAATAATAG

CAAATTTGTAGGTTCAAATTTCTCTTGCTCAATTGCATGCACAAATAAAG

AAACTGACCAATTGGCTAGTCACATTAACCCTATCGCTCCTGTGCGTGCA

TTTATTGGACCAAATAAAAACTATGCTTTTTATTTTATAATAAAATTCTT

AATAAATAAAGAAATTACAACATTGTGCAAAGCTATTGTAAAAGATTCTA

ATGGGAAAGAATGCTCTATAGAAGAATTCGAATTACAATCAAAAGAAAGT

GTACATATAGTTGAGTCAGAAGTAGATGAAACAACGGACCAAGTAGTAGT

AGAACATCATACACAATCACCTGATATTAAAAACCCTGATGAATATGTAT

GTAAATGTACTATTAATTTATTATGTTATGTAATTAATTTCAAAACATGC

TCTAACTATTATATAAATACAGTTAAAACGTTAATTGGGAAATTTGCTAT

TATAGCCATATTAATTATATTAGCACCTGCCTTAATACCTCTTCTACCAT

TCTTTTTAAATTTCTTTTTCCTTTTTATATCTACTATACTTAAATTATAT

CAATCTATTATAAGCACAATAGGACAAATCAGAATACGAAATAATGATAA

GCCTATTATTTATAAAAAAAAAATTCATGACATGAAAACCAACTACCTAT

CTGTTTCTTCATATTCGTCATTATCTGATTCAAGCAGTATATACTCCACT

GATTCAGTATCTTCGATGAGAAAAATAAAAAAAATTCAATAAAAATAA

TATATCAAGCAATATAAAACATAAAAAAGGGGGGAAAAAGGTTAAACAAA

AAGAGCCAAATAGAAATTCAAATCACACTTCCCATGAATATGCAGATACA

TCTCCGTCAGGTAAAAGTAAAATACCCCCATTGCGATAA

*Chlamydomonas reinhardtii*
(SEQ ID NO.: 17)
ATGTGTCGTGCCATCGCGGTTGCGCTGATAGTTTACCTAGCCCAGCATTA

TATTCTTGCGCACGCTGAGGTCATTGCAAGTGGGCGCTTGGAAAAATGCG

TCGTCGATGGTGTTACCGAGGAGCTGGACTGCCAGGAGAAGGTGGTGGTG

ACACTGACGGTCGGAAATGGGCAGAGCCTGCAGGCCGAGGCTCTGGAATT

CTCGCTCAGCTGCCTCAACAGCCCCGACGGAGCTGCCCCTGCAGCTGCA

GCGCCGCCGACCCTACTTGCGCATGTCGTGACCTGGCGGCGCCGCTGCGC

GTGTCGCTTACCAAGTCGCCGCTGTGGGCCTCCTACCCGCTGCAGTACTT

GTCGTCCTTTAACTGGAAACCCCTGGAAGTCATCCTGCGCCCCAGCAACA

AAGTTTGCAAGGACGGCGACTGGGAGGACTCGCCCACGTGTGGCTGGTTC

AGCCAGGGCGGTGTGCGGGTGGCGGACAGCCAGGGATTCTGCTGCGAGTG

CAGCAGCAGCCAGGTGTGGGACGACACCTTCGGGTCCAGCAAGGAGCGCA

CTCGCGCCAACCTGGACTGTGACTTCTGGAGCGACCCACTGGACATACTG

ATTGGCCGCAAGCCGGTGTCCGCACACTGCCTCACATTCGACCCGCAGTG

GTACAGCGGCTATGAGCTGGGCGCCGCCTCGCTGCAGTTCGAGATCGCCA

TCACCGTGGAGGTACCCACCGCCCCCTCCCCCACCACAGCCACCACCTCC

GCCACTCCCCGCACCAACAACAGCAGTAGCGCCAACAGCACCAACAGCAC

-continued

CAACAGCCCGGCGCCGCAGTTTCTGTCCCCGCCTGCGCCCAGCACGCGGG
AAGTGTTGCATCTGGGTCCCTCGGTGCCTCTGGCCAGCAGCGCGAGCCGC
CTGCTGTCCGCCAAGCTGCTGGGCGACCTGGCCATGTACACACAGCTGCC
CGCAATCAGCAACCAGGTGCTGATGGTGCCGCAGCCGCCAGCCGCCGCCG
CCGCCACCGGCTCGCCCCTGGACGCCACCCTGGCGACCAACCGCTCCGCC
TGGATGCTGCTGGACAAGACCATGCTCAGCATGGACGGCCTGGCCTGCGA
CAAGGTGGGGACCGGCTTCTCAGCCTTCCGCTACCAGCCCAGCGGCTGCG
GCCGTGCCCCTCAGGCCTGTCTGTCCGGCCAGCTCAAGGACCTGTGGGAG
GCGGACCTGGCGCGTATCGCGGACGGCCGGGTGCCGCTGTACATGATCAC
CAGGTTCACTGGCGGCAGCGACACCACGCTGCAGTCCTTCTCCGGGGGCC
CGCTGTCGTTCGCGCTGCCTGTCACCAGCCACAGCCAGAGCCTGGTGACG
CTGAGTGTGGCGGCGGACGGCGTGAGGCTGGTCACCAACCGCAGCCCGGG
CAAGATTACAGGCGCGGCGGTGTGCCGTTTCGCCGGCACTTCCTGTGGCG
GCTTTGAGGCGGTGGCAGCTCGCGGCTACATCTACGTCAACATCACCAAC
ACCGGCCGCCTGGACAGTGACTACACACTCACAGTGTCCAACTGCTCGTC
CAACGTGCGGCCCATCGAGGCGCGCACACTGGCCGTACGCGGGGATCCG
CCGCCAGCCTGGATCCGCCCATGGAGCTGTACGTGGAGGACCAGGCGGCA
GCGGCGGCGCGCACGTGCACAGTCAGCCTGTACGACTCAGTCGGCGCGGT
GACGGACTCGCTCACGCTGTCCTTCTACACAAACGCCACCCAGCTGGTCG
TCAAGCCCTCCGGCGGGTACAACGGCACGGGGGACGGCGCGGGCGTAAAG
CGCAACGGCACCGATTGCAGCACGGCCTGCACCAACCCGATTGACGTGCT
GTGCTTCGTGACCAAGAAGTGCTGGTCCAAGTTCGGGCGGCTTCTGGGCA
TCATCGGCGGCGCCCTGGTGGGGCTGGGGCTGCTGGCAGTAGCACTCAAG
TTCGGGTGGCTGGCCTCCCTGGCGGCCTCGTGTTGTGGGGGAGGAGGAGG
AGCAGCAGCAGGCGGGGCTGGAGGCGGCATGGGGCTGGGGACCGGCGGCG
GCGGAGGCTGTTTTGGAGGCGGGCAGCAGCAGCAGCAGCAGCCGCCTGCT
GCTAGCCATGCCATGTCGCCACCGCAGCAGCAGCAGCAGCGCTCGCATGC
GGAGGTGGCAGCAGGGGCTGCAGTGGCAGGAGCAGGAGCCGCTGTTGCAG
CAGCGGCGGTGCTGGGAGCCAAACACGGCGGCGGCGGCGCGCTCGTGGCG
AAGCAGCAGCATACCGACACCCGGCATTTGCAGGATCGCGACTCACGAGC
CACCGCCGACGGAGCAAGCATTGACAGCAGCAGCGCCGGCGGCAGTAGCA
GTTTAAGCAGCTACACCCAGCCTCGTAAGGCCGGAGGCAGGCTGCTGCAG
CCGCCGGCAGCAGCAGTGTTTGTGCCTGAAGGCGGC

*Trypanosome cruzi*
(SEQ ID NO.: 18)
ATGAGCCTGTCTTTGTCTCGTATGCTTTTTCTTTATTGCTGTTTGCCCT
GATGGTTGCAACAACTCCTTTTGCCGCGGAGGGTTTACTGCTGGCGTCGT
CTTCCATTGAACAGTGCGATCGTGTGGGAACCGACAACTCGCTGCCGTGT
GAGAAAAAGTTGGTGGTGACGTTGTCGGTGGACAGTGATCAGGCGGAAGA
TGTGGAGGAGTTTGTGATTTTGCGCGATGCCGTGGACAAAACGAAAGGAA
CGGGGGAGGAGCACGTGGAATTTCAACCTATCCGTTTGACGACGAGCAAA TCACGCGTGCAATACAGTTACCCTCTCTTTTATGAAAGGAATTTCAATGC
CAAGCCCTACGAGGAGGAAATTACAACGGAACTAGTTGGGTGCGATGATA
CATTTAGTCCGAAAGCAACATGCGGGCTGGCCATGGACACCGCGGGAAGG
CCTATCCCGTACAGTCAAGGTTTTTGTTGTCGATGTGGTCCCTGTCAGTT
GTTGGGGTTATGTCCCGTGGGTAGCCGCGGTCTTCAGGTATGCGACATAT
TCAGAGGGGCTGCATTAGCCTCATGTCTCCGTTTTGGAGAGCTTTGGTAC
AGTGGGTACAGCATGGGTTCGGCTACTATCTGGTATCGCTTGTCGGTAAA
ACTGACGACTGACTCCCAAAATAACTCCAAGACAAAAGAAGCAGTTTTTG
AGCTGGGACCGGATGTGCTTTCAGGGTCTTCAGCGGAGTTTGGGGCTTGG
GTCAGTCTAATTGGGGACTTTGTGCCGGCGGAATTACCATTGGTTCTAAG
TAATAAAATGCTTTTTATTCCCTCTTCTCCAAGAATACACGAGCGTGTTT
TGGCGGGCCAAAAGGAGTGGTTAATTCTGGACAAGCACCATGTGAGCATG
CAGGGTCGAGATTGTAACAAGGTTGGGGTATCTTATGAAGCCTTTTCGGG
TCAGGGGAGCAGGTGCCAATTAATTCGAGGGTCGTGTCTGGCCGATCAGT
TGGAGGACTACCGTTCGAGTGATTTGGCAGTTGAAGCCCGAGGGGGTAGA
GGCAAATACCTGGCTCGCTTTTTTGGAGACTTTGTTGTCAACAACGTCAA
CAACAGCAGAACAAGACTCTCCTACTGGATGCGTGGGTCATTGGCGACGA
TGTTAACTGTTGTCATATCAGCGGACAGACTGCAATATCTGGTTTCTGTT
TCCCCAGGTGAAATTGTCTCTGCGGTGATGTCGAAGTCGACAGTAGAGGA
AAGTTCGAGAGATGGATCCGTTTCTGTCATAGTGCGCAATATTGGCCACG
TAACTGCGCAATACACGCTTGGTGTGGGGAACTGTTCGGGAAATGTTTTC
CCCATTATGGCCCAGACCCTGAGTTTGAGACCACGAGGGACAGTGATACG
CAGTTTTGATCTGAATATCCAAGATGTGGCGGAAGAGAGAATTGTGCAAT
GCGACGTAACTTTACGAGACGCGAAAGGTGCTATCACGGACAAGAAGATT
TTGAAGTTTCGAGTAACAAGTAAAGTATTAACGAATGATACACAGGGCGG
CAATGCACCAACTGGAGGTGGTGCCAGCGTGGATGGTCAAGCCCCTCCAG
CTTGCTCGCGTTGTGAGTGGTACAAGATTTCCTGTTTCCTGATTCATGGC
TGTTGGTGGCAGCCACTGGTGTATGTTTTGATTGCCATTGCTATACTGCT
GGGTATATATTATTTTTCGGACTCTCTTCGCGCAGTAGTGAACCCAAAT
TACACGTGGTTCACTGA

*Trypanosome brucei*
(SEQ ID NO.: 19)
ATGCCGACGGAGACGTTATCATCTGTTTTTGTGCTCGTCGTCCTTGTGAC
GACAAGCGGCCTTTTCCCCTGCACTGAGGCGGCATTTGTGGCCTCGTCGT
CCATCGAGTACTGCGAGCGCAGTAGTAATGGGGAACCGTTTCCATGTGAA
AAGAAGATGGTTGTGGGCTCTCCGTGGGCAGCGAGCAAACAATTGAGGC
TGAAGAGGTTGTTCTTCTCCGCGAGGCAGTTGACAAAACGGGTGACGAAA
AGGGAAAGCGTGTCGAGTTTGAACCAATCCGCCTAGTGACGACAAAATCA
CCGGTGCAGTACCGCTATCCTATTTATTACATAAGAAACTTCAATGCCAA
ACCATATGAGCAGCGTCTCAGAACAAGTGCAAGCAGTTGGTGCGACGATT
CTTCCAACCCTGGATCCGCGACATGCGGCGTGGCGCGTGATCGGAGAGGA
GATGTGATTCCGTACAGTCAAGGTTTTTGCTGCTTATGTGGCGCTTGTGC -continued

ATTGTCAGGAATTTGCAACCCAACTAGCCGCAGCGTTGGAACTTGCAGCG

TGACGGGGGATACTGGAATGGCATCATGCCTTCGTTTCAGTGACCTCTGG

TACGGTGGCTATACCATTGGTCGAGGTGTTGTATGGTATGAATTGCAGGT

GAAATTGTCAAGTGGGAACAACAGCACTGGGGGAGGCTCCACGGGCTCAA

AGGAGTTCACGATGTCTTTGGGGCCGGATAAGTTGACCGCCACGTCGACA

GAGTTCGGCGCGTCTGCACGTCTTATAGGAGACTTCGCACCCCCAGAAAT

GCCTCTTGACCTATCGGGAAGATGTTGTTTATCCCCTCTGAACCGCGGG

GTCATGAGCGAGTGGGTGCTGGGTATAACGAATGGATTATTGTTGACACC

CACCTTGTTTCTATTCGTGGCACCGAATGTAATAAAGTGGGCGTGTCATA

TGAGGGTTTCGCCACTCAGGGGAGCCGGTGTGACGCGTATCCGGGCGCTT

GCTTGGCGAATCAACTGGAGGATTATCGTGATCGGGACTTGGAAGCGGAG

ACTAAGGGGCAACAAGGGAAATATATGGCTCGCTTTTTCGCTCCTTTTGG

TTTTGACCCACTGGCCAATGCCAGTGCCCCAGCTGTGGCTTACCAGGTGA

CAGGAACATTATCAACGATGGTGACGATAACAATATCCGCTGATAAGTTA

AACTTTGTGTTGTCTGTGTCCTCGGGTGTGATTGTTGGTGCAACCGTTTC

AGGGAAGGTGGTGCATTCCTATTCGCGGGGAAGCACCATTACCGTGACGG

TTCTTAACACTGGGGACATCGAGGCACAGTACACGGTTGTTGTCGGCGAG

TGTACGGTTAATGTTCAGCCGATGGTTGCCCAAACTGTGTACATACCCCT

ACAAGGATCAGCGCAGCGACGTTTCACTCTGATCGTACAGGACAGTATTG

AGGGAGAGGCCAAATGCAATGCAACGCTGAGAAACGCCAGGGGCGACGTT

GTGGACACCCGCGCTATTTCGTTCGGTGTTAAAGCGCTCAAACCAAGCAA

TGGCTCTCAAGGTGGCAGCACCTTTGAAAATGGACGGTACAGTGAGGAGG

CAAAGGGGGAGTCGCAGTGCCAACAGTGCAGTTGGTTCAATCTTTTGTGT

TTTCTGAGGCATCGATGCTGGTGGCAACCGCTGGTGTACGTCCTTCCTTC

AGTGACCCTGTTAATGCTGCTGCGCAGGTTCCTTGAGAGTCAGTCAAGGT

CCCGCCCAAGACCCCAATTACACCCTGATGAGCATGAACTGAGAAATACC

GGTGCCATCTCTTCGTGCCATCTTCCCCGCGCACCGTACGTTAACACAGT

GCACTGA

*Cryptosporidium hominis*

(SEQ ID NO.: 20)
ATGTGGTGGAATGTTTACTTATCGAAGTCATGCCCAGTTTGGATACCACC

ATGGTGGACAGCTTTTAGAATAGGTGGATGGAATTGGCAATACTCATTAG

AGGTTGAATTATCTTGGTTTAGTCCAACAGAATCATCAATTAATAAGTTA

TCAAGTACAGAATTGGAAAATATGGAAAATGAATGTAAGAAAGAAAATA

AAGATTCCACAATAGATTGTTCAAGAATAAGGCATAAAGAATCAGGAATT

CAGACTTCTGTACATACATTAAATTCATCGTCTCCATCATTCTATGATCC

AAATTTTGGAGCTTCAGTACAGGTAATAAGTTCAGGACCGCCGTTTGGGA

GTGCTAATGCAAAGGATTTGAATGGTTATTACATGTTACAACCAACATTT

TCACCAAAAGGGATGCCTGCTAGTATTGCAATTCCTCCTTTAAGAAGTGG

GTGTGGAAAAGCTTCAAAAAAACCAAACAGAAGAGGAAATGAATGATTGTT

TAAAGCCAACATTAATTATTCCTCCAGAAAATGCAGACTTTACAGGAGTT

TCATGTGATAAGATAGGAACAAGTGTTCATACTTGGAGTTCTGTGAATGG

TAGATTTTGCTATCATCCACCTGGGACTTGTCAAAGAGCTCAGATAGCTC

ACTTTTATAAGAAAGTTATAGAAGATCATTCACTTGGAAAGATTTCACAA

TATTCAGTGAGAGCACAAAATTCTGGTTCTCCACAGTTGATTTTGGATTC

ATTGGGAGAAATTGGTCATGAAGAGGTGGATCAAAATGATATGGAAAATA

TAACTAATATACAATCACGTAGATTCTTTTTGGGATATAATTTTGATTCA

ATCTTTGACACAGAAATAATGTTCTCAGTCGAAGCTTCTTCTGTGTCTTG

GGTAGCAACATCTTCTCCTGGAATTATTACATATATAGAACCACCACCTT

TGGAGGCTTGCACAGCAATGAGTAGTTTTGGCTGTCCTCTAAAGGTTTAT

ATTAAGAATAGTGGTAAGTTTGAATATATATATACATTTCGAATTGAATT

AAAAATAACTTATCAAAAATATTCTATAGGGGATATTGATTCAGGTTTTG

TAGTTCAAATACCTTATTGTACAAAGTCAGGAGTACAAACAAGTGAGGTA

GGTTTATATTTAACTCATTCAAATTTATATAATTAA

*Toxoplasma gondii*

(SEQ ID NO.: 21)
ATGGATCCACCACTGCCGCGATGGAGAGCCGTGGCTGTGGCAGCTTTTCT

CATCGCCACCATCTGTCACAATGGCGTGGACGCCGACATTCCTCAGGCCG

TGTCACGGCAACAGATCTGCACAGTCAATGGCGCATATGGAAAGGATGAT

CCTAGACGAATGCAGTGCAAAGATACGATTCTAGGGACTCTGAGAATATC

TAATAAAGAGAAATTTTCGTTTAATGTCATGCAAAACACCATCGATTCCC

GGGACAAGACATACGCTGACGTGGGAAATGTCGGATTCGTCGTGACCATT

ACGAAGACTCCCGTAACAATATCGCTGCCTCTAGAGTACATCAAGGAGGT

ACCGTTCGATTATCGGGAAGAGATATACGAATATTCCCGGTGGGAGGCTG

GGCGACTGCCGGAGAAGTTTTGTTACGAAGACACGACAGACAAATGCTCT

GAAGATGGGAAGCTGGCGGTCCACCCTCACGGCAAGCCCCTGTCATGGGC

CCACGGCCGCTGCTGCTGGTGTAGTGAAGTGCTGGCTTTCACGCATATCA

ACAACATGAAGAGGGGCAACTTCCGTTGCAATTGGTTTGCCCCGCCCCGC

GCCTTGGAACTGGTGACTGAAACCCTCTACGACCAGTGTGAAGCCGGGAA

AATAGACGGCACCGTTCCATTGGACCGAGATTGCGAAAGAGAGAAGCACG

AGCGCTTGGGCATCACCGACAGAGTTTACACACTGAACTACACTACACCA

GAAATCTTCGACCGTTCTGTCTATTGCAATACAAAGTCTTGCTTGAAACA

CGCCATCATCTTGGACAAGGACTATGTTTCTGTCACGGGTTATGAATGCG

ACAAAGTTGGCACCGGCCTCGATCGATGGGGAGACATGAGAGGAGAGTTT

TGCAATCTGTTACCAGGGACTTGTATCACTGGCCAGCTTCGGAAATTCAA

GGAAGTCGACAAGCTACGGATCGAACAAAATCTGGCACCATTATATGCAC

TGAAACGGGAGTTCGGGGGCTTCCCTCGATATGCGCCAAACCCGATGAAT

GGAACGGGTTTTTCAACAACAGGCACAAGACACTACCTCGGCTACGATTT

TGGCGAGCAGCACTACTCAGACATCCGTTTCGAGATGGATGCAACCGATG

TCACATGGTTGAGGGCAACATCACCCGGTCACATAACCTTCATTGAGGTG

CCTCAGCTAGACGCATGCTCGTCCAGTACCATTGGCGGGTGTCCACTGAA

AGCCTACGTCTGGAATTCAGGCAACGAAGATGCTGCATTTGCAGTAGAGG

-continued

TACCCTTTTGTATCGATTCGATTACAAAGGAGCGAACAATCGATGTAAAT
CCCATTACGCCAGTTCGGACGACAGTGCCTGCTGACAAAACGGTTGTTTT
CACGTTAACCTTTAAAGCCATTTCTTCTAGTAGTCTTGGCGTTACATGTT
TCATGAAGCTGTACGATGCCCAGCATCTCATGCTCGACCAAAAGACATTC
AATGTGACGACGTCGGCTGCTCAGGCACACGACACACAGCACTCACACAA
AATAACGAAGATGCCTCAGAGKAAAACTACTCGGGGGGGCTTTTACGAAA
GCAGCCGTCGGTGCCACAGCAGCAATGGGTTTCTTTGGTCGGAGAACGGG
GAAGAAGAAGAAAGGAGACACAAATGTTGAGGCGCATTCTGTAACGCCAC
AATCGTTTGCCGAAGACGCAAGAGGTCCTGGGATCCAAGATAAACTTCAG
GGAAAGGCTGACCCGGCAGAAACGTCTCTGTTCGGGGAATCGGCCACGAG
TCACGCAGCGAAGTTGAGCAAGAAGGAAAAACGCAGTTTACGCAAACAAG
CAAAGAAACAAAAAGGCAAGAATATCAGCGGCAGGCAGCGGCAGGGAAC
GCAGAAATTTGGGCAGGAGAAGGAGAAGCCACTGCGTCTAAAAAAGACAT
GGTTTCCAAGAAGAATGGGGTCGAGGGGTCGCGGTCCTCGACTATGGGTA
TCGCCGACAACAACCAATCTGCTTCAGCAGTCACGAAGTCAAAACCGCAT
ATCATGAAGGAACAACGGGAGACAGGGGCCAAACGAAGGCAAGGGGAGTG
TGCAAGAACAAAGGAGGAAGATAAACGCGGGCACGTAGAAGGGAAACTGA
AGGAGAAACACTCTACCCAGAGCCAACCGGATCATCCTCTCTCTGCAGGA
AACAAGGGCACGAGCACAACTCAACAGATCAGGAGTCAGATTGAACATAA
ATCCTCCATTTTCATGGGAAACGACAATCAGACACCTCTCGAAGTAGAGC
TAGAAGGACAACTGCGGAAACATCTAGGTCAAGATGACTCTGATTCGCAC
CCGTCAAAGGCCGGAAAAGACAAGGTGCTTGAGCACGGGCAAACACCCGT
CGAGAGGGAAAAAGAAGGCAACGAAGAGGATAGCGCAGATAGAGGGAAAG
AACGATCAAACGTTGGGATCACTGGTGCAGCAGGGAAGATGAGGAAGTTC
CTGCACAGAAAAAGGGATGAAATCGAATACCAAGAAGGCCGTGAAGAGGC
GGGATTAGACGCAGTGTCCATCAGTAGAGGAAGTACACAATGCACCCGTG
CACGGAAGGCGAAGAGAAAGAAGCAGCATTTGAAGGAACCGCGAACACCG
CAAGAAGAAAACCCAGAAGATGACATCGAAGAACAGGACAGAGATGAAGA
AGGCGAATCCGATACACTAAGGGATACGACTGACCAAGGAGGCGCATCAC
CGCAGACAGCACGACCAGAGCTCACCACAGTAGTGGCACATGAACCCGAA
ACACGGGGGAAAAATACATTGAAGGGAGTTTCTCGACTCTACCCTCTGT
GGAAATCGAGGAACACAAAGAGATTCAGATGGTCGAAACAAATCCTAGTT
ACTGTGTTTCAATGAGGTAG

*Theileria parva*
(SEQ ID NO.: 22)
ATGAGCTCTTTAGGCCCTTTTAGAAGTGTGTTCACTTCCCTTATATACTT
CTCAATCCTACACATTCTCGGCTTTACATCACTATTCAATTTTTACACCA
CTGATAGCACTGGTTTCTTCTTTGTTGACTCAGCAGTGACCGGAAACATA
ACCCAATGTGTTAGAAATAGCGATAAACTCTTCGATGATCAAACTTGTGT
ACAAAGATTGCACACCAACGTCGATGTCTCACATGGACTCAGGGAGTACC
ATTACATATATAGAAGAAAAGATGATTTATCTAAGGGATTATACTTGGTG TTAAAGACCTCAAACACTTCTCTACTCTACACTCTCAATTATCAAACTAT
GGTCCCGTTGTATTATACGGATCATACGGAGAGGTGGACGTATAGTGAGA
TTTCAGGTGAGTTGAAGACCTCGTGTAAGAGTGTGCAAAATTCTAAATGC
ACTAAAAAAACTCAAGTTCCACCAGGTATTGATTTCTTACCCAGAGTCTG
CTGTATCTGCGGACTGAACGTACATAAACCAACGCCAAGAGCTGATTTTA
AATGCGGAGGATTTCTGGCTATGGGAGGTAGGACAGCGTTGAGTATGAGT
TGTTTGGAGATAAGTGAGCCCTGGTATAAGCTTTACAAGACCAGTTACCC
ACCAGCCATAAGCAGAAGTGTTACTGTTAACATTTACAAATTCGATTCAT
CCACTGGAATTATCCCAGACGTGACATTGGAGGATGAGGATAAATTTGAT
AATTATGACTTTAAGAAGCGGGAGAAGAAGGACCCGGTGATCAAGTCACC
GGAGATCAAATCACGCTCCACTAAAGAAATAACGGGAAAAAAGATGAAT
TACACCCCAATTTCAGACGCATCATCATCGATGATACCGTCAAAGAAGAA
CATATCAATGATTTGGATGTGAAGATAACGCTGTTGTCGAGTAATACGAA
GGATGGCTCTGCGCCCCGTTATTTGATAAATACGTAGCCATACCATCAT
TCCCAAGAACCAATGAAACCGTCAAAGGCTCATCACTCATGGACAAATGT
CAAGACAGCACCTGGAAAACCAAACCCGAATGTCCCAAATATATGAATCC
ATCGTTGTGTGATATATGGCGTTGTACGTTGAATATGAGGACTGTGAAGA
TGAGTGCGGTGGATACGGATGGGTTGATGTGTGATAAAATCGGCTTATCA
ATGAAGAGGTGGGCAAACCAAGAGGAAATTTGTAACTCAAGCCCCGGCTC
ATGCCTCAAAAATCAGCTGAAACACTACTTCGATCAGGAAAAAGATGAGG
CCAAATTACCAAAATTGTACGGAGTAGAGCCAACGTTTACAGCGGTTAAA
AAAGATCTGTCATTACCAGCAGTAAAGGAAGCAAATAAAACAACTCTGGA
TGATCCAAACAGAATTCACACTCTCACTTATATCCACTCTAAGGACGATG
TTACCAGACTTAAAATCGATACCTTCGACGCCACAGTCACCGAAATCATC
TCCGATTTCCCCGGGTTCATCGTCTCCGCAAAGATGGACGGAGAGTGTGA
GGTATCTTCGGAGAAAGGCTGTAACATGGAATTGGACGTTAAAAACATGG
GTAAATTTACACACAAAAATAGTATTTTAGGGGTTAAGAAGTCGGAATTT
ACCGTTAGAGCGAATTGTTATGATGATCCTGACCTTAAAAATGAAGTTGC
TCAGATTTCTGAAACTACACTCAGTATCGACGGGAATAAAAATAAAACCG
TCTCTATACCAATCAAACTCACAGGATCACTCGCTAGTGAAAAAGGATAC
TGCAACATCATTCTCCTTTCCGGAAAGAAGGAGATGTTGGATGGTATGAA
GATGGAGATAAAGGTGAAGGTGAAGAAGGAGACGTTTGGTAAGGATCCGG
TTAAGGTCCAGGATATAGTGGCTGCTCCTAGTCCTAAGGATAAATTAACC
ACTCCTCAAGTGATTAACCCGATTGTCATTAACCAACCCGGGTCTAAAAA
TGACACTAAAAAAGAGGAAGAGTCACAATGCAAATGCGCGTCCTGGAATA
TCTTCTGCATGCTCATCAACTTTAAGATATGTGTTTCGTCTTATGTGAGT
AAGGTATTATTTTACGTGTTGATTGCACTTGGAATTTTATTGCTTTTGAT
TTTGTTGCCGGTGTTGATTCCGTTAATTGTTAGTCTCTTTAAGGCTCTCG -continued

CTGGACTCATCAAAACACCACTCGAAGCCCTCGAACAAAGAAGATTAAAG

AAAAAAAACAATACACAACTTGAAGTTTAA

Eimeria tenella (SEQ ID NO.: 23)
GCAGCTGCTGCTGCTGCGGCTGCAGCCTCCCGCAGTGTCTCGACACATCA

GTAGCAACGTGCTGCCGCAAATGAATTTTTATTTGTGGCTTCTAGGGGTA

GGCTTGTATACCCCTTCACTGCAGCAGCAGATGATGATACCGTCTCGGAA

CAGGGTTTTCATTTTGACGCTACATGGTTTGCGCGGTCTCGAGCAAAGAA

TGTCAATTCCGATTGTGGCACTTCAAGCTACGGTAATGCTTTACGTGACG

AAGTGCTTTTCCAGTTCTTTCTCCCGATGAGCTTTTTAATTTCAGGCTCA

CCATTTTGTAACCCTAAGAGCTGTCTGAGGCATATGATCGTCCTAGACGA

ACAACACGTCACAGTGGATGGCAGCACGTGTGATCTCCCGGGAGTTTCAC

TGCAGCAATGGGGAAGAGACGGCTTTTGTGATTACGCACAAGGAACGTGC

TTTGCGAAAAACTTGAAGTGGTTTCATGAATACAACGAACAGGCCGCA

Leishmania major (SEQ ID NO.: 24)
ATGGGGGGCACCGCCACGGCAACGGCCTACGTGCGGTCCTGCGACGGAGC

CTCGCCACCCACGCCGCCTGGGTGCGGGCTCAAGCTGGTGGTGGACCTCA

CCCTCGACGACAGCATTCTCACCGGCTCCGTCTTGGAGACAGAGGTGATG

GTGACGCACGCGTTGCATGAGTCACTCTTTCCCCGTGACGCGGCGTCCGA

TGCCGCTGGCACAGCTGCCACCTCTCTGCAGGTGTCTCTGCCTCCCATCA

CGGTGGCAATGCGGCGTGGCGCTGTGCAGATGCGCTACGGGCTCACCTAC

CTACGCACGTTCCCGGCGGCATTGCGAGACTCTGTGCGGGTACTGAAGAC

GGCCATGTCGTGCGACGACGGCGTCACGCGCTGTCCTTCCTACATGAGCA

TGACAGGGACGCTTGTGTCGGCGCCGCTCGGATTGTGCTGCCTCTGCACC

AGCGTGGAGTGCGCCCTCACAAGCGACCTGTGCAACGCTTCGATGCGCGC

GCACTTTTGCTTCCGCACCGGTGCAGCCGGAATCACGTGCGTACAGAGCG

AGGGCATCACCTACCACGGATGGGCCGTGGGATCGTCGTCGCCCTACTAC

ATGATGCACCTATCCGCGAGCGGGCGAGGGATCGCACCGACGACACTGCA

GCTCACGACGGACGCCCCTGAGGTGCAGAAGGGTGCGTCTGCTCTGCAGA

TTCTTCGGGCCTCTGGTGTTTTGCCCGGAGAGTCAAACCCCACGGTTGAT

ATTTCCGGGCGCGTTCTCTTTGTCCCCTCTGCAGAACACAGCAGTGCCAG

CCGCAGCATCAGCACCGGGCCTGTGCGCGACGACGACCCGGCAGAGTGGC

TGTTGCTCCCGGCGCCGCTTGTCAGCGTCTCCGGCAATGATTGCGACAAG

GTCGGCATCTCACCAGACTATTTCTACTCGCTCTCCAGCACTAAGCAGTG

CAACGCGCAGAAGGGGACGTGCGTGCGACACCAGCTAGCAGACTACCGTG

CGGCGGACCTGGAACAGATCGCCCAGGGCGTCGGCGGACGCTATATCGCC

GCCTCTCTGGGCACCTTCACGCGGCAGGCGATGAGGGAACAGGAGTTCCT

GCTCGATGCGGTGGAGCGCACGGGTGGGGCGATGCTGCGGTGGACGGTGA

ATGCGGACGGCCTCGTGTTCCAGCCGCTTCCGGTACACGGTGTACTGGAT

GCTATCAAGTTTGACAGCAGCACAGGCATCCTCTACGTCACGGTTCGCAA

CAACAACACATATGGTGGCCTCTACTACGTTGCCGTTGGTCAGTGTCGGG

GAGCACGCGCATCGAACTGCGATAGCGACGGCGTGACACACGAGTGTGGT

CGCACGGCTTTGGTGGCCGGGGCTAACACCTCCTCGCTGTTGCAGTTCAG

CATGGTGAGCGACCTGCCCGAGGAGGTGGGGAGCACCGCCTCATGCACCG

TCGTCTTTCGCGACGCGGCCGCAGCGCTGCTGGCCTCTGCAAACATTTCC

TGGACGGTCGAGCACACGACCACTACGCCGGCGCCGAATGCCCCCAAAGC

GGAGCAGTGCAGACGCTGCGCCTTTCGCGACCTGCGGTGTCTTTTCAGCA

CCGTCTGCGAGTGGCAGATGCTCCTGTGGACAGCGGTGGCGGTGGCGGTG

ACGTGGACGCCGTATGCCATCTTGGCCTACTGGCGTATGGCGTGGCACGT

TGGCGCCAAGCTCTTGGCGTGTCTGAACTGA

CrFusM recombinant protein sequence (confirmed by mass spectrometry).

(SEQ ID NO.: 25)
MRGSHHHHHHGSACELHAEVIASGRLEKCVVDGVTEELDCQEKVVVTLTV

GNGQSLQTEALEFSLSCLNSPDGRCPCSCSAADPTCACRDLAAPLRVSLT

KSPLWASYPLQYLSSFNWKPLEVILRPSNKVCKDGDWEDSPTCGWFSQGG

VRVADSQGFCCECSSSQVWDDTFGSSKERTRANLDCDFWSDPLDILIGRK

PVSAHCLTFDPQWYSGYELGAASLQFEIAITVEVPTAPSPTTATTSATPR

TNNSSSANSTNSTNSPAPQFLSPPAPSTREVLHLGPSVPLASSASRLLSA

KLLGDLAMYTQLPAISNQVLMVPQPPAAAAATGSPLDATLATNRSAWMLL

DKTMLSMDGLACDKVGTGFSAFRYQPSGCGRAPQACLSGQLKDLWEADLA

RIADGRVPLYMITRFTGGSDTTLQSFSGGPLSFALPVTSHSQSLVTLSVA

ADGVRLVTNRSPGKITGAAVCRFAGTSCGGFEAVAARGYIYVNITNTGRL

DSDYTLTVSNCSSNVRPIEARTLAVRAGSAASLDPPMELYVEDQAAAAAR

TCTVSLYDSVGAVTDSLTLSFYTNATQLVVKPSGGYNGTGDGAGVKRNGT

DCSTACTNPIDVLCFVTKKCWSKFGRLLGHGGALVGLGLLAVALKFGWLA

SLAASCCGGGGAAAGGAGGGMGLGTGGGGGCFGGGQQQQ

DNA constructs sequence for expressing recombinant protein. FusM cDNA of Chlamydomonas was cloned into pQE30 vector (Qiagen) to generate pYJ61. PYJ61 DNA construct sequence (SEQ ID NO.: 26).

CTCGAGAAATCATAAAAAATTTATTTGCTTTGTGAGCGGATAACAATTAT

AATAGATTCAATTGTGAGCGGATAACAATTTCACACAGAATTCATTAAAG

AGGAGAAATTAACTATGAGAGGATCGCATCACCATCACCATCACGGATCC

GCATGCGAGCTCCACGCTGAGGTCATTGCAAGTGGGCGCTTGGAAAAATG

CGTCGTCGATGGTGTTACCGAGGAGCTGGACTGCCAGGAGAAGGTGGTGG

TGACACTGACGGTCGGAAATGGGCAGAGCCTGCAGaCCGAGGCTCTGGAA

TTCTCGCTCAGCTGCCTCAACAGCCCCGACGGACGCTGCCCCTGCAGCTG

CAGCGCCGCCGACCCTACTTGCGCATGTCGTGACCTGGCGGCGCCGCTGC

GCGTGTCGCTTACCAAGTCGCCGCTGTGGGCCTCCTACCCGCTGCAGTAC

TTGTCGTCCTTTAACTGGAAACCCCTGGAAGTCATCCTGCGCCCCAGCAA

CAAAGTTTGCAAGGACGGCGACTGGGAGGACTCGCCCACGTGTGGCTGGT

TCAGCCAGGGCGGTGTGCGGGTGGCGGACAGCCAGGGATTCTGCTGCGAG

-continued

```
TGCAGCAGCAGCCAGGTGTGGGACGACACCTTCGGGTCCAGCAAGGAGCG
CACTCGCGCCAACCTGGACTGTGACTTCTGGAGCGACCCACTGGACATAC
TGATTGGCCGCAAGCCGGTGTCCGCACACTGCCTCACATTCGACCCGCAG
TGGTACAGCGGCTATGAGCTGGGCGCCGCCTCGCTGCAGTTCGAGATCGC
CATCACCGTGGAGGTACCCACCGCCCCCTCCCCCACCACAGCCACCACCT
CCGCCACTCCCCGCACCAACAACAGCAGTAGCGCCAACAGCACCAACAGC
ACCAACAGCCCGGCGCCGCAGTTTCTGTCCCCGCCTGCGCCCAGCACGCG
GGAAGTGTTGCATCTGGGTCCCTCGGTGCCTCTGGCCAGCAGCGCGAGCC
GCCTGCTGTCCGCCAAGCTGCTGGGCGACCTGGCCATGTACACACAGCTG
CCCGCaATCAGCAACCAGGTGCTGATGGTGCCGCAGCcGCCAGCCGCCGC
CGCCGCCACCGGCTCGCCCCTGGACGCCACCCTGGCGACCAACCGCTCCG
CCTGGATGCTGCTGGACAAGACCATGCTCAGCATGGACGGCCTGGCCTGC
GACAAGGTGGGGACCGGCTTCTCAGCCTTCCGCTACCAGCCCAGCGGCTG
CGGCCGTGCCCCTCAGGCCTGTCTGTCCGGCCAGCTCAAGGACCTGTGGG
AGGCGGACCTGGCGCGTATCGCGGACGGCCGGGTGCCGCTGTACATGATC
ACCAGGTTCACTGGCGGCAGCGACACCACGCTGCAGTCCTTCTCCGGGGG
CCCGCTGTCGTTCGCGCTGCCTGTCACCAGCCACAGCCAGAGCCTGGTGA
CGCTGAGTGTGGCGGCGGACGGCGTGAGGCTGGTCACCAACCGCAGCCCG
GGCAAGATTACAGGCGCGGCGGTGTGCCGTTTCGCCGGCACTTCCTGTGG
CGGCTTTGAGGCGGTGGCAGCTCGCGGCTACATCTACGTCAACATCACCA
ACACCGCCGCCTGGACAGTGACTACACACTCACAGTGTCCAACTGCTCG
TCCAACGTGCGGCCCATCGAGGCGCGCACACTGGCCGTACGCGCGGGATC
CGCCGCCAGCCTGGATCCGCCCATGGAGCTGTACGTGGAGGACCAGGCGG
CAGCGGCGGCGCGCACGTGCACAGTCAGCCTGTACGACTCAGTCGGCGCG
GTGACGGACTCGCTCACGCTGTCCTTCTACACAAACGCCACCCAGCTGGT
CGTCAAGCCCTCCGGCGGGTACAACGGCACGGGGGACGGCGCGGGCGTAA
AGCGCAACGGCACCGATTGCAGCACGGCCTGCACCAACCCGATTGACGTG
CTGTGCTTCGTGACCAAGAAGTGCTGGTCCAAGTTCGGGCGGCTTCTGGG
CATCATCGGCGGCGCCCTGGTGGGGCTGGGGCTGCTGGCAGTAGCACTCA
AGTTCGGGTGGCTGGCCTCCCTGGCGGCCTCGTGTTGTGGGGAGGAGGA
GGAGCAGCAGCAGGCGGGGCTGGAGGCGGCATGGGGCTGGGGACCGGCGG
CGGCGGAGGCTGTTTTGGAGGCGGGCAGCAGCAGCAGCAGCCTGCTGCTA
GCCATGCCATGTCGCCACCGCAGCAGCAGCAGCAGCGCTCGCATGCGGAG
GTGGCAGCAGGGGCTGCAGTGGCAGGAGCAGGAGCCGCTGTTGCAGCAGC
GGCGGTGCTGGGAGCCAAACACGGCGGCGGCGGCGGCGCTCGTGGCAAGC
AGCAGCATACCGACACCCGGCATTTGCAGGATCGCGACTCACGAGCCACC
GCCGACGGAGCAAGCATTGACAGCAGCAGCGCCGGCGGCAGTAGCAGTTT
AAGCAGCTACACCCAGCCTCGTAAGGCCGGAGGCAGGCTGCTGCAGCCGC
CGGCAGCAGCAGTGTTTGTGCCTGAAGGCGGCATCACTAGTGAATTCGCG
GCCGCCTGCAGGTCGAAGCTTAATTAGCTGAGCTTGGACTCCTGTTGATA
GATCCAGTAATGACCTCAGAACTCCATCTGGATTTGTTCAGAACGCTCGG
TTGCCGCCGGGCGTTTTTTATTGGTGAGAATCCAAGCTAGCTTGGCGAGA
TTTTCAGGAGCTAAGGAAGCTAAAATGGAGAAAAAAATCACTGGATATAC
CACCGTTGATATATCCCAATGGCATCGTAAAGAACATTTTGAGGCATTTC
AGTCAGTTGCTCAATGTACCTATAACCAGACCGTTCAGCTGGATATTACG
GCCTTTTTAAAGACCGTAAAGAAAAATAAGCACAAGTTTTATCCGGCCTT
TATTCACATTCTTGCCCGCCTGATGAATGCTCATCCGGAATTTCGTATGG
CAATGAAAGACGGTGAGCTGGTGATATGGGATAGTGTTCACCCTTGTTAC
ACCGTTTTCCATGAGCAAACTGAAACGTTTTCATCGCTCTGGAGTGAATA
CCACGACGATTTCCGGCAGTTTCTACACATATATTCGCAAGATGTGGCGT
GTTACGGTGAAAACCTGGCCTATTTCCCTAAAGGGTTTATTGAGAATATG
TTTTTCGTCTCAGCCAATCCCTGGGTGAGTTTCACCAGTTTTGATTTAAA
CGTGGCCAATATGGACAACTTCTTCGCCCCCGTTTTCACCATGGGCAAAT
ATTATACGCAAGGCGACAAGGTGCTGATGCCGCTGGCGATTCAGGTTCAT
CATGCCGTCTGTGATGGCTTCCATGTCGGCAGAATGCTTAATGAATTACA
ACAGTACTGCGATGAGTGGCAGGGCGGGGCGTAATTTTTTTAAGGCAGTT
ATTGGTGCCCTTAAACGCCTGGGGTAATGACTCTCTAGCTTGAGGCATCA
AATAAAACGAAAGGCTCAGTCGAAAGACTGGGCCTTTCGTTTTATCTGTT
GTTTGTCGGTGAACGCTCTCCTGAGTAGGACAAATCCGCCGCTCTAGAGC
TGCCTCGCGCGTTTCGGTGATGACGGTGAAAACCTCTGACACATGCAGCT
CCCGGAGACGGTCACAGCTTGTCTGTAAGCGGATGCCGGGAGCAGACAAG
CCCGTCAGGGCGCGTCAGCGGGTGTTGGCGGGTGTCGGGGCGCAGCCATG
ACCCAGTCACGTAGCGATAGCGGAGTGTATACTGGCTTAACTATGCGGCA
TCAGAGCAGATTGTACTGAGAGTGCACCATATGCGGTGTGAAATACCGCA
CAGATGCGTAAGGAGAAAATACCGCATCAGGCGCTCTTCCGCTTCCTCGC
TCACTGACTCGCTGCGCTCGGTCTGTCGGCTGCGGCGAGCGGTATCAGCT
CACTCAAAGGCGGTAATACGGTTATCCACAGAATCAGGGGATAACGCAGG
AAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTG
GCGCTTTCTCAATGCTCACGCTGTAGGTATCTCAGTTCGGTGTAGGTCGT
TCGCTCCAAGCTGGGCTGTGTGCACGAACCCCCCGTTCAGCCCGACCGCT
GCGCCTTATCCGGTAACTATCGTCTTGAGTCCAACCCGGTAAGACACGAC
TTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTC
GGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAAC
```

```
-continued
GAAAACTCACGTTAAGGGATTTTGGTCATGAGATTATCAAAAAGGATCTT

CACCTAGATCCTTTTAAATTAAAAATGAAGTTTTAAATCAATCTAAAGTA

TATATGAGTAAACTTGGTCTGACAGTTACCAATGCTTAATCAGTGAGGCA

CCTATCTCAGCGATCTGTCTATTTCGTTCATCCATAGCTGCCTGACTCCC

CGTCGTGTAGATAACTACGATACGGGAGGGCTTACCATCTGGCCCCAGTG

CTGCAATGATACCGCGAGACCCACGCTCACCGGCTCCAGATTTATCAGCA

ATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTA

GTTCGCCAGTTAATAGTTTGCGCAACGTTGTTGCCATTGCTACAGGCATC

GTGGTGTCACGCTCGTCGTTTGGTATGGCTTCATTCAGCTCCGGTTCCCA

ACGATCAAGGCGAGTTACATGATCCCCCATGTTGTGCAAAAAAGCGGTTA

GCTCCTTCGGTCCTCCGATCGTTGTCAGAAGTAAGTTGGCCGCAGTGTTA

TCACTCATGGTTATGGCAGCACTGCATAATTCTCTTACTGTCATGCCATC

CGTAAGATGCTTTTCTGTGACTGGTGAGTACTCAACCAAGTCATTCTGAG

AATAGTGTATGCGGCGACCGAGTTGCTCTTGCCCGGCGTCAATACGGGAT

AATACCGCGCCACATAGCAGAACTTTAAAAGTGCTCATCATTGGAAAACG

TTCTTCGGGGCGAAAACTCTCAAGGATCTTACCGCTGTTGAGATCCAGTT

CGATGTAACCCACTCGTGCACCCAACTGATCTTCAGCATCTTTTACTTTC

ACCAGCGTTTCTGGGTGAGCAAAAACAGGAAGGCAAAATGCCGCAAAAAA

GGGAATAAGGGCGACACGGAAATGTTGAATACTCATACTCTTCCTTTTTC

AATATTATTGAAGCATTTATCAGGGTTATTGTCTCATGAGCGGATACATA

TTTGAATGTATTTAGAAAAATAAACAAATAGGGGTTCCGCGCACATTTCC

CCGAAAAGTGCCACCTGACGTCTAAGAAACCATTATTATCATGACATTAA

CCTATAAAAATAGGCGTATCACGAGGCCCTTTCGTCTTCAC
```

General Methods. *Plasmodium*: Deletion of the FusM gene: To replace all protein-coding sequence of the FusM gene (GenBank accession number XM_671808) with a T gondii dhfr/ts expression cassette conveying resistance to pyrimethamine, a targeting vector was constructed in plasmid pBS-DHFR[1]. A 736 bp fragment comprising 5' flanking sequence immediately upstream of the start codon was amplified from *P. berghei* genomic DNA using primers ol527 (5'-CCCCGGGCCCGCGCGTTATTATTATTCGGGC (SEQ ID NO.: 27), restriction site underlined) and ol528 (5'-GGGG AAGCTTTTTTTCTAAATGAAATATTAAAGAATGGC) (SEQ ID NO.: 28) and inserted into ApaI and HindIII restriction sites upstream of the dhfr/ts cassette of pBS-DHFR. A 967 bp fragment of 3' flanking sequence was then generated using primers ol529 (5'CCCC GAATTCATTACATGGAATAGTATTTGCAAATTTG) (SEQ ID NO.: 29) and ol530 (5'-GGGG TCTAGACAATATACATGCTGATAACCTCC) (SEQ ID NO.: 30) and inserted downstream of the dhfr/ts cassette using EcoRI and XbaI restriction sites. The replacement construct was excised as a ApaI/XbaI fragment and used for the electroporation of cultured *P. berghei* schizonts as described[2]. Following dilution cloning of drug resistant parasites, genotyping of two fusm clones was done by Southern blot hybridization on EcoRI digested genomic DNA using the ApaI/HindIII fragment of 5' targeting sequence as a probe. Diagnostic PCR analysis used primers ol525 (5'-CTC-GAATATGTAGATATATCCAGATG) (SEQ ID NO.: 31) and ol526 (5'-CAGAGATGTTATAGCTAGTGATATAAC) (SEQ ID NO.: 32) specific for FusM, and primers ol524 (5'-CTAAGTAGCAACTATTTTGTAAAATTATATC) (SEQ ID NO.: 33) and ol170[3] to span the predicted 5' integration site.

RT-PCR analysis of FusM expression: *P. berghei* RNA was isolated from equivalent numbers of purified wild type and fusm gametocytes and strain 233 asexual parasites using TRIzol reagent (Invitrogen) according to the manufacturer's protocol. Any residual gDNA was removed by treatment with RQ1 RNase-free DNase (Promega) and the resulting RNA was extracted with phenol/chloroform, precipitated with ethanol, resuspended in DEPC-treated water, and quantified by 0.8% agarose gel electrophoresis. First-strand cDNA synthesis from one µg of total RNA was done with M-MLV Reverse Transcriptase (Invitrogen) at 37° C. for 50 min. Following heat inactivation for 15 min at 70° C., 2 µl of cDNAs were used per PCR reaction. Primers selected to amplify sections of the FusM ORF (spanning the 209 bp intron) were: Forward: 5'-GCA TAA GAT TCA CAA ATA CAA AAA GG (SEQ ID NO.: 34) and Reverse: 5'-GGT CTT CCT CTA AGT ATT-3' (SEQ ID NO.: 35). The expected RT amplicon was 1203 bp, whereas the gDNA amplicon was 1412 bp. The ubiquitously expressed alpha tubulin gene PB300720.00.0 was amplified for each sample to ensure amplifiability of cDNA from respective RNA samples (Forward: 5'-CCA GAT GGT CAA ATG CCC-3' (SEQ ID NO.: 36) Reverse 5'-CTG TGG TGA TGG CCA TGA AC-3') (SEQ ID NO.: 37). The expected products were 432 bp (cDNA) and 592 bp (gDNA). Thirty RT-PCR cycles were carried out with denaturation at 94° C. for 1 min, annealing at 50° C. for 45 s, and extension at 68° C. for 1.5 min and products visualised on a 0.8% agarose gel.

*Chlamydomonas*: Insertional mutagenesis and TAIL-PCR: Insertional mutants were generated using the plasmid pSI103 linearized with PvuII and transformed into B215 cells using the glass bead method with selection on agar plates containing 10 µg/ml paromomycin (Sigma, St. Louis, Mo., United States) in M medium[4,5]. Approximately 2500 transformed colonies were induced to undergo gametogenesis by transferring them into 96 well plates containing M-N medium. After agitation on a reciprocal shaker for 2 h, 5 µl from each well was transferred into a duplicate 96 well plate containing M media to maintain a stock of the cells in vegetative growth. After continued agitation overnight, samples from each well of the plate with M-N were mixed with wild-type mt+ gametes. Each well was scored on an inverted microscope for flagellar agglutination at 10 min, 4 h, and 12-18 h. Zygote formation, as determined by the presence of large aggregates of zygotes visible in the inverted microscope, was assessed at 4 h and 12-18 h. The absence of zygotes in mixtures with 63B10 was confirmed by phase contrast microscopy.

PCR and TAIL-PCR (Thermal Asymmetric Interlaced PCR): TAIL-PCR was used to identify genomic sequence in the 5'-flanking region of the inserted aphVIII plasmid in clone 63B10 cells. The specific, nested primers were the following: primary: Aph.p22 (5'-GCGCCCTCATAGCCCGC-CAAATC) (SEQ ID NO.: 38); secondary: Aph.p21 (5'-CCGCCAAATCAGTCCTGTAGCTTC) (SEQ ID NO.: 39); and tertiary: Aph.p20 (5'-TGCGCGCTTGGCGTAAT-CATGGTC) (SEQ ID NO.: 40). The arbitrary degenerate primer was Ad.p24 [(G/C)TAGA(G/C)T(G/C)A(G/C)C(A/T)CA(G/C)] (SEQ ID NO.: 41) (personal communication, Carolyn Silflow, University of Minnesota, St. Paul, Minn.). For the tertiary reaction, primers aph.p20 and aph.p21 were used. The PCR product from the tertiary reaction, which was cloned and sequenced, is the following (single underlined sequence is C_530033; dashed underlined sequence is an *E. coli* cytosine methylase presumably from the plasmid host bacterium; and the non-underlined sequence is from the aph-VIII plasmid): (5'-CCGCCAAATCAGTCCTGTAGCTTC-CATATCTGATTCGCAATCTTGCCTTG-CACCTGCCTGCCACGCTCATACCATGTCGCCGTGAC CCCAAAACAGGCCTGTCTGTCCGGC-CAGCTCAAGGACCTGTGGGAGGCGGAC-CTGGCGCGTACCGCGGACGGCCGGGTGC-CGCTGTACATGATCACCAGGTTCACTGGCGGCAGC GAGGGCTAATCGCGCCG GAAAATATATCAGTAAC-CGATTCATACAGCACCGGGAATGCCGCA-CAGGCAATG CTGGAGAAACTGCTGCAAATTTAT-GATGTTAAAACGTTGGTGGCGCAGCTTAATG GTGTAGGTGAGAATCACTGGAGCGCG-GCAATTTTAAAACGTGCGCTGGCGAATG ACTCG-GCATGGCACCGTTTAAGTGAGAAAGAGT-TCGCCCATCTGCAAACGTTATT ACCCAAACCACCGGCACATCATCCGCAT-TATGCGTTTCGCTTTATCGATCTATTC GCCGGAAT-TGGCGGCATCCGTCGCGGTTTTGAATC-GATTGGCGGACAGTGCGTGT TTTCCAGCGAATGGAACAAACATGCGG-TACGCACTTATAAAGCCAACCATTATT GCGATCCG-GCGACGCATCATTTTAATGAAGATATC-CGCGACATCACCCTCAGCC ATAAAGAAGGCGTGAGTGATGAGGCG-GCGGCGGAACATATTCGTCAACAATTTC ACACAG-GAAACAGCTATGACCATGATTACGCCAAGCGCGCA) (SEQ ID NO.: 42). Other primers used for PCR were the following: FusM.p1 (5'-ATGTCGCCGTGACCCCAAAA-CAG) (SEQ ID NO.: 43); FusM.p2 (5'-CTGGCTGGTGA-CAGGCAGCGCGAA) (SEQ ID NO.: 44); and Aph.p17: (5'-TTGGCTGCGCTCCTTCTGGCGC) (SEQ ID NO.: 45).

Transformation of *Chlamydomonas* with FusM constructs: FusM-HA: The 8.3 kb SstI fragment from DNA BAC clone 20L3 obtained from the Clemson University Genomics Institute, Clemson University containing gene model C_530033 was inserted into the SstI site of pUC119 to generate pYJ36. Standard methods were used to insert a PCR product encoding three copies of the 9-amino acid hemagglutinin (HA) epitope[7] into the NheI site of pYJ36 to generate pYJ58. To obtain 63B10 cells containing the FusM-HA construct, we carried out co-transformation with the glass bead method using pYJ58 and plasmid pmn56 encoding the nitrate reductase gene[8]. For the experiment shown in FIG. 1*b*, 63B10 cells were co-transformed with the gel-purified 8.3 kb Sst1 fragment of BAC clone 20L3 and pmn56. Transformants were selected for their ability to undergo fusion with wt mt+ gametes.

Generation of an mt+ strain containing only disrupted FusM: 63B10 gametes rescued for fusion by transgenic HA-tagged FusM protein were crossed with 21gr gametes and the progeny were grown using procedures described previously[9]. Colonies formed by germinated zygotes on 2% agar plates were pooled and inoculated into a growth flask containing M Media. Progeny cells were sub-cloned on agar selection plates containing 10 µg/ml paromomycin and screened for mt+ progeny that contained the disrupted fusm allele from the 63B10 cells and lacked both the wt allele and the FusM-HA insert. To confirm the genotype of the transformant, Southern blotting was carried out with genomic DNA digested with NotI. The probe was a cloned PCR product generated using p21 and aph.p20 primers with 63B10 genomic DNA as template and labeled using a Random Primed DNA labeling kit (Roche Applied Science).

Indirect immunofluorescence: Gametes were washed with MT buffer (30 mM Tris-acetate, pH 7.3, 5 mM MgSO4, 5 mM EDTA, 25 mM KCl, 1 mM dithiothreitol) and loaded onto 8-well slides coated with 0.1% polyethylenimine for 10 min[10]. Cells were fixed in 100% ice-cold methanol at −20° C. for 20 min, washed 3 times for 5 min in PBS, and blocked for 30 min with blocking serum (1% cold water fish gelatin, 0.1% bovine serum albumin, 5% goat serum in PBS). The slides with fixed cells were incubated with rat monoclonal anti-HA antibody (Roche Applied Science, diluted 100-fold) for 2 h, rinsed three times in PBS and then incubated for 1 h with fluorescein-conjugated goat anti-rat IgG (ICN/CAPPEL, 1:400 dilution) in blocking serum. The slides were rinsed in PBS and mounted in Fluoromount-G (Southern Biotech, Birmingham, Ala.). Fluorescence microscopy was performed using an Ultraview ERS spinning disk confocal microscope (Perkin Elmer). Final composite images were constructed using Image J (NIH, USA) and Adobe Photoshop (Adobe Systems, San Jose, Calif.).

Assessing gamete activation: To test whether 63B10 gametes were capable of gamete activation, 250 µl of 63B10 gametes at 1.6×10[7] cell/ml were mixed for 30 min with an equal number of 21gr (mt+) gametes, with dibutyryl cAMP, or with flagella isolated from 21gr gametes. For the experiment with isolated flagella, 10 cell equivalents of flagella were added at 5 min intervals[11]. Cell wall loss was determined as previously described[11]. The data shown are averages from three independent experiments, each done in duplicate, and the error bars are s. e. m.

Sequence analysis: PSI-BLAST[12] was used to search the nr database (March 15; 4,655,816 sequences; 1,607,282,285 total letters) for FusM homologs. The query sequence was FusM protein from *Chlamydomonas reinhardtii* (accession number: ABO29824) and the inclusion e-value cutoff was 0.001. NCBI Accession numbers for representative sequences found with significant e-values (<0.001) during PSI-BLAST searches are: AAY51998 (*Arabidopsis thaliana*), AB029824 (*Chlamydomonas reinhardtii*), XP_667362 (*Cryptosporidium hominis*), XP_643321 (*Dictyostelium discoideum* A), XP_645269 (*Dictyostelium discoideum* B), ABN45755 (*Hydra magnipapillata*), XP_843157 (*Leishmania major* A), AAY42350 (*Leishmania major* B), BAE71142 (*Lilium longiflorum*), NP_001055054 (*Oryza sativa*), BAE71144 (*Physarum polycephalum*), XP_676900 (*Plasmodium berghei*), NP_700613 (*Plasmodium falciparum*), XP_725086 (*Plasmodium yoelii*), XP_001030543 (*Tetrahymena thermophile*), XP_764209 (*Theileria parva*), XP_973371 (*Tribolium castaneum*), XP_823296 (*Trypanosoma brucei*), and XP_814894 (*Trypanosoma cruzi*). FusM proteins were also retrieved from publicly available genome databases for the following species: *Cyanidioschyzon merolae* (CMK076C)[13], *Monosiga brevicollis* (8819: genome.jgi-psf.org/Monbr1/Monbr1.info.html), *Naegleria gruberi* (genome.jgi-psf.org/Naegr1/Naegr1.home.html), *Nematostella vectensis* (genome.jgi-psf.org/Nemve1/Nemve1.home.html), *Paramecium tetraurelia, Toxoplasma gondii* (9840; Preliminary sequence data was obtained from The Institute for Genomic Research website at www.tigr.org.), and *Volvox carteri*, the relevant sequences for which are incorporated herein by reference. Each of these FusM proteins shows significant sequence similarities to FusM proteins available in NCBI databases (PSI-BLAST e-value<0.001). The *V. carteri* genome sequencing work was performed by the Joint Genome Institute (www.jgi-.doe.gov/) under the auspices of the US Department of Energy's Office of Science, Biological and Environmental Research Program and the University of California, Lawrence Livermore National Laboratory under Contract No. W-7405-ENG-48, Lawrence Berkeley National Laboratory under contract No. DE-ACO3-765F00098 and Los Alamos National Laboratory under contract No. W-7405-ENG-36 and was provided for use in this publication only. The *Apis mellifera* FusM was assembled by searching the *Apis mellifera* genome sequences using TBLASTN and based on comparison with the *Tribolium* FusM. A TBLASTN search starting from *Arabidopsis thaliana* FusM (accession number: AAY51998) against the est others database in NCBI found several *Zea mays* est sequences (gi|76914610, gi|26457309, gi|78074749, and gi|76936583) with significant e-values (<0.001), that are likely to be FusM homologs. The maize protein was not included in the alignment or the phylogenetic analysis due to the partial sequence.

Multiple sequence alignment of FusM protein homologs was generated by PROMALS (available at prodata.swmed.edu/promals)[14] (FIG. S1), which uses information from database homologs and predicted secondary structures to improve alignment quality. For phylogenetic analysis, we removed from the alignment the N-terminal divergent segments including the signal peptide, and C-terminal divergent segments including the transmembrane segments. Highly gapped positions (gap fraction larger than 0.5) were also removed from the alignment. A maximum-likelihood tree (FIG. S2 b) was built using the MOLPHY package (version 2.3). The local estimates of bootstrap percentages were obtained by the RELL method[15], as implemented in the program ProtML of MOLPHY[16]. A quartet puzzling tree was obtained by the TREE-PUZZLE program[17]. Both MOLPHY and TREE-PUZZLE trees were reconstructed with a JTT amino acid substitution model[18]. For the TREE-PUZZLE tree, substitution rate heterogeneity was modeled by discrete gamma distribution with eight rate categories.

METHOD REFERENCES

1. Dessens, J. T. et al. CTRP is essential for mosquito infection by malaria ookinetes. *EMBO J* 18, 6221-7 (1999).
2. Janse, C. J. et al. High efficiency transfection of *Plasmodium berghei* facilitates novel selection procedures. *Mol Biochem Parasitol* 145, 60-70 (2006).
3. Billker, O. et al. Calcium and a calcium-dependent protein kinase regulate gamete formation and mosquito transmission in a malaria parasite. *Cell* 117, 503-514 (2004).
4. Kindle, K. L., Schnell, R. A., Fernandez, E. & Lefebvre, P. A. Stable nuclear transformation of *Chlamydomonas* using the *Chlamydomonas* gene for nitrate reductase. *J Cell Biol* 109, 2589-601 (1989).
5. Fang, S. C., de los Reyes, C. & Umen, J. G. Cell size checkpoint control by the retinoblastoma tumor suppressor pathway. *PLoS Genetics* 2, e167 (2006).
6. Liu, Y. G., Chen, Y. & Zhang, Q. Amplification of genomic sequences flanking T-DNA insertions by thermal asymmetric interlaced polymerase chain reaction. *Methods Mol Biol* 286, 341-8 (2005).
7. Silflow, C. D. et al. The VFL1 Protein in *Chlamydomonas* localizes in a rotationally asymmetric pattern at the distal ends of the basal bodies. *J Cell Biol* 153, 63-74 (2001).
8. Nelson, J. A., Savereide, P. B. & Lefebvre, P. A. The CRY1 gene in *Chlamydomonas reinhardtii*: structure and use as a dominant selectable marker for nuclear transformation. *Mol Cell Biol* 14, 4011-9 (1994).
9. Goodenough, U. W., Hwang, C. & Martin, H. Isolation and genetic analysis of mutant strains of *Chlamydomonas reinhardi* defective in gametic differentiation. *Genetics* 82, 169-86 (1976).
10. Mahjoub, M. R., Qasim Rasi, M. & Quarmby, L. M. A NIMA-related kinase, Fa2p, localizes to a novel site in the proximal cilia of *Chlamydomonas* and mouse kidney cells. *Mol Biol Cell* 15, 5172-86 (2004).
11. Snell, W. J. Study of the release of cell wall degrading enzymes during adhesion of *Chlamydomonas* gametes. *Exp Cell Res* 138, 109-19 (1982).
12. Altschul, S. F. et al. Gapped BLAST and PSI-BLAST: a new generation of protein database search programs. *Nuc Acids Res* 25, 3389-402 (1997).
13. Matsuzaki, M. et al. Genome sequence of the ultrasmall unicellular red alga *Cyanidioschyzon merolae* 10D. *Nature* 428, 653-7 (2004).
14. Pei, J. & Grishin, N. V. PROMALS: towards accurate multiple sequence alignments of distantly related sequences. *Bioinformatics* In Press (2007).
15. Kishino, H., Miyata, T. & Hasegawa, M. Maximum likelihood inference of protein phylogeny and the origin of chloroplasts. *J Mol Evol* 31, 151-160 (1990).
16. Adachi, J. & Hasegawa, M. MOLPHY: version 2.3: Programs for molecular phylogenetics based on maximum likelihood. *Mol Phylogen and Evol* Inst. Stat. Math. Tokyo., 72-6 (1996).
17. Schmidt, H. A., Strimmer, K., Vingron, M. & von Haeseler, A. TREE-PUZZLE: maximum likelihood phylogenetic analysis using quartets and parallel computing. *Bioinformatics* 18, 502-4 (2002).
18. Jones, D. T., Taylor, W. R. & Thornton, J. M. The rapid generation of mutation data matrices from protein sequences. *Comput Appl Biosci* 8, 275-82 (1992).
19. Pei, J. & Grishin, N. V. AL2CO: calculation of positional conservation in a protein sequence alignment. *Bioinformatics* 17, 700-12 (2001).

Attached Table 1. Multiple sequence alignment of FusM proteins generated by PROMALS. Secondary structure predictions are colored (red: alpha-helix; blue: beta-strand) for representative sequences (with cyan sequence names) and consensus secondary structure predictions are shown below the sequences ('h': alpha-helix; 'e': beta-strand). A conservation index number is shown for highly conserved positions (conservation index >=6) above the sequences. Sequence conservation was calculated using the program AL2CO[19]. *Dictyostelium discoideum*, *Leishmania major*, and *Paramecium tetraurelia* have two copies of FusMs labeled as 'A' and 'B'. *Dictyostelium discoideum* B sequence is not complete. We also identified distant homologs of FusM in *Plasmodium* species (not shown in the alignment).

Attached Table 2. a, Phylogenetic tree of FusM proteins generated by MOLPHY. b, Phylogenetic tree of FusM proteins generated by TREE-PUZZLE. Both trees are rooted artificially in the middle of the branch that separates the Apicomplexa species (*Plasmodium*, *Toxoplasma*, *Cryptosporidium*, and *Theileria*) from the rest of the species. Supporting values are shown above or below any internal branch.

It is contemplated that any embodiment discussed in this specification can be implemented with respect to any method, kit, reagent, or composition of the invention, and vice versa. Furthermore, compositions of the invention can be used to achieve methods of the invention. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein.

Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

GENERAL REFERENCES

Billker, O., Dechamps, S., Tewari, R., Wenig, G., Franke-Fayard, B., and Brinkmann, V. (2004). Calcium and a calcium-dependent protein kinase regulate gamete formation and mosquito transmission in a malaria parasite. Cell 117, 503-514.

Billker, O., Lindo, V., Panico, M., Etienne, A. E., Paxton, T., Dell, A., Rogers, M., Sinden, R. E., and Morris, H. R. (1998). Identification of xanthurenic acid as the putative inducer of malaria development in the mosquito. Nature 392, 289-292.

Breman, J. G., Alilio, M. S., and Mills, A. (2004). Conquering the intolerable burden of malaria: what's new, what's needed: a summary. Am J Trop Med Hyg 71, 1-15.

Dessens, J. T., Siden-Kiamos, I., Mendoza, J., Mahairaki, V., Khater, E., Vlachou, D., Xu, X. J., Kafatos, F. C., Louis, C., Dimopoulos, G., and Sinden, R. E. (2003). SOAP, a novel malaria ookinete protein involved in mosquito midgut invasion and oocyst development. Mol Microbiol 49, 319-329.

Ferris, P. J., Woessner, J. P., and Goodenough, U. W. (1996). A sex recognition glycoprotein is encoded by the plus mating-type gene fus1 of *Chlamydomonas reinhardtii*. Mol Biol Cell 7, 1235-1248.

Goodenough, U. W. (1991). *Chlamydomonas* mating reactions, In Microbial Cell-Cell Interactions, M. Dworkin, ed. (New York: American Society for Microbiology), pp. 71-112.

Inoue, N., Ikawa, M., Isotani, A., and Okabe, M. (2005). The immunoglobulin superfamily protein Izumo is required for sperm to fuse with eggs. Nature 434, 234-238.

Johnson, M. A., von Besser, K., Zhou, Q., Smith, E., Aux, G., Patton, D., Levin, J. Z., and Preuss, D. (2004). *Arabidopsis* hapless mutations define essential gametophytic functions. Genetics 168, 971-982.

Reininger, L., Billker, O., Tewari, R., Mukhopadhyay, A., Fennell, C., Dorin-Semblat, D., Doerig, C., Goldring, D., Harmse, L., Ranford-Cartwright, L., and Packer, J. (2005). A nima-related protein kinase is essential for completion of the sexual cycle of malaria parasites. J Biol Chem 280, 31957-31964.

Kindle, K. L., Schnell, R. A., Fernandez, E., and Lefebvre, P. A. (1989). Stable nuclear transformation of *Chlamydomonas* using the *Chlamydomonas* gene for nitrate reductase. J Cell Biol 109, 2589-2601.

Liu, Y. G., Chen, Y., and Zhang, Q. (2005). Amplification of genomic sequences flanking T-DNA insertions by thermal asymmetric interlaced polymerase chain reaction. Methods Mol Biol 286, 341-348.

Milek, R. L., Roeffen, W. F., Kocken, C. H., Jansen, J., Kaan, A. M., Eling, W. M., Sauerwein, R. W., Konings, R. N. (1998). Immunological properties of recombinant proteins of the transmission blocking vaccine candidate, Pfs48/45, of the human malaria parasite *Plasmodium falciparum* produced in *Escherichia coli*. Parasite Immunol 8:377-85.

Misamore, M. J., Gupta, S., and Snell, W. J. (2003). The *Chlamydomonas* Fus1 protein is present on the mating type plus fusion organelle and required for a critical membrane adhesion event during fusion with minus gametes. Mol Biol Cell 6:2530-2542

Mori, T., Kuroiwa, H., Higashiyama, T., and Kuroiwa, T. (2006). Generative Cell Specific 1 is essential for angiosperm fertilization. Nat Cell Biol 8, 64-71.

Pan, J., and Snell, W. J. (2000). Signal transduction during fertilization in the unicellular green alga, *Chlamydomonas*. Curr Opin Microbiol 3, 596-602.

Pollock, S. V., Colombo, S. L., Prout, D. L., Jr., Godfrey, A. C., and Moroney, J. V. (2003). Rubisco activase is required for optimal photosynthesis in the green alga *Chlamydomonas reinhardtii* in a low-$CO_2$ atmosphere. Plant Physiol 133, 1854-1861.

Quakyi, I. A., Carter, R., Rener, J., Kumar, N., Good, M. F., and Miller, L. H. (1987). The 230-kDa gamete surface protein of *Plasmodium falciparum* is also a target for transmission-blocking antibodies. J Immunol 139:4213-7.

Roberts, L. S., and Janovy, J. (2005). Gerald D. Schmidt and Larry S. Robert's Foundations of Parasitology, 7 edn (New York: McGraw-Hill).

Sinden, R. E. (1983). Sexual development of malarial parasites. Adv Parasitol 22, 153-216.

Winger L. A, Tirawanchai, N., Nicholas, J., Carter, H. E., Smith, J. E., and Sinden, R. E. (1988). Ookinete antigens of *Plasmodium berghei*. Appearance on the zygote surface of an Mr 21 kD determinant identified by transmission-blocking monoclonal antibodies. Parasite Immunol. 10:193-207.

What is claimed is:

1. An immunogenic composition comprising: an isolated protozoan FusM mating protein wherein the FusM is selected from SEQ ID NOS: 5-7 and 12-14; and an adjuvant capable of triggering an immune response in an animal.

2. The composition of claim 1, further comprising at least one of a pharmaceutically acceptable salt, an excipient, a preservative, a binder or a pharmaceutically acceptable liquid.

3. The composition of claim 1, wherein the FusM protein is obtained from a protozoan that has been heat-killed, attenuated, chemically-inactivated, mechanically inactivated, lyophilized, vacuum-dried, vacuum heat-dried, freeze-sprayed or combinations thereof.

4. The composition of claim 1, wherein the FusM protein is recombinant and is selected to trigger a cytotoxic T-cell immune response, a humoral immune response, a mucosal immune response or a combination thereof.

5. The composition of claim 1, wherein the FusM protein is inserted for expression in an attenuated bloodstage parasite.

6. The composition of claim 1, wherein the protozoan is selected from the group consisting of the Phylum Apicomplexa or the Class Kinetoplastida.

7. The composition of claim 1, wherein the protozoan is a *Plasmodium* sp.

8. The composition of claim 1, formulated for oral, subcutaneous, intramuscular, nasal, intradermal, pulmonary, intraalveolar, intravaginal, intrarectal, intraperitoneal or intravenous administration.

9. The composition of claim 1, wherein the FusM protein is inserted for expression in an attenuated sporozoite parasite.

* * * * *

UNITED STATES PATENT AND TRADEMARK OFFICE
CERTIFICATE OF CORRECTION

| | |
|---|---|
| PATENT NO. | : 8,216,593 B2 |
| APPLICATION NO. | : 11/856036 |
| DATED | : July 10, 2012 |
| INVENTOR(S) | : William Snell et al. |

It is certified that error appears in the above-identified patent and that said Letters Patent is hereby corrected as shown below:

In the Specification

Column 1, Line 13:
Replace "This invention was made with U.S. Government support under Contract No. R01GM56778-6 awarded by the NIH. The government may have certain rights in this invention." with --This invention was made with government support under grant number GM056778 awarded by The National Institutes of Health. The government has certain rights in the invention.--

Signed and Sealed this
Twenty-third Day of June, 2020

Andrei Iancu
*Director of the United States Patent and Trademark Office*

```
                         SEQUENCE LISTING

<160> NUMBER OF SEQ ID NOS: 45

<210> SEQ ID NO 1
<211> LENGTH: 69
<212> TYPE: PRT
<213> ORGANISM: Chlamydomonas reinhardtii

<400> SEQUENCE: 1

Lys Ser Pro Leu Trp Ala Ser Tyr Pro Leu Gln Tyr Leu Ser Ser Phe
1               5                   10                  15

Asn Trp Lys Pro Leu Glu Val Ile Leu Arg Pro Ser Asn Lys Val Cys
            20                  25                  30

Lys Asp Gly Asp Trp Glu Asp Ser Pro Thr Cys Gly Trp Phe Ser Gln
        35                  40                  45

Gly Gly Val Arg Val Ala Asp Ser Gln Gly Phe Cys Cys Glu Cys Ser
    50                  55                  60

Ser Ser Gln Val Trp
65

<210> SEQ ID NO 2
<211> LENGTH: 69
<212> TYPE: PRT
<213> ORGANISM: Arabidopsis thaliana

<400> SEQUENCE: 2

Lys Ser Ala Ala Tyr Ala Leu Tyr Asp Leu Tyr Thr Ile Arg Asp Val
1               5                   10                  15

Pro Tyr Lys Pro Gln Glu Tyr His Val Thr Thr Arg Lys Cys Glu Pro
            20                  25                  30

Asp Ala Gly Pro Asp Ile Val Gln Ile Cys Glu Arg Leu Arg Asp Glu
        35                  40                  45

Lys Gly Asn Val Leu Glu Gln Thr Gln Pro Ile Cys Cys Pro Cys Gly
    50                  55                  60

Pro Gln Arg Arg Met
65

<210> SEQ ID NO 3
<211> LENGTH: 70
<212> TYPE: PRT
<213> ORGANISM: Lilium longiflorum

<400> SEQUENCE: 3

Lys Ser Ala Ala Tyr Ala Leu Tyr Lys Leu Ile Tyr Leu Arg Asp Val
1               5                   10                  15

Ala Tyr Lys Pro Glu Glu Phe His His Val Glu Thr Arg Arg Cys Glu
            20                  25                  30

Pro Asp Ala Pro Tyr Glu Ile Leu Gly Glu Cys Gln Gly Leu Arg Asp
        35                  40                  45

Gln Asn Gly Asn Ile Ile Glu Asn Thr Gln Pro Val Cys Cys Pro Cys
```

```
                 50                  55                  60

Gly Pro Glu Gly Arg Tyr
 65                  70

<210> SEQ ID NO 4
<211> LENGTH: 64
<212> TYPE: PRT
<213> ORGANISM: Hydra sp.

<400> SEQUENCE: 4

Lys Ser Pro Val Tyr Leu Asn Phe Pro Phe Phe Asn Gly Ile Thr
 1               5                  10                  15

Val Asn Asn Gln Pro Tyr Glu Glu Ile Ile Leu Ser Lys Asn Arg Arg
                20                  25                  30

Gln Cys Leu Asp Asp Glu His Pro Thr Gly Tyr Gln Tyr Thr Arg Ile
            35                  40                  45

Trp Asp Ser Gln Gly Phe Cys Cys Tyr Cys Thr Gln Asp Leu Lys Asn
 50                  55                  60

<210> SEQ ID NO 5
<211> LENGTH: 69
<212> TYPE: PRT
<213> ORGANISM: Trypanosoma brucei

<400> SEQUENCE: 5

Lys Ser Pro Val Gln Tyr Arg Tyr Pro Ile Tyr Tyr Ile Arg Asn Phe
 1               5                  10                  15

Asn Ala Lys Pro Tyr Glu Gln Arg Leu Arg Thr Ser Ala Ser Ser Trp
                20                  25                  30

Cys Asp Asp Ser Ser Asn Pro Gly Ser Ala Thr Val Ala Arg Asp Arg
            35                  40                  45

Arg Gly Asp Val Ile Pro Tyr Ser Gln Gly Phe Cys Cys Leu Cys Gly
 50                  55                  60

Ala Cys Ala Leu Ser
 65

<210> SEQ ID NO 6
<211> LENGTH: 72
<212> TYPE: PRT
<213> ORGANISM: Toxoplasma gondii

<400> SEQUENCE: 6

Lys Thr Pro Val Thr Ile Ser Leu Pro Leu Glu Tyr Ile Lys Glu Val
 1               5                  10                  15

Pro Phe Asp Tyr Arg Glu Glu Ile Tyr Glu Tyr Ser Arg Trp Lys Phe
                20                  25                  30

Cys Tyr Glu Asp Thr Thr Asp Lys Cys Ser Glu Asp Gly Lys Leu Ala
            35                  40                  45

Val His Pro His Gly Lys Pro Leu Ser Trp Ala His Gly Arg Cys Cys
         50                  55                  60

Trp Cys Ser Glu Val Leu Ala Phe
 65                  70

<210> SEQ ID NO 7
<211> LENGTH: 67
<212> TYPE: PRT
<213> ORGANISM: Plasmodium berghei

<400> SEQUENCE: 7

Arg Asp Tyr Val Thr Val Ser Tyr Tyr Leu Lys Tyr Val Lys Asp Ile
```

```
                   1               5                  10                 15
Pro Leu Glu Phe Arg Glu Ile Ile Asp Ile Phe Asn Asn His Gln Tyr
                        20                 25                 30

Thr Gln Glu Gln Ile Asn Lys Tyr Thr Tyr Thr Cys Asn Val Arg Lys
            35                 40                 45

Ile Phe His Glu Tyr Thr Arg Gly Glu Ala Cys Arg Cys Gln Thr Tyr
        50                 55                 60

Asn Tyr Phe
65

<210> SEQ ID NO 8
<211> LENGTH: 75
<212> TYPE: PRT
<213> ORGANISM: Chlamydomonas reinhardtii

<400> SEQUENCE: 8

Ser Ala Trp Met Leu Leu Asp Lys Thr Met Leu Ser Met Asp Gly Leu
1               5                  10                 15

Ala Cys Asp Lys Val Gly Thr Gly Phe Ser Ala Phe Arg Tyr Gln Pro
            20                 25                 30

Ser Gly Cys Gly Arg Ala Pro Gln Ala Cys Leu Ser Gly Gln Leu Lys
        35                 40                 45

Asp Leu Trp Glu Ala Asp Leu Ala Arg Ile Ala Asp Gly Arg Val Pro
    50                 55                 60

Leu Tyr Met Ile Thr Arg Phe Thr Gly Gly Ser
65                 70                 75

<210> SEQ ID NO 9
<211> LENGTH: 75
<212> TYPE: PRT
<213> ORGANISM: Arabidopsis thaliana

<400> SEQUENCE: 9

Ser Met Trp Met Leu Leu Glu Arg Val Arg Phe Thr Leu Asp Gly Leu
1               5                  10                 15

Glu Cys Asn Lys Ile Gly Val Gly Tyr Glu Ala Phe Asn Thr Gln Pro
            20                 25                 30

Asn Phe Cys Ser Ser Pro Tyr Trp Ser Cys Leu His Asn Gln Leu Trp
        35                 40                 45

Asn Phe Arg Glu Ser Asp Ile Asn Arg Ile Asp Arg His Gln Leu Pro
    50                 55                 60

Leu Tyr Gly Leu Glu Gly Arg Phe Glu Arg Ile
65                 70                 75

<210> SEQ ID NO 10
<211> LENGTH: 75
<212> TYPE: PRT
<213> ORGANISM: Lilium longiflorum

<400> SEQUENCE: 10

Ser Lys Trp Met Leu Leu Glu Arg Glu Arg Phe Thr Leu Asp Gly Leu
1               5                  10                 15

Glu Cys Asn Lys Ile Gly Val Ser Tyr Asp Ala Tyr Arg Ser Gln Pro
            20                 25                 30

Asn Phe Cys Ser Ser Pro Leu Trp Ser Cys Leu His Asn Gln Leu Trp
        35                 40                 45

His Phe Trp Glu Ala Asp Gln Asn Gln Ile Arg Arg Asn Gln Pro Pro
    50                 55                 60
```

Glu Tyr Val Val Glu Gly Arg Phe Lys Arg Ile
65                  70                  75

<210> SEQ ID NO 11
<211> LENGTH: 73
<212> TYPE: PRT
<213> ORGANISM: Hydra sp.

<400> SEQUENCE: 11

Ser Lys Trp Met Ile Ile Pro Arg Asp Leu Val Thr Asp Ala Lys
1               5                   10                  15

Gln Cys Asp Met Ile Gly Val Gly Tyr Ser Ala Phe Arg Gly Tyr Gly
                20                  25                  30

Cys Arg Ala Lys Lys Gly Ser Cys Leu Ala Asn Gln Pro Tyr Asn Lys
            35                  40                  45

Phe Met Asp Asp Glu Asp Arg Leu Glu Lys Gly Lys Met Pro Trp Tyr
        50                  55                  60

Phe Pro Ala Arg Tyr Gly Lys Leu Ala
65                  70

<210> SEQ ID NO 12
<211> LENGTH: 75
<212> TYPE: PRT
<213> ORGANISM: Trypanosoma brucei

<400> SEQUENCE: 12

Asn Glu Trp Ile Ile Val Asp Thr His Leu Val Ser Ile Arg Gly Thr
1               5                   10                  15

Glu Cys Asn Lys Val Gly Val Ser Tyr Glu Gly Phe Ala Thr Gln Gly
                20                  25                  30

Ser Arg Cys Asp Ala Tyr Pro Gly Ala Cys Leu Ala Asn Gln Leu Glu
            35                  40                  45

Asp Tyr Arg Asp Arg Asp Leu Glu Ala Glu Thr Lys Gly Gln Gln Gly
        50                  55                  60

Lys Tyr Met Ala Arg Phe Phe Ala Pro Phe Gly
65                  70                  75

<210> SEQ ID NO 13
<211> LENGTH: 76
<212> TYPE: PRT
<213> ORGANISM: Toxoplasma gondii

<400> SEQUENCE: 13

Lys His Ala Ile Ile Leu Asp Lys Asp Tyr Val Ser Val Thr Gly Tyr
1               5                   10                  15

Glu Cys Asp Lys Val Gly Thr Gly Leu Asp Arg Trp Gly Asp Met Arg
                20                  25                  30

Gly Glu Phe Cys Asn Leu Leu Pro Gly Thr Cys Ile Thr Gly Gln Leu
            35                  40                  45

Arg Lys Phe Lys Glu Val Asp Lys Leu Arg Ile Glu Gln Asn Leu Ala
        50                  55                  60

Pro Leu Tyr Ala Leu Lys Arg Glu Phe Gly Gly Phe
65                  70                  75

<210> SEQ ID NO 14
<211> LENGTH: 73
<212> TYPE: PRT
<213> ORGANISM: Plasmodium berghei

<400> SEQUENCE: 14

```
Arg Lys Ala Met Met Leu Pro Lys Tyr Met Phe Asp Leu Ser Gly Lys
1               5                   10                  15

Thr Cys Gly Lys Leu Gly Val Ser Leu Asn Thr Trp Arg Lys Ser Glu
            20                  25                  30

Gly Asn Phe Cys Gly Ser Glu Ala Gly Tyr Cys Ile Ser Asn Asn Leu
            35                  40                  45

Lys Lys Tyr Tyr Asp Ile His Asn Ser Ala Ser Ile Lys Ser Lys Tyr
        50                  55                  60

Lys Ile Lys Asn Ile Tyr Asn Ser Glu
65                  70

<210> SEQ ID NO 15
<211> LENGTH: 2670
<212> TYPE: DNA
<213> ORGANISM: Plasmodium falciparum

<400> SEQUENCE: 15
atgaacaaaa ggaaaaagac aaaacactta aaagttaatt ctatattgag aatctttttt      60
ttttttttcc ttatttcttt tcttttagt  aattgtaaat taaatgatta tataagaaca     120
aaatacccat tcattcaatt tgtatattct tattccaaaa aaaaggtatg tacatcttct     180
acagatgatt ccacatgtcg tactgtcgtt tatggagatt tagatgtttc taataattcg     240
gtgttaaggt taaggttttt aaggtctgag gggaaaggct atttttgttac tattcgaaga     300 gactatgtaa caatatctta ctatctgaaa tatatgaaag atattccttt aaagtataga     360
gaagtagttg atatatttaa taatcataaa tatgaaaaat atacagagaa acaaataaag     420
gattttactt ataattgtac tgctattaaa gtcgaagatg ccataatac tgtaggggat     480 tttgcacctc attatcatga atatacaaga ggagaatctt gtatatgccc ttcatatcat     540
ctttttaaaa atgacaattc aataaaaaga gcaaaattaa aatgcactta ttttaatatg     600
ttatttacag atagtgctat agtatatagc cgtcattgtg ctataatgga tttgttttat     660
ttttctgttt atgaaattga ctatcctcca atatttaata catatataga tataacaata     720
caagaatata catatgatga tgtatcaggt atgtcactga ataaacatga tttagttaca     780
aaagaaaaga aatatgaaat aaatgattcg atgtctgaaa taagagacga ttattttgat     840
ctttggttat ttttaagagg agaaagacat ggaaaaagaa ctttaattaa tttatcaaat     900
gattatgttg ttattccatc ttcacccttta gatgatgcgg atgtaataga aactgatgtt     960
atgagaaatt gtggtttgaa agaagataat ccagctttaa aaggatgtga ttataaacat    1020
gaatgtaaca ttatacatcc atgtttagta aaagcaatga tgttaccaaa atatctttttt    1080 gatttaagtg gtaaaacatg taataaatta ggtgtatcgt taaataaatg agagaaattct    1140 gatgggaatt tttgtggttc ttcagctggg tattgtttat ctgagaattt gtttaaatat    1200
tattacatac ataaaacatc tgttgggaat agaaaacctt cgaaatataa aattaaaaat    1260
atatatgggt ctgaaccaca gacaaaagtc tatacatctg caaaattacc taattattta    1320
aaagataagg tagatagtaa taataataaa tcttatgata ttaatgatat agataataaa    1380 atatttata atgaaaacgc tgctgcacat agtcatttta ttgattacaa atataatgga    1440
aatcatactg ttgaaattaa attcgaaact aatgcattag aagtacatga atcagacct     1500 gtgtcatatg aactattac acatattact ataccaaaag attgttcatc aaatcaaaca    1560
aattctaaag aatgtattct tgttgtacat acgtggaata taataaaaac tataggagct    1620
aacttctctt gtcatgtttt atgtgttgat aaaagtactc aacaagtagc aacacatatt    1680
agtcccatta gtaaaataaa tgcacatatt gatgcaaata aaaattatgc cttttatttc    1740
```

| | |
|---|---|
| attattaaat tttaataaa taaaaaaata acaagtaatt gtacagcaat actaaaagat | 1800 |
| gctgatggta gggaatgttc aaaactttca tttaatttaa catctaaaga aacaataaat | 1860 |
| gtagtagaat caggaatagt agcacaacct gtagaaagtg aagctcaaat aaataaatat | 1920 |
| gatcctgatg tatcaggagc atctacgcct acagctgata aatgtgattg ttattttaat | 1980 |
| ttattatgtt atatacttaa tttgaataca tgtgtttcat attatactaa attaattaaa | 2040 |
| gattaccttg gaagatttgt aacgatagct atattaattt ttcttgcacc atccttaata | 2100 |
| cccctgttac catttatcat taaatttttt atatcatgtg catctctccc aatgaaatta | 2160 |
| ttttccaact tttcttcttg gatggaaaat aaaaaaaaaa gtaataatag tacaaagcaa | 2220 |
| aataaaaatt attttcaaag gaaatatgaa aatttcaaaa aaaagagaac aaatatgaag | 2280 |
| aaaaataaat gtacatcatc ttccgtctct tctttaacaa atgtttcaag tatttcttca | 2340 |
| aataatacaa tgaacagtga tataaaaaag gacgtatcat ttaataggat taaatcaaat | 2400 |
| aggtacaata aggagaatca taaaaacaaa aagaggaaaa caaaaggtaa ccatagtaaa | 2460 |
| tatagtggta cctcgatgga gagtacacta acaaatacaa gtccctcaag tacacctgat | 2520 |
| aatttaagtg aatctcatat aacatctaat tcaaacaaaa ataattattc atcaaaaaaa | 2580 |
| aaaaacaagt gtaatatgct ataaaaaaa gaacattcca ggaaaagtat aagaaaaaaa | 2640 |
| tctatgggga tatctgaata ttcttcttaa | 2670 |

<210> SEQ ID NO 16
<211> LENGTH: 2439
<212> TYPE: DNA
<213> ORGANISM: Plasmodium berghei

<400> SEQUENCE: 16

| | |
|---|---|
| atgattatta ttattttttt ttgtattatt ttaaagtatt ataaatggtg tgactttaaa | 60 |
| aataaagtat ttttcattca attagtgtat tcttttgcga aaaaagtgt ctgtacttca | 120 |
| tcattggatg attcaacatg tcacacagta acttttggtg aattggatgt ttctaataat | 180 |
| tcggtagtga gattaaaggt gatgagaaaa ggaggaaaag ggtatttcct gacaattcga | 240 |
| agagattacg taactgtctc atattatttg aagtatgtaa aggacattcc tttagaattt | 300 |
| agggaaatta tagatatatt taataaccat aaatttgagc aatacacaca agagcaaata | 360 |
| aataaaatata catatacatg taatgtacgt aaaattgaag atatagataa atatgatgaa | 420 |
| aaaaatccaa ctaaatttca tgaatataca cgaggagaag catgcagatg ccaaacatat | 480 |
| aattatttta agatgatga atttataaaa agagcgaaat taaaatgtat ttattataat | 540 |
| atgctatttta ctgaatcagc gacagtatat agacattgtc ctattataga tttaatgcat | 600 |
| tttgcagttt atgatataga atatccacca atatttaata caattgttaa tattacaata | 660 |
| gaagagtatt attacaatga tgtatcatct gttttgaaca ataaatctga tttagttaca | 720 |
| aaagaaaaaa aatatcaatt aaatgatact ataacagaaa taagagatga ttattttgat | 780 |
| ttatggttat tttaaaaagg tgaaacacat ggaaaaagaa cccttgttaa tttatcaaat | 840 |
| gattatattg ttattccatc atcacctatt aataacagag atgttatagc tagtgatata | 900 |
| acaagaaatt gtggactatc acaaaattca ccattattaa aaggttgcaa ttattcaagt | 960 |
| atatgtaata ttatgcatcc atgcttacga aaagctatga tgttaccaaa atatatgttt | 1020 |
| gatttaagtg gtaaaacatg tggaaagtta ggtgtatctt taaatacttg gaggaagtca | 1080 |
| gaaggtaatt tttgtgggtc agaagctgga tattgcatat caataatct caaaaaatat | 1140 |
| tatgatattc ataattctgc atctataaaa gatggtattt ctctttcaaa gtataaaata | 1200 |

```
aaaaatatat ataattcaga accacaaact aaaatatatg aatcctataa gttgcctgat   1260
tatttaaaag ataaaattaa gaataataat catgcggaaa tggatgaaaa tgatttagat   1320
aataaaattt tttataaacc aaatgtagct gcacatagcc aattcattga ttataaatac   1380
aatggaaatc atagtgtaga aataaaattc gaaacagatg ctatagaagt atatgaaata   1440
agacccgttt ccattgcaac aattactcat gttactatac caaatgattg tgcatctaat   1500
aattctaatt caaatgaatg tgtccttatt attcatgtat ggaataatag caaatttgta   1560
ggttcaaatt tctcttgctc aattgcatgc acaaataaag aaactgacca attggctagt   1620
cacattaacc ctatcgctcc tgtgcgtgca tttattggac caaataaaaa ctatgctttt   1680
tattttataa taaaattctt aataaataaa gaattacaa cattgtgcaa agctattgta    1740
aaagattcta atgggaaaga atgctctata gaagaattcg aattacaatc aaaagaaagt   1800
gtacatatag ttgagtcaga agtagatgaa acaacggacc aagtagtagt agaacatcat   1860
acacaatcac ctgatattaa aaaccctgat gaatatgtat gtaaatgtac tattaattta   1920
ttatgttatg taattaattt caaaacatgc tctaactatt atataaatac agttaaaacg   1980
ttaattggga aatttgctat tatagccata ttaattatat tagcacctgc cttaatacct   2040
cttctaccat tcttttttaaa tttcttttttc cttttttatat ctactatact taaattatat  2100
```

-continued

| | |
|---|---|
| ctgctgtccg ccaagctgct gggcgacctg gccatgtaca cacagctgcc cgcaatcagc | 960 |
| aaccaggtgc tgatggtgcc gcagccgcca gccgccgccg ccgccaccgg ctcgcccctg | 1020 |
| gacgccaccc tggcgaccaa ccgctccgcc tggatgctgc tggacaagac catgctcagc | 1080 |
| atggacggcc tggcctgcga caaggtgggg accggcttct cagccttccg ctaccagccc | 1140 |
| agcggctgcg gccgtgcccc tcaggcctgt ctgtccggcc agctcaagga cctgtgggag | 1200 |
| gcggacctgg cgcgtatcgc ggacggccgg gtgccgctgt acatgatcac caggttcact | 1260 |
| ggcggcagcg acaccacgct gcagtccttc tccgggggcc cgctgtcgtt cgcgctgcct | 1320 |
| gtcaccagcc acagccagag cctggtgacg ctgagtgtgg cggcggacgg cgtgaggctg | 1380 |
| gtcaccaacc gcagcccggg caagattaca ggcgcggcgg tgtgccgttt cgccggcact | 1440 |
| tcctgtggcg gctttgaggc ggtggcagct cgcggctaca tctacgtcaa catcaccaac | 1500 |
| accggccgcc tggacagtga ctacacactc acagtgtcca actgctcgtc caacgtgcgg | 1560 |
| cccatcgagg cgcgcacact ggccgtacgc gcgggatccg ccgccagcct ggatccgccc | 1620 |
| atggagctgt acgtggagga ccaggcggca gcggcggcgc gcacgtgcac agtcagcctg | 1680 |
| tacgactcag tcggcgcggt gacggactcg ctcacgctgt ccttctacac aaacgccacc | 1740 |
| cagctggtcg tcaagccctc cggcgggtac aacggcacgg gggacggcgc gggcgtaaag | 1800 |
| cgcaacggca ccgattgcag cacggcctgc accaacccga ttgacgtgct gtgcttcgtg | 1860 |
| accaagaagt gctggtccaa gttcgggcgg cttctgggca tcatcggcgg cgccctggtg | 1920 |
| gggctgggc tgctggcagt agcactcaag ttcgggtggc tggcctccct ggcggcctcg | 1980 |
| tgttgtgggg gaggaggagg agcagcagca ggcggggctg gaggcggcat ggggctgggg | 2040 |
| accggcggcg gcggaggctg ttttggaggc gggcagcagc agcagcagca gccgcctgct | 2100 |
| gctagccatg ccatgtcgcc accgcagcag cagcagcagc gctcgcatgc ggaggtggca | 2160 |
| gcaggggctg cagtggcagg agcaggagcc gctgttgcag cagcggcggt gctgggagcc | 2220 |
| aaacacggcg gcggcggcgg cgctcgtggc aagcagcagc ataccgacac ccggcatttg | 2280 |
| caggatcgcg actcacgagc caccgccgac ggagcaagca ttgacagcag cagcgccggc | 2340 |
| ggcagtagca gtttaagcag ctacacccag cctcgtaagg ccgaggcag gctgctgcag | 2400 |
| ccgccggcag cagcagtgtt tgtgcctgaa ggcggc | 2436 |

<210> SEQ ID NO 18
<211> LENGTH: 1767
<212> TYPE: DNA
<213> ORGANISM: Trypanosoma cruzi

<400> SEQUENCE: 18

| | |
|---|---|
| atgagcctgt ctttgtctcg tatgcttttt tctttattgc tgtttgccct gatggttgca | 60 |
| acaactcctt ttgccgcgga gggtttactg ctggcgtcgt cttccattga acagtgcgat | 120 |
| cgtgtgggaa ccgacaactc gctgccgtgt gagaaaaagt tggtggtgac gttgtcggtg | 180 |
| gacagtgatc aggcggaaga tgtggaggag tttgtgattt tgcgcgatgc cgtggacaaa | 240 |
| acgaaaggaa cggggggagga gcacgtggaa tttcaaccta tccgtttgac gacgagcaaa | 300 |
| tcacgcgtgc aatacagtta ccctctcttt tatgaaagga atttcaatgc caagccctac | 360 |
| gaggaggaaa ttacaacgga actagttggg tgcgatgata catttagtcc gaaagcaaca | 420 |
| tgcgggctgg ccatggacac cgcgggaagg cctatcccgt acagtcaagg ttttgttgt | 480 |
| cgatgtggtc cctgtcagtt gttggggtta tgtcccgtgg gtagccgcgg tcttcaggta | 540 |
| tgcgacatat tcagaggggc tgcattagcc tcatgtctcc gttttggaga gctttggtac | 600 |

| | |
|---|---|
| agtgggtaca gcatgggttc ggctactatc tggtatcgct tgtcggtaaa actgacgact | 660 |
| gactcccaaa ataactccaa gacaaaagaa gcagttttg agctgggacc ggatgtgctt | 720 |
| tcagggtctt cagcggagtt tggggcttgg gtcagtctaa ttggggactt tgtgccggcg | 780 |
| gaattaccat tggttctaag taataaaatg cttttattc cctcttctcc aagaatacac | 840 |
| gagcgtgttt tggcgggcca aaaggagtgg ttaattctgg acaagcacca tgtgagcatg | 900 |
| cagggtcgag attgtaacaa ggttggggta tcttatgaag ccttttcggg tcaggggagc | 960 |
| aggtgccaat taattcgagg gtcgtgtctg gccgatcagt tggaggacta ccgttcgagt | 1020 |
| gatttggcag ttgaagcccg aggggtaga ggcaaatacc tggctcgctt ttttggagac | 1080 |
| tttgttgtca acaacgtcaa caacagcaga acaagactct cctactggat gcgtgggtca | 1140 |
| ttggcgacga tgttaactgt tgtcatatca gcggacagac tgcaatatct ggtttctgtt | 1200 |
| tccccaggtg aaattgtctc tgcggtgatg tcgaagtcga cagtagagga aagttcgaga | 1260 |
| gatggatccg tttctgtcat agtgcgcaat attggccacg taactgcgca atacacgctt | 1320 |
| ggtgtgggga actgttcggg aaatgttttc cccattatgg cccagaccct gagtttgaga | 1380 |
| ccacgaggga cagtgatacg cagttttgat ctgaatatcc aagatgtggc ggaagagaga | 1440 |
| attgtgcaat gcgacgtaac tttacgagac gcgaaaggtg ctatcacgga caagaagatt | 1500 |
| ttgaagtttc gagtaacaag taagtatta acgaatgata cacagggcgg caatgcacca | 1560 |
| actggaggtg gtgccagcgt ggatggtcaa gcccctccag cttgctcgcg ttgtgagtgg | 1620 |
| tacaagattt cctgtttcct gattcatggc tgttggtggc agccactggt gtatgttttg | 1680 |
| attgccattg ctatactgct gggtatatat tattttttcg gactctcttc gcgcagtagt | 1740 |
| gaacccaaat tacacgtggt tcactga | 1767 |

<210> SEQ ID NO 19
<211> LENGTH: 1857
<212> TYPE: DNA
<213> ORGANISM: Trypanosoma brucei

<400> SEQUENCE: 19

| | |
|---|---|
| atgccgacgg agacgttatc atctgttttt gtgctcgtcg tccttgtgac gacaagcggc | 60 |
| cttttcccct gcactgaggc ggcatttgtg gcctcgtcgt ccatcgagta ctgcgagcgc | 120 |
| agtagtaatg gggaaccgtt tccatgtgaa aagaagatgg ttgtgggggct ctccgtgggc | 180 |
| agcgagcaaa caattgaggc tgaagaggtt gttcttctcc gcgaggcagt tgacaaaacg | 240 |
| ggtgacgaaa agggaaagcg tgtcgagttt gaaccaatcc gcctagtgac gacaaaatca | 300 |
| ccggtgcagt accgctatcc tatttattac ataagaaact tcaatgccaa accatatgag | 360 |
| cagcgtctca gaacaagtgc aagcagttgg tgcgacgatt cttccaaccc tggatccgcg | 420 |
| acatgcggcg tggcgcgtga tcggagagga gatgtgattc cgtacagtca aggttttgc | 480 |
| tgcttatgtg gcgcttgtgc attgtcagga atttgcaacc caactagccg cagcgttgga | 540 |
| acttgcagcg tgacggggga tactggaatg catcatgcc ttcgtttcag tgacctctgg | 600 |
| tacggtggct ataccattgg tcgaggtgtt gtatggtatg aattgcaggt gaaattgtca | 660 |
| agtgggaaca acagcactgg gggaggctcc acgggctcaa aggagttcac gatgtctttg | 720 |
| gggccggata agttgaccgc cacgtcgaca gagttcggcg cgtctgcacg tcttatagga | 780 |
| gacttcgcac cccagaaaat gcctcttgac ctatcgggaa agatgttgtt tatcccctct | 840 |
| gaaccgcggg gtcatgagcg agtgggtgct gggtataacg aatggattat tgttgacacc | 900 |
| caccttgttt ctattcgtgg caccgaatgt aataaagtgg gcgtgtcata tgagggtttc | 960 |

```
gccactcagg ggagccggtg tgacgcgtat ccgggcgctt gcttggcgaa tcaactggag    1020
gattatcgtg atcgggactt ggaagcggag actaaggggc aacaagggaa atatatggct    1080 cgcttttcg ctccttttgg ttttgaccca ctggccaatg ccagtgcccc agctgtggct     1140
taccaggtga caggaacatt atcaacgatg gtgacgataa caatatccgc tgataagtta    1200
aactttgtgt tgtctgtgtc ctcggtgtg attgttggtg caaccgtttc agggaaggtg     1260
gtgcattcct attcgcgggg aagcaccatt accgtgacgg ttcttaacac tggggacatc    1320
gaggcacagt acacggttgt tgtcggcgag tgtacggtta atgttcagcc gatggttgcc    1380
caaactgtgt acatacccct acaaggatca gcgcagcgac gtttcactct gatcgtacag    1440
gacagtattg agggagaggc caaatgcaat gcaacgctga aaacgccag gggcgacgtt     1500 gtggacaccc gcgctatttc gttcggtgtt aaagcgctca accaagcaa tggctctcaa     1560 ggtggcagca cctttgaaaa tggacggtac agtgaggagg caaggggga gtcgcagtgc     1620 caacagtgca gttggttcaa tcttttgtgt tttctgaggc atcgatgctg gtggcaaccg    1680
ctggtgtacg tccttccttc agtgaccctg ttaatgctgc tgcgcaggtt ccttgagagt    1740
cagtcaaggt cccgcccaag accccaatta caccctgatg agcatgaact gagaaatacc    1800
ggtgccatct cttcgtgcca tcttccccgc gcaccgtacg ttaacacagt gcactga      1857
```

<210> SEQ ID NO 20
<211> LENGTH: 1185
<212> TYPE: DNA
<213> ORGANISM: Cryptosporidium hominis

<400> SEQUENCE: 20

```
atgtggtgga atgtttactt atcgaagtca tgcccagttt ggataccacc atggtggaca     60
gcttttagaa taggtggatg gaattggcaa tactcattag aggttgaatt atcttggttt    120
agtccaacag aatcatcaat taataagtta tcaagtacag aattggaaaa tatggaaaat    180
gaatgtaaga agaaaataa agattccaca atagattgtt caagaataag gcataaagaa    240
tcaggaattc agacttctgt acatacatta aattcatcgt ctccatcatt ctatgatcca    300
aattttggag cttcagtaca ggtaataagt tcaggaccgc cgtttgggag tgctaatgca    360
aaggatttga tggttatta catgttacaa ccaacatttt caccaaaagg gatgcctgct    420
agtattgcaa ttcctccttt aagaagtggg tgtggaaaag cttcaaaaaa ccaaacagaa    480
gaggaaatga atgattgttt aaagccaaca ttaattattc ctccagaaaa tgcagacttt    540
acaggagttt catgtgataa gataggaaca agtgttcata cttggagttc tgtgaatggt    600 agatttgct atcatccacc tgggacttgt caaagagctc agatagctca ctttatalag    660 aaagttatag aagatcattc acttggaaag atttcacaat attcagtgag agcacaaaat    720
tctggttctc cacagttgat tttggattca ttgggagaaa ttggtcatga agaggtggat    780
caaaatgata tggaaaatat aactaatata caatcacgta gattctttt gggatataat    840 tttgattcaa tctttgacac agaaataatg ttctcagtcg aagcttcttc tgtgtcttgg    900
gtagcaacat cttctcctgg aattattaca tatatagaac caccaccttt ggaggcttgc    960
acagcaatga gtagttttgg ctgtcctcta aaggtttata ttaagaatag tggtaagttt   1020
gaatatatat atacatttcg aattgaatta aaaataactt atcaaaaata ttctataggg   1080
gatattgatt caggttttgt agttcaaata ccttattgta caaagtcagg agtacaaaca   1140
agtgaggtag gtttatattt aactcattca aatttatata attaa                   1185
```

```
<210> SEQ ID NO 21
<211> LENGTH: 2919
<212> TYPE: DNA
<213> ORGANISM: Toxoplasma gondii

<400> SEQUENCE: 21
atggatccac cactgccgcg atggagagcc gtggctgtgg cagcttttct catcgccacc      60
atctgtcaca atggcgtgga cgccgacatt cctcaggccg tgtcacggca acagatctgc     120
acagtcaatg gcgcatatgg aaaggatgat cctagacgaa tgcagtgcaa agatacgatt     180
ctagggactc tgagaatatc taataaagag aaattttcgt ttaatgtcat gcaaaacacc     240
atcgattccc gggacaagac atacgctgac gtgggaaatg tcggattcgt cgtgaccatt     300
acgaagactc ccgtaacaat atcgctgcct ctagagtaca tcaaggaggt accgttcgat     360
tatcgggaag agatatacga atattcccgg tgggaggctg ggcgactgcc ggagaagttt     420
tgttacgaag acacgacaga caaatgctct gaagatggga agctggcggt ccaccctcac     480
ggcaagcccc tgtcatgggc ccacggccgc tgctgctggt gtagtgaagt gctggctttc     540
acgcatatca caacatgaa gaggggcaac ttccgttgca attggtttgc cccgccccgc     600
gccttggaac tggtgactga aaccctctac gaccagtgtg aagccgggaa aatagacggc     660
accgttccat tggaccgaga ttgcgaaaga gagaagcacg agcgcttggg catcaccgac     720
agagtttaca cactgaacta cactacacca gaaatcttcg accgttctgt ctattgcaat     780
acaaagtctt gcttgaaaca cgccatcatc ttggacaagg actatgtttc tgtcacgggt     840
tatgaatgcg acaaagttgg caccggcctc gatcgatggg gagacatgag aggagagttt     900
tgcaatctgt taccagggac ttgtatcact ggccagcttc ggaaattcaa ggaagtcgac     960
aagctacgga tcgaacaaaa tctggccacc ttatatgcac tgaaacggga gttcgggggc    1020
ttccctcgat atgcgccaaa cccgatgaat ggaacgggtt tttcaacaac aggcacaaga    1080
cactacctcg gctacgattt tggcgagcag cactactcag acatccgttt cgagatggat    1140
gcaaccgatg tcacatggtt gagggcaaca tcacccggtc acataacctt cattgaggtg    1200
cctcagctag acgcatgctc gtccagtacc attggcgggt gtccactgaa agcctacgtc    1260
tggaattcag gcaacgaaga tgctgcattt gcagtagagg tacccttttg tatcgattcg    1320
attacaaagg agcgaacaat cgatgtaaat cccattacgc cagttcggac gacagtgcct    1380
gctgacaaaa cggttgtttt cacgttaacc tttaaagcca tttcttctag tagtcttggc    1440
gttacatgtt tcatgaagct gtacgatgcc cagcatctca tgctcgacca aaagacattc    1500
aatgtgacga cgtcggctgc tcaggcacac gacacacagc actcacacaa ataacgaag    1560 atgcctcaga gaaaactact cggggggggct tttacgaaag cagccgtcgg tgccacagca    1620
gcaatgggtt tctttggtcg gagaacgggg aagaagaaga aggagacac aaatgttgag    1680 gcgcattctg taacgccaca atcgtttgcc gaagacgcaa gaggtcctgg gatccaagat    1740
aaacttcagg gaaaggctga cccggcagaa acgtctctgt tcggggaatc ggccacgagt    1800
cacgcagcga agttgagcaa gaaggaaaaa cgcagtttac gcaaacaagc aaagaaacaa    1860
aaaaggcaag aatatcagcg gcaggcagcg gcagggaacg cagaaatttg gcaggagaa    1920 ggagaagcca ctgcgtctaa aaaagacatg gtttccaaga gaatggggt cgaggggtcg    1980 cggtcctcga ctatgggtat cgccgacaac aaccaatctg cttcagcagt cacgaagtca    2040
aaaccgcata tcatgaagga caacgggag acaggggcca aacgaaggca aggggagtgt    2100
gcaagaacaa aggaggaaga taacgcgggg cactagaag gaaactgaa ggagaaacac    2160 tctacccaga gccaaccgga tcatcctctc tctgcaggaa acaagggcac gagcacaact    2220
```

| | |
|---|---|
| caacagatca ggagtcagat tgaacataaa tcctccatttt tcatgggaaa cgacaatcag | 2280 |
| acacctctcg aagtagagct agaaggacaa ctgcggaaac atctaggtca agatgactct | 2340 |
| gattcgcacc cgtcaaaggc cggaaaagac aaggtgcttg agcacgggca acacccgtc | 2400 |
| gagagggaaa aagaaggcaa cgaagaggat agcgcagata gagggaaaga acgatcaaac | 2460 |
| gttgggatca ctggtgcagc agggaagatg aggaagttcc tgcacagaaa aagggatgaa | 2520 |
| atcgaatacc aagaaggccg tgaagaggcg ggattagacg cagtgtccat cagtagagga | 2580 |
| agtacacaat gcacccgtgc acggaaggcg aagagaaaga agcagcattt gaaggaaccg | 2640 |
| cgaacaccgc aagaagaaaa cccagaagat gacatcgaag aacaggacag agatgaagaa | 2700 |
| ggcgaatccg atacactaag ggatacgact gaccaaggag gcgcatcacc gcagacagca | 2760 |
| cgaccagagc tcaccacagt agtggcacat gaacccgaaa cacgggggga aaaatacatt | 2820 |
| gaagggagtt tctcgactct accctctgtg gaaatcgagg aacacaaaga gattcagatg | 2880 |
| gtcgaaacaa atcctagtta ctgtgtttca atgaggtag | 2919 |

<210> SEQ ID NO 22
<211> LENGTH: 2280
<212> TYPE: DNA
<213> ORGANISM: Theileria parva

<400> SEQUENCE: 22

| | |
|---|---|
| atgagctctt taggccctttt tagaagtgtg ttcacttccc ttatatactt ctcaatccta | 60 |
| cacattctcg gctttacatc actattcaat ttttacacca ctgatagcac tggtttcttc | 120 |
| tttgttgact cagcagtgac cggaaacata acccaatgtg ttagaaatag cgataaactc | 180 |
| ttcgatgatc aaacttgtgt acaaagattg cacaccaacg tcgatgtctc acatggactc | 240 |
| agggagtacc attacatata tagaagaaaa gatgatttat ctaagggatt atacttggtg | 300 |
| ttaaagacct caaacacttc tctactctac actctcaatt atcaaactat ggtcccgttg | 360 |
| tattatacgg atcatacgga gaggtggacg tatagtgaga tttcaggtga gttgaagacc | 420 |
| tcgtgtaaga gtgtgcaaaa ttctaaatgc actaaaaaaa ctcaagttcc accaggtatt | 480 |
| gatttcttac ccagagtctg ctgtatctgc ggactgaacg tacataaacc aacgccaaga | 540 |
| gctgatttta aatgcggagg atttctggct atgggaggta ggacagcgtt gagtatgagt | 600 |
| tgtttggaga taagtgagcc ctggtataag ctttacaaga ccagttaccc accagccata | 660 |
| agcagaagtg ttactgttaa catttacaaa ttcgattcat ccactggaat tatcccagac | 720 |
| gtgacattgg aggatgagga taaatttgat aattatgact ttaagaagcg ggagaagaag | 780 |
| gacccggtga tcaagtcacc ggagatcaaa tcacgctcca ctaaagaaat aacgggaaaa | 840 |
| aaagatgaat tacaccccaa tttcagacgc atcatcatcg atgataccgt caaagaagaa | 900 |
| catatcaatg atttggatgt gaagataacg ctgttgtcga gtaatacgaa ggatggctct | 960 |
| gcgcccccgt tatttgataa atacgtagcc ataccatcat tcccaagaac caatgaaacc | 1020 |
| gtcaaaggct catcactcat ggacaaatgt caagacagca cctggaaaac caaacccgaa | 1080 |
| tgtcccaaat atatgaatcc atcgttgtgt gatatatggc gttgtacgtt gaatatgagg | 1140 |
| actgtgaaga tgagtgcggt ggatacggat gggttgatgt gtgataaaat cggcttatca | 1200 |
| atgaagaggt gggcaaacca agaggaaatt tgtaactcaa gccccggctc atgcctcaaa | 1260 |
| aatcagctga acactactt cgatcaggaa aaagatgagg ccaaattacc aaaattgtac | 1320 |
| ggagtagagc caacgtttac agcggttaaa aaagatctgt cattaccagc agtaaaggaa | 1380 |
| gcaaataaaa caactctgga tgatccaaac agaattcaca ctctcactta tatccactct | 1440 |

```
aaggacgatg ttaccagact taaaatcgat accttcgacg ccacagtcac cgaaatcatc    1500
tccgatttcc ccgggttcat cgtctccgca aagatggacg gagagtgtga ggtatcttcg    1560
gagaaaggct gtaacatgga attggacgtt aaaaacatgg gtaaatttac acacaaaaat    1620
agtattttag gggttaagaa gtcggaattt accgttagag cgaattgtta tgatgatcct    1680
gaccttaaaa atgaagttgc tcagatttct gaaactacac tcagtatcga cgggaataaa    1740
aataaaaccg tctctatacc aatcaaactc acaggatcac tcgctagtga aaaggatac     1800 tgcaacatca ttctccttc cggaaagaag gagatgttgg atggtatgaa gatggagata    1860
aaggtgaagg tgaagaagga gacgtttggt aaggatccgg ttaaggtcca ggatatagtg    1920
gctgctccta gtcctaagga taaattaacc actcctcaag tgattaaccc gattgtcatt    1980
aaccaacccg ggtctaaaaa tgacactaaa aagaggaag agtcacaatg caaatgcgcg    2040
tcctggaata tcttctgcat gctcatcaac tttaagatat gtgtttcgtc ttatgtgagt    2100
aaggtattat tttacgtgtt gattgcactt ggaattttat tgcttttgat tttgttgccg    2160
gtgttgattc cgttaattgt tagtctcttt aaggctctcg ctggactcat caaaacacca    2220
ctcgaagccc tcgaacaaag aagattaaag aaaaaaaca atacacaact tgaagtttaa    2280

<210> SEQ ID NO 23
<211> LENGTH: 498
<212> TYPE: DNA
<213> ORGANISM: Eimeria tenella

<400> SEQUENCE: 23
gcagctgctg ctgctgcggc tgcagcctcc cgcagtgtct cgacacatca gtagcaacgt     60
gctgccgcaa atgaattttt atttgtggct tctaggggta ggcttgtata ccccttcact    120
gcagcagcag atgatgatac cgtctcggaa cagggttttc attttgacgc tacatggttt    180
gcgcggtctc gagcaaagaa tgtcaattcc gattgtggca cttcaagcta cggtaatgct    240
ttacgtgacg aagtgctttt ccagttcttt ctcccgatga gctttttaat ttcaggctca    300
ccattttgta accctaagag ctgtctgagg catatgatcg tcctagacga acaacacgtc    360
acagtggatg gcagcacgtg tgatctcccg ggagtttcac tgcagcaatg gggaagagac    420
ggcttttgtg attacgcaca aggaacgtgc tttgcgaaaa acttgaagtg gtttcatgaa    480
tacaacgaac aggccgca                                                  498

<210> SEQ ID NO 24
<211> LENGTH: 1731
<212> TYPE: DNA
<213> ORGANISM: Leishmania major

<400> SEQUENCE: 24 atgggggca ccgccacggc aacggcctac gtgcggtcct gcgacggagc ctcgccaccc     60
acgccgcctg ggtgcgggct caagctggtg gtggacctca ccctcgacga cagcattctc    120
accggctccg tcttggagac agaggtgatg gtgacgcacg cgttgcatga gtcactcttt    180
ccccgtgacg cggcgtccga tgccgctggc acagctgcca cctctctgca ggtgtctctg    240
cctcccatca cggtggcaat gcggcgtggc gctgtgcaga tgcgctacgg gctcacctac    300
ctacgcacgt tccggcggc attgcgagac tctgtgcggg tactgaagac ggccatgtcg    360
tgcgacgacg gcgtcacgcg ctgtccttcc tacatgagca tgacagggac gcttgtgtcg    420
gcgccgctcg gattgtgctg cctctgcacc agcgtggagt gcgccctcac aagcgacctg    480
tgcaacgctt cgatgcgcgc gcactttgc ttccgcaccg gtgcagccgg aatcacgtgc    540
```

```
gtacagagcg agggcatcac ctaccacgga tgggccgtgg gatcgtcgtc gccctactac     600
atgatgcacc tatccgcgag cgggcgaggg atcgcaccga cgacactgca gctcacgacg     660 gacgccctg  aggtgcagaa gggtgcgtct gctctgcaga ttcttcgggc ctctggtgtt     720
ttgcccggag agtcaaaccc cacggttgat atttccgggc gcgttctctt tgtcccctct     780
gcagaacaca gcagtgccag ccgcagcatc agcaccgggc ctgtgcgcga cgacgacccg     840
gcagagtggc tgttgctccc ggcgccgctt gtcagcgtct ccggcaatga ttgcgacaag     900
gtcggcatct caccagacta tttctactcg ctctccagca ctaagcagtg caacgcgcag     960
aaggggacgt gcgtgcgaca ccagctagca gactaccgtg cggcggacct ggaacagatc    1020
gcccagggcg tcggcggacg ctatatcgcc gcctctctgg gcaccttcac gcggcaggcg    1080
atgagggaac aggagttcct gctcgatgcg gtggagcgca cgggtggggc gatgctgcgg    1140
tggacggtga atgcggacgg cctcgtgttc cagccgcttc cggtacacgg tgtactggat    1200
gctatcaagt ttgacagcag cacaggcatc ctctacgtca cggttcgcaa caacaacaca    1260
tatggtggcc tctactacgt tgccgttggt cagtgtcggg gagcacgcgc atcgaactgc    1320
gatagcgacg gcgtgacaca cgagtgtggt cgcacggctt tggtggccgg ggctaacacc    1380
tcctcgctgt tgcagttcag catggtgagc gacctgcccg aggaggtggg gagcaccgcc    1440
tcatgcaccg tcgtctttcg cgacgcggcc gcagcgctgc tggcctctgc aaacattcc     1500 tggacggtcg agcacacgac cactacgccg gcgccgaatg ccccccaaagc ggagcagtgc    1560 agacgctgcg cctttcgcga cctgcggtgt cttttcagca ccgtctgcga gtggcagatg    1620
ctcctgtgga cagcggtggc ggtggcggtg acgtggacgc cgtatgccat cttggcctac    1680
tggcgtatgg cgtggcacgt tggcgccaag ctcttggcgt gtctgaactg a             1731
```

<210> SEQ ID NO 25
<211> LENGTH: 692
<212> TYPE: PRT
<213> ORGANISM: Chlamydomonas reinhardtii

<400> SEQUENCE: 25

```
Met Arg Gly Ser His His His His His His Gly Ser Ala Cys Glu Leu
1               5                   10                  15

His Ala Glu Val Ile Ala Ser Gly Arg Leu Glu Lys Cys Val Val Asp
                20                  25                  30

Gly Val Thr Glu Glu Leu Asp Cys Gln Glu Lys Val Val Val Thr Leu
            35                  40                  45

Thr Val Gly Asn Gly Gln Ser Leu Gln Thr Glu Ala Leu Glu Phe Ser
        50                  55                  60

Leu Ser Cys Leu Asn Ser Pro Asp Gly Arg Cys Pro Cys Ser Cys Ser
65                  70                  75                  80

Ala Ala Asp Pro Thr Cys Ala Cys Arg Asp Leu Ala Ala Pro Leu Arg
                85                  90                  95

Val Ser Leu Thr Lys Ser Pro Leu Trp Ala Ser Tyr Pro Leu Gln Tyr
            100                 105                 110

Leu Ser Ser Phe Asn Trp Lys Pro Leu Glu Val Ile Leu Arg Pro Ser
        115                 120                 125

Asn Lys Val Cys Lys Asp Gly Asp Trp Glu Asp Ser Pro Thr Cys Gly
    130                 135                 140

Trp Phe Ser Gln Gly Gly Val Arg Val Ala Asp Ser Gln Gly Phe Cys
145                 150                 155                 160

Cys Glu Cys Ser Ser Ser Gln Val Trp Asp Asp Thr Phe Gly Ser Ser
```

```
                165                 170                 175
Lys Glu Arg Thr Arg Ala Asn Leu Asp Cys Asp Phe Trp Ser Asp Pro
            180                 185                 190

Leu Asp Ile Leu Ile Gly Arg Lys Pro Val Ser Ala His Cys Leu Thr
        195                 200                 205

Phe Asp Pro Gln Trp Tyr Ser Gly Tyr Glu Leu Gly Ala Ala Ser Leu
    210                 215                 220

Gln Phe Glu Ile Ala Ile Thr Val Glu Val Pro Thr Ala Pro Ser Pro
225                 230                 235                 240

Thr Thr Ala Thr Thr Ser Ala Thr Pro Arg Thr Asn Asn Ser Ser Ser
                245                 250                 255

Ala Asn Ser Thr Asn Ser Thr Asn Ser Pro Ala Pro Gln Phe Leu Ser
            260                 265                 270

Pro Pro Ala Pro Ser Thr Arg Glu Val Leu His Leu Gly Pro Ser Val
        275                 280                 285

Pro Leu Ala Ser Ser Ala Ser Arg Leu Leu Ser Ala Lys Leu Leu Gly
    290                 295                 300

Asp Leu Ala Met Tyr Thr Gln Leu Pro Ala Ile Ser Asn Gln Val Leu
305                 310                 315                 320

Met Val Pro Gln Pro Pro Ala Ala Ala Ala Thr Gly Ser Pro Leu
                325                 330                 335

Asp Ala Thr Leu Ala Thr Asn Arg Ser Ala Trp Met Leu Leu Asp Lys
            340                 345                 350

Thr Met Leu Ser Met Asp Gly Leu Ala Cys Asp Lys Val Gly Thr Gly
        355                 360                 365

Phe Ser Ala Phe Arg Tyr Gln Pro Ser Gly Cys Gly Arg Ala Pro Gln
    370                 375                 380

Ala Cys Leu Ser Gly Gln Leu Lys Asp Leu Trp Glu Ala Asp Leu Ala
385                 390                 395                 400

Arg Ile Ala Asp Gly Arg Val Pro Leu Tyr Met Ile Thr Arg Phe Thr
                405                 410                 415

Gly Gly Ser Asp Thr Thr Leu Gln Ser Phe Ser Gly Gly Pro Leu Ser
            420                 425                 430

Phe Ala Leu Pro Val Thr Ser His Ser Gln Ser Leu Val Thr Leu Ser
        435                 440                 445

Val Ala Ala Asp Gly Val Arg Leu Val Thr Asn Arg Ser Pro Gly Lys
    450                 455                 460

Ile Thr Gly Ala Ala Val Cys Arg Phe Ala Gly Thr Ser Cys Gly Gly
465                 470                 475                 480

Phe Glu Ala Val Ala Ala Arg Gly Tyr Ile Tyr Val Asn Ile Thr Asn
                485                 490                 495

Thr Gly Arg Leu Asp Ser Asp Tyr Thr Leu Thr Val Ser Asn Cys Ser
            500                 505                 510

Ser Asn Val Arg Pro Ile Glu Ala Arg Thr Leu Ala Val Arg Ala Gly
        515                 520                 525

Ser Ala Ala Ser Leu Asp Pro Pro Met Glu Leu Tyr Val Glu Asp Gln
    530                 535                 540

Ala Ala Ala Ala Ala Arg Thr Cys Thr Val Ser Leu Tyr Asp Ser Val
545                 550                 555                 560

Gly Ala Val Thr Asp Ser Leu Thr Leu Ser Phe Tyr Thr Asn Ala Thr
                565                 570                 575

Gln Leu Val Val Lys Pro Ser Gly Gly Tyr Asn Gly Thr Gly Asp Gly
            580                 585                 590
```

```
Ala Gly Val Lys Arg Asn Gly Thr Asp Cys Ser Thr Ala Cys Thr Asn
            595                 600                 605

Pro Ile Asp Val Leu Cys Phe Val Thr Lys Lys Cys Trp Ser Lys Phe
    610                 615                 620

Gly Arg Leu Leu Gly Ile Ile Gly Gly Ala Leu Val Gly Leu Gly Leu
625                 630                 635                 640

Leu Ala Val Ala Leu Lys Phe Gly Trp Leu Ala Ser Leu Ala Ala Ser
                645                 650                 655

Cys Cys Gly Gly Gly Gly Ala Ala Gly Ala Gly Gly
                660                 665                 670

Met Gly Leu Gly Thr Gly Gly Gly Gly Cys Phe Gly Gly Gln
                675                 680                 685

Gln Gln Gln Gln
    690

<210> SEQ ID NO 26
<211> LENGTH: 5841
<212> TYPE: DNA
<213> ORGANISM: Chlamydomonas reinhardtii

<400> SEQUENCE: 26
ctcgagaaat cataaaaaat ttatttgctt tgtgagcgga taacaattat aatagattca      60
attgtgagcg ataacaatt tcacacagaa ttcattaaag aggagaaatt aactatgaga     120
ggatcgcatc accatcacca tcacggatcc gcatgcgagc tccacgctga ggtcattgca     180
agtgggcgct tggaaaaatg cgtcgtcgat ggtgttaccg aggagctgga ctgccaggag     240
aaggtggtgg tgacactgac ggtcggaaat gggcagagcc tgcagaccga ggctctggaa     300
ttctcgctca gctgcctcaa cagccccgac ggacgctgcc cctgcagctg cagcgccgcc     360
gaccctactt gcgcatgtcg tgacctggcg gcgccgctgc gcgtgtcgct taccaagtcg     420
ccgctgtggg cctcctaccc gctgcagtac ttgtcgtcct ttaactggaa ccccctggaa     480
gtcatcctgc gccccagcaa caaagtttgc aaggacggcg actgggagga ctcgcccacg     540
tgtggctggt tcagccaggg cggtgtgcgc gtggcggaca gccagggatt ctgctgcgag     600
tgcagcagca gccaggtgtg ggacgacacc ttcgggtcca gcaaggagcg cactcgcgcc     660
aacctggact gtgacttctg gagcgaccca ctggacatac tgattggccg caagccggtg     720
tccgcacact gcctcacatt cgacccgcag tggtacagcg gctatgagct gggcgccgcc     780
tcgctgcagt cgagatcgc catcaccgtg gaggtaccca cgccccctc ccccaccaca     840 gccaccacct ccgccactcc ccgcaccaac aacagcagta gcgccaacag caccaacagc     900
accaacagcc ggcgccgca gtttctgtcc ccgcctgcgc ccagcacgcg ggaagtgttg     960
catctgggtc cctcggtgcc tctggccagc agcgcgagcc gcctgctgtc cgccaagctg    1020
ctgggcgacc tggccatgta cacacagctg cccgcaatca gcaaccaggt gctgatggtg    1080
ccgcagccgc cagccgccgc cgccgccacc ggctcgcccc tggacgccac cctggcgacc    1140
aaccgctccg cctggatgct gctggacaag accatgctca gcatggacgg cctggcctgc    1200
gacaaggtgg ggaccggctt ctcagccttc cgctaccagc ccagcggctg cggccgtgcc    1260
cctcaggcct gtctgtccgg ccagctcaag gacctgtggg aggcggacct ggcgcgtatc    1320
gcggacggcc gggtgccgct gtacatgatc accaggttca ctggcggcag cgacaccacg    1380
ctgcagtcct tctccggggg cccgctgtcg ttcgcgctgc ctgtcaccag ccacagccag    1440
agcctggtga cgctgagtgt ggcggcggac ggcgtgaggc tggtcaccaa ccgcagcccg    1500
ggcaagatta caggcgcggc ggtgtgccgt ttcgccggca cttcctgtgg cggctttgag    1560
```

```
gcggtggcag ctcgcggcta catctacgtc aacatcacca acaccggccg cctggacagt   1620
gactacacac tcacagtgtc caactgctcg tccaacgtgc ggcccatcga ggcgcgcaca   1680
ctggccgtac gcgcgggatc cgccgccagc ctggatccgc ccatggagct gtacgtggag   1740
gaccaggcgg cagcggcggc gcgcacgtgc acagtcagcc tgtacgactc agtcggcgcg   1800
gtgacggact cgctcacgct gtccttctac acaaacgcca cccagctggt cgtcaagccc   1860
tccggcgggt acaacggcac gggggacggc gcgggcgtaa agcgcaacgg caccgattgc   1920
agcacggcct gcaccaaccc gattgacgtg ctgtgcttcg tgaccaagaa gtgctggtcc   1980
aagttcgggc ggcttctggg catcatcggc ggcgccctgg tggggctggg gctgctggca   2040
gtagcactca agttcgggtg gctggcctcc ctggcggcct cgtgttgtgg gggaggagga   2100
ggagcagcag caggcggggc tggaggcggc atggggctgg gaccggcgg cggcggaggc   2160 tgttttggag gcgggcagca gcagcagcag cctgctgcta gccatgccat gtcgccaccg   2220
cagcagcagc agcagcgctc gcatgcggag gtggcagcag gggctgcagt ggcaggagca   2280
ggagccgctg ttgcagcagc ggcggtgctg ggagccaaac acggcggcgg cggcggcgct   2340
cgtggcaagc agcagcatac cgacacccgg catttgcagg atcgcgactc acgagccacc   2400
gccgacggag caagcattga cagcagcagc gccggcggca gtagcagttt aagcagctac   2460
acccagcctc gtaaggccgg aggcaggctg ctgcagccgc cggcagcagc agtgtttgtg   2520
cctgaaggcg gcatcactag tgaattcgcg gccgcctgca ggtcgaagct taattagctg   2580
agcttggact cctgttgata gatccagtaa tgacctcaga actccatctg gatttgttca   2640
gaacgctcgg ttgccgccgg gcgttttta ttggtgagaa tccaagctag cttggcgaga   2700
ttttcaggag ctaaggaagc taaaatggag aaaaaaatca ctggatatac caccgttgat   2760
atatcccaat ggcatcgtaa agaacatttt gaggcatttc agtcagttgc tcaatgtacc   2820
tataaccaga ccgttcagct ggatattacg gcctttttaa agaccgtaaa gaaaaataag   2880
cacaagtttt atccggcctt tattcacatt cttgcccgcc tgatgaatgc tcatccggaa   2940
tttcgtatgg caatgaaaga cggtgagctg gtgatatggg atagtgttca cccttgttac   3000
accgttttcc atgagcaaac tgaaacgttt tcatcgctct ggagtgaata ccacgacgat   3060
ttccggcagt ttctacacat atattcgcaa gatgtggcgt gttacggtga aaacctggcc   3120
tatttcccta aagggtttat tgagaatatg ttttttcgtct cagccaatcc ctgggtgagt   3180
ttcaccagtt ttgatttaaa cgtggccaat atggacaact tcttcgcccc cgttttcacc   3240
atgggcaaat attatacgca aggcgacaag gtgctgatgc cgctggcgat tcaggttcat   3300
catgccgtct gtgatggctt ccatgtcggc agaatgctta atgaattaca acagtactgc   3360
gatgagtggc agggcggggc gtaatttttt taaggcagtt attggtgccc ttaaacgcct   3420
ggggtaatga ctctctagct tgaggcatca aataaaacga aaggctcagt cgaaagactg   3480
ggcctttcgt tttatctgtt gtttgtcggt gaacgctctc ctgagtagga caaatccgcc   3540
gctctagagc tgcctcgcgc gtttcggtga tgacggtgaa aacctctgac acatgcagct   3600
cccggagacg gtcacagctt gtctgtaagc ggatgccggg agcagacaag cccgtcaggg   3660
cgcgtcagcg ggtgttggcg ggtgtcgggg cgcagccatg acccagtcac gtagcgatag   3720
cggagtgtat actggcttaa ctatgcggca tcagagcaga ttgtactgag agtgcaccat   3780
atgcggtgtg aaataccgca cagatgcgta aggagaaaat accgcatcag gcgctcttcc   3840
gcttcctcgc tcactgactc gctgcgctcg gtctgtcggc tgcggcgagc ggtatcagct   3900
cactcaaagg cggtaatacg gttatccaca gaatcagggg ataacgcagg aaagaacatg   3960
```

```
tgagcaaaag gccagcaaaa ggccaggaac cgtaaaaagg ccgcgttgct ggcgttttc    4020 cataggctcc gccccctga cgagcatcac aaaaatcgac gctcaagtca gaggtggcga    4080
aacccgacag gactataaag ataccaggcg tttcccctg gaagctccct cgtgcgctct    4140
cctgttccga ccctgccgct taccggatac ctgtccgcct ttctcccttc gggaagcgtg    4200
gcgctttctc aatgctcacg ctgtaggtat ctcagttcgg tgtaggtcgt tcgctccaag    4260
ctgggctgtg tgcacgaacc ccccgttcag cccgaccgct gcgccttatc cggtaactat    4320
cgtcttgagt ccaacccggt aagacacgac ttatcgccac tggcagcagc cactggtaac    4380
aggattagca gagcgaggta tgtaggcggt gctacagagt tcttgaagtg gtggcctaac    4440
tacggctaca ctagaaggac agtatttggt atctgcgctc tgctgaagcc agttaccttc    4500
ggaaaaagag ttggtagctc ttgatccggc aaacaaacca ccgctggtag cggtggtttt    4560
tttgtttgca agcagcagat tacgcgcaga aaaaaggat ctcaagaaga tcctttgatc    4620
ttttctacgg ggtctgacgc tcagtggaac gaaaactcac gttaagggat tttggtcatg    4680
agattatcaa aaaggatctt cacctagatc cttttaaatt aaaaatgaag ttttaaatca    4740
atctaaagta tatatgagta acttggtct gacagttacc aatgcttaat cagtgaggca    4800
cctatctcag cgatctgtct atttcgttca tccatagctg cctgactccc cgtcgtgtag    4860
ataactacga tacgggaggg cttaccatct ggccccagtg ctgcaatgat accgcgagac    4920
ccacgctcac cggctccaga tttatcagca ataaaccagc cagccggaag ggccgagcgc    4980
agaagtggtc ctgcaacttt atccgcctcc atccagtcta ttaattgttg ccgggaagct    5040
agagtaagta gttcgccagt taatagtttg cgcaacgttg ttgccattgc tacaggcatc    5100
gtggtgtcac gctcgtcgtt tggtatggct tcattcagct ccggttccca acgatcaagg    5160
cgagttacat gatcccccat gttgtgcaaa aaagcggtta gctccttcgg tcctccgatc    5220
gttgtcagaa gtaagttggc cgcagtgtta tcactcatgg ttatggcagc actgcataat    5280
tctcttactg tcatgccatc cgtaagatgc ttttctgtga ctggtgagta ctcaaccaag    5340
tcattctgag aatagtgtat gcggcgaccg agttgctctt gcccggcgtc aatacgggat    5400
aataccgcgc cacatagcag aactttaaaa gtgctcatca ttggaaaacg ttcttcgggg    5460
cgaaaactct caaggatctt accgctgttg agatccagtt cgatgtaacc cactcgtgca    5520
cccaactgat cttcagcatc ttttactttc accagcgttt ctgggtgagc aaaaacagga    5580
aggcaaaatg ccgcaaaaaa gggaataagg gcgacacgga aatgttgaat actcatactc    5640 ttccttttc aatattattg aagcatttat cagggttatt gtctcatgag cggatacata    5700
tttgaatgta tttagaaaaa taaacaaata ggggttccgc gcacatttcc ccgaaaagtg    5760
ccacctgacg tctaagaaac cattattatc atgacattaa cctataaaaa taggcgtatc    5820
acgaggccct ttcgtcttca c                                              5841
```

<210> SEQ ID NO 27
<211> LENGTH: 31
<212> TYPE: DNA
<213> ORGANISM: Plasmodium berghei

<400> SEQUENCE: 27
ccccgggccc gcgcgttatt attattcggg c                                   31

<210> SEQ ID NO 28
<211> LENGTH: 39
<212> TYPE: DNA
<213> ORGANISM: Plasmodium berghei

```
<400> SEQUENCE: 28
ggggaagctt tttttctaaa tgaaatatta aagaatggc                              39

<210> SEQ ID NO 29
<211> LENGTH: 38
<212> TYPE: DNA
<213> ORGANISM: Plasmodium berghei

<400> SEQUENCE: 29
ccccgaattc attacatgga atagtatttg caaatttg                               38

<210> SEQ ID NO 30
<211> LENGTH: 33
<212> TYPE: DNA
<213> ORGANISM: Plasmodium berghei

<400> SEQUENCE: 30
ggggtctaga caatatacat gctgataacc tcc                                    33

<210> SEQ ID NO 31
<211> LENGTH: 26
<212> TYPE: DNA
<213> ORGANISM: Plasmodium berghei

<400> SEQUENCE: 31
ctcgaatatg tagatatatc cagatg                                            26

<210> SEQ ID NO 32
<211> LENGTH: 27
<212> TYPE: DNA
<213> ORGANISM: Plasmodium berghei

<400> SEQUENCE: 32
cagagatgtt atagctagtg atataac                                           27

<210> SEQ ID NO 33
<211> LENGTH: 31
<212> TYPE: DNA
<213> ORGANISM: Plasmodium berghei

<400> SEQUENCE: 33
ctaagtagca actattttgt aaaattatat c                                      31

<210> SEQ ID NO 34
<211> LENGTH: 26
<212> TYPE: DNA
<213> ORGANISM: Plasmodium berghei

<400> SEQUENCE: 34
gcataagatt cacaaataca aaaagg                                            26

<210> SEQ ID NO 35
<211> LENGTH: 18
<212> TYPE: DNA
<213> ORGANISM: Plasmodium berghei

<400> SEQUENCE: 35
ggtcttcctc taagtatt                                                     18

<210> SEQ ID NO 36
<211> LENGTH: 18
<212> TYPE: DNA
<213> ORGANISM: Plasmodium berghei
```

```
<400> SEQUENCE: 36
ccagatggtc aaatgccc                                                   18

<210> SEQ ID NO 37
<211> LENGTH: 20
<212> TYPE: DNA
<213> ORGANISM: Plasmodium berghei

<400> SEQUENCE: 37
ctgtggtgat ggccatgaac                                                 20

<210> SEQ ID NO 38
<211> LENGTH: 23
<212> TYPE: DNA
<213> ORGANISM: Plasmodium berghei

<400> SEQUENCE: 38
gcgccctcat agcccgccaa atc                                             23

<210> SEQ ID NO 39
<211> LENGTH: 24
<212> TYPE: DNA
<213> ORGANISM: Plasmodium berghei

<400> SEQUENCE: 39
ccgccaaatc agtcctgtag cttc                                            24

<210> SEQ ID NO 40
<211> LENGTH: 24
<212> TYPE: DNA
<213> ORGANISM: Plasmodium berghei

<400> SEQUENCE: 40
tgcgcgcttg gcgtaatcat ggtc                                            24

<210> SEQ ID NO 41
<211> LENGTH: 21
<212> TYPE: DNA
<213> ORGANISM: Artificial
<220> FEATURE:
<223> OTHER INFORMATION: synthetic oligonucleotides

<400> SEQUENCE: 41
gctagagctg cagccatcag c                                               21

<210> SEQ ID NO 42
<211> LENGTH: 749
<212> TYPE: DNA
<213> ORGANISM: Artificial
<220> FEATURE:
<223> OTHER INFORMATION: synthetic oligonucleotide fusion protein E coli
      methylase and FusM from Chlamydomonas

<400> SEQUENCE: 42
ccgccaaatc agtcctgtag cttccatatc tgattcgcaa tcttgccttg cacctgcctg     60
ccacgctcat accatgtcgc cgtgacccca aaacaggcct gtctgtccgg ccagctcaag    120
gacctgtggg aggcggacct ggcgcgtacc gcggacggcc gggtgccgct gtacatgatc    180
accaggttca ctggcggcag cgagggctaa tcgcgccgga aaatatatca gtaaccgatt    240
catacagcac cgggaatgcc gcacaggcaa tgctggagaa actgctgcaa atttatgatg    300
ttaaaacgtt ggtggcgcag cttaatggtg taggtgagaa tcactggagc gcggcaattt    360
```

```
taaaacgtgc gctggcgaat gactcggcat ggcaccgttt aagtgagaaa gagttcgccc    420
atctgcaaac gttattaccc aaaccaccgg cacatcatcc gcattatgcg tttcgcttta    480
tcgatctatt cgccggaatt ggcggcatcc gtcgcggttt tgaatcgatt ggcggacagt    540
gcgtgttttc cagcgaatgg aacaaacatg cggtacgcac ttataaagcc aaccattatt    600
gcgatccggc gacgcatcat tttaatgaag atatccgcga catcaccctc agccataaag    660
aaggcgtgag tgatgaggcg gcggcggaac atattcgtca acaatttcac acaggaaaca    720
gctatgacca tgattacgcc aagcgcgca                                      749
```

<210> SEQ ID NO 43
<211> LENGTH: 23
<212> TYPE: DNA
<213> ORGANISM: Chlamydomonas reinhardtii

<400> SEQUENCE: 43

```
atgtcgccgt gaccccaaaa cag                                             23
```

<210> SEQ ID NO 44
<211> LENGTH: 24
<212> TYPE: DNA
<213> ORGANISM: Chlamydomonas reinhardtii

<400> SEQUENCE: 44

```
ctggctggtg acaggcagcg cgaa                                            24
```

<210> SEQ ID NO 45
<211> LENGTH: 22
<212> TYPE: DNA
<213> ORGANISM: Chlamydomonas reinhardtii

<400> SEQUENCE: 45

```
ttggctgcgc tccttctggc gc                                              22
```